(12) United States Patent
Basu et al.

(10) Patent No.: US 8,076,534 B2
(45) Date of Patent: Dec. 13, 2011

(54) CHLAMYDOMONAS GLUCAN DIKINASE GENE, ENZYME AND MODIFIED STARCH, USES, METHODS FOR PRODUCTION THEREOF

(75) Inventors: Shib Sankar Basu, Research Triangle Park, NC (US); Michael B. Lanahan, Cary, NC (US); Mark Kinkema, Queensland (AU)

(73) Assignee: Syngenta Participations AG, Basel (CH)

( * ) Notice: Subject to any disclaimer, the term of this patent is extended or adjusted under 35 U.S.C. 154(b) by 426 days.

(21) Appl. No.: 11/996,076

(22) PCT Filed: Jun. 22, 2006

(86) PCT No.: PCT/US2006/024405
§ 371 (c)(1),
(2), (4) Date: Nov. 13, 2008

(87) PCT Pub. No.: WO2007/018770
PCT Pub. Date: Feb. 15, 2007

(65) Prior Publication Data
US 2009/0205080 A1    Aug. 13, 2009

(51) Int. Cl.
C12N 15/82      (2006.01)
C12N 15/00      (2006.01)
C12N 15/09      (2006.01)
C07H 21/04      (2006.01)
A01H 5/00       (2006.01)

(52) U.S. Cl. ..... 800/284; 800/295; 800/278; 435/320.1; 435/468; 536/23.1; 536/23.2

(58) Field of Classification Search .................. None
See application file for complete search history.

(56) References Cited

U.S. PATENT DOCUMENTS 6,596,928 B1   7/2003   Landschutze
6,734,340 B2   5/2004   Schewe

FOREIGN PATENT DOCUMENTS

WO    94/28146    12/1994

OTHER PUBLICATIONS

Ritte et al 2002 PNAS 99:7166-7171, provided by Applicant.*
Ritte et al., "The Starch-related R1 proteian is an alpha-glucan, water dikinase", PNAS. vol. 99, No. 10, pp. 7166-7171 (May 2002) see entire document, especially Fig. 1.
Ritte et al., "Phosphorylation of transitory starch is increased during degradation", Plant Physiology vol. 135, pp. 2068-2077 (Aug. 2004) see entire document, especially p. 2068, right column, 2nd paragraph.
Syngenta Participations AG, PCT/US06/24405 International Application, International Search Report, Oct. 23, 2007.

\* cited by examiner

Primary Examiner — Brent T Page

(57) ABSTRACT

The present invention relates the nucleotide sequence from *Chlamydomonas reinhardtii* encoding a glucan dikinase enzyme and to methods of use; to modified starch, as well as production and uses thereof. The starch has modified properties of viscosity and a modified phosphate content.

19 Claims, 20 Drawing Sheets

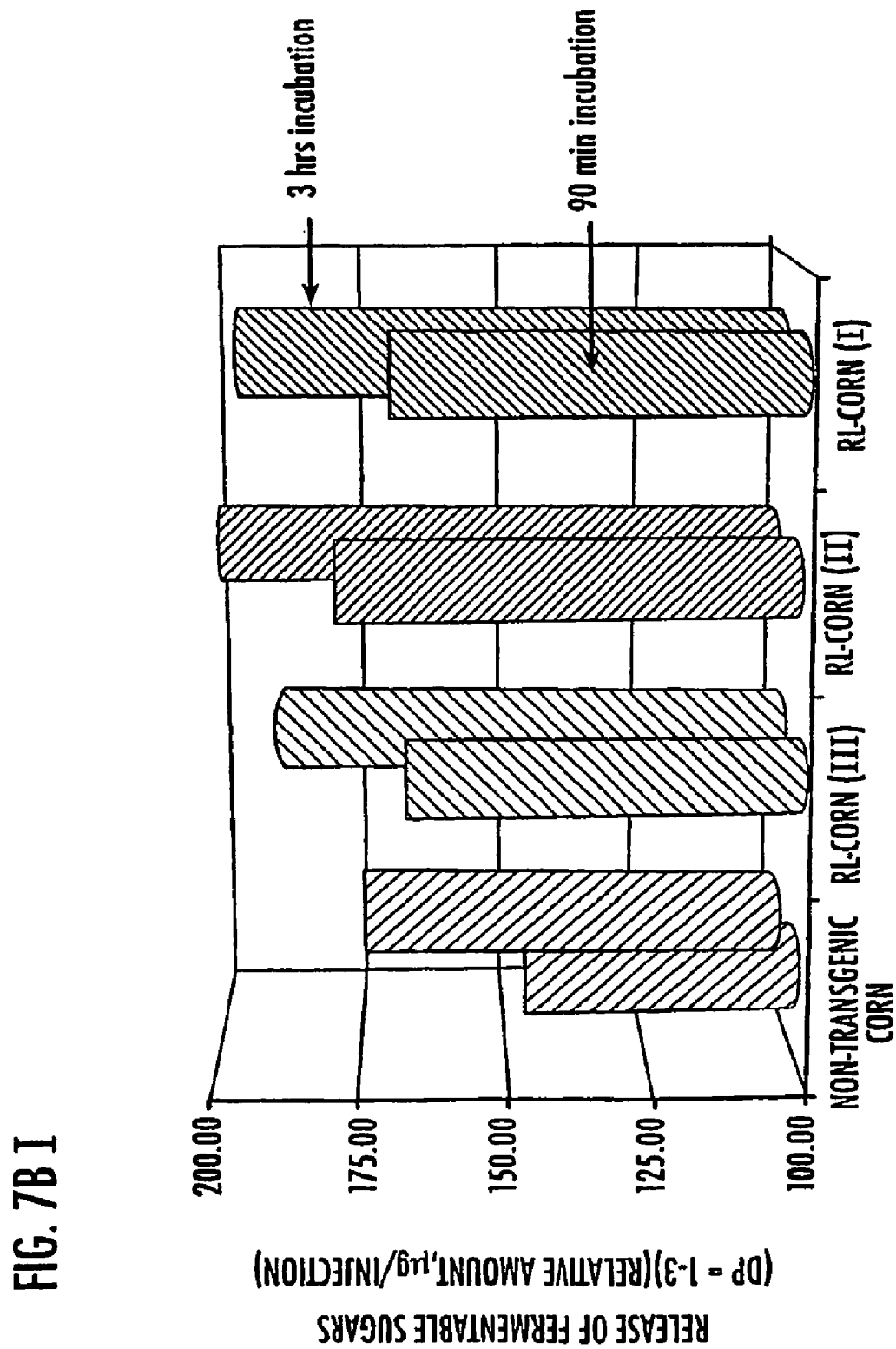
FIG. 7B I

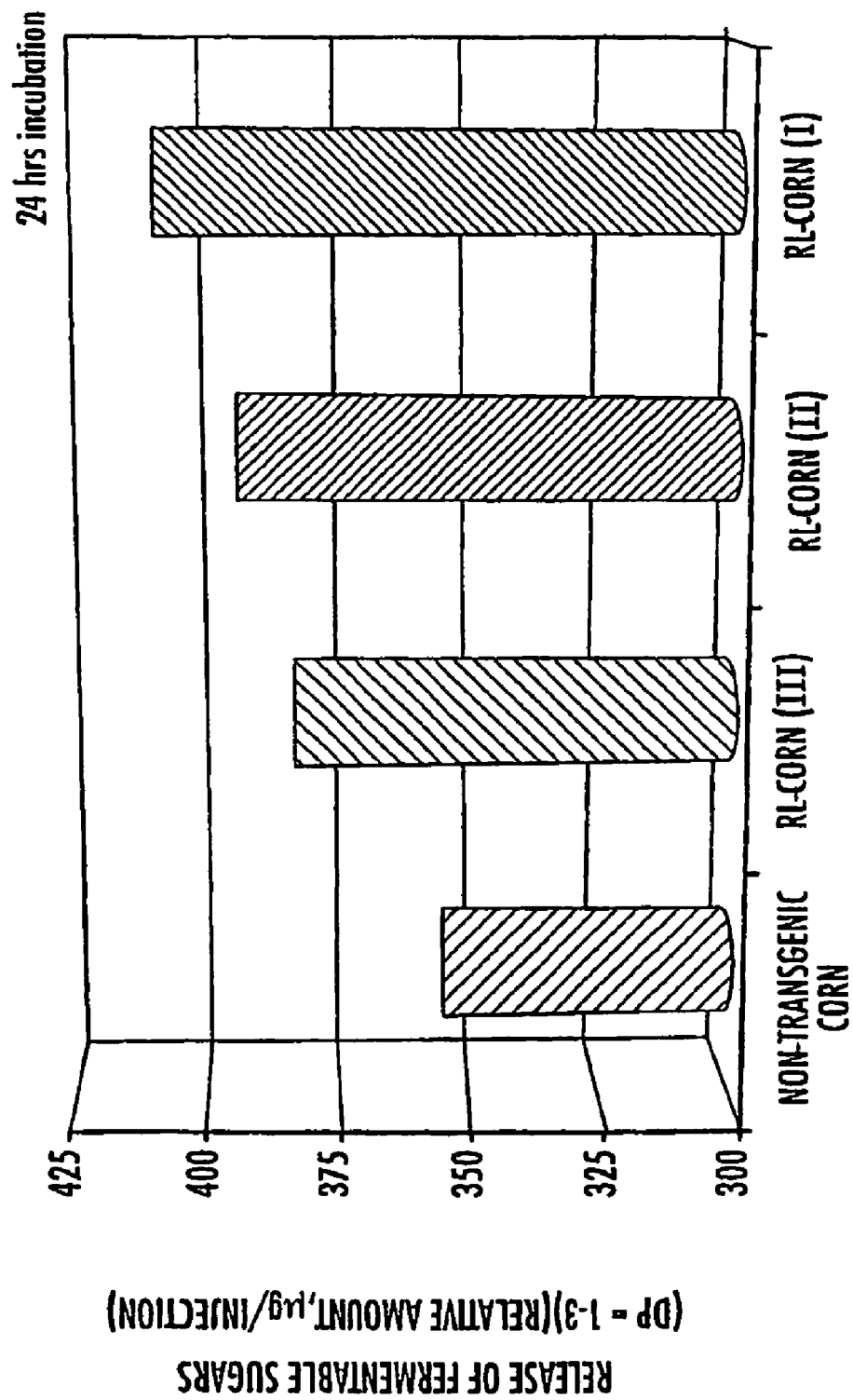
FIG. 7B II

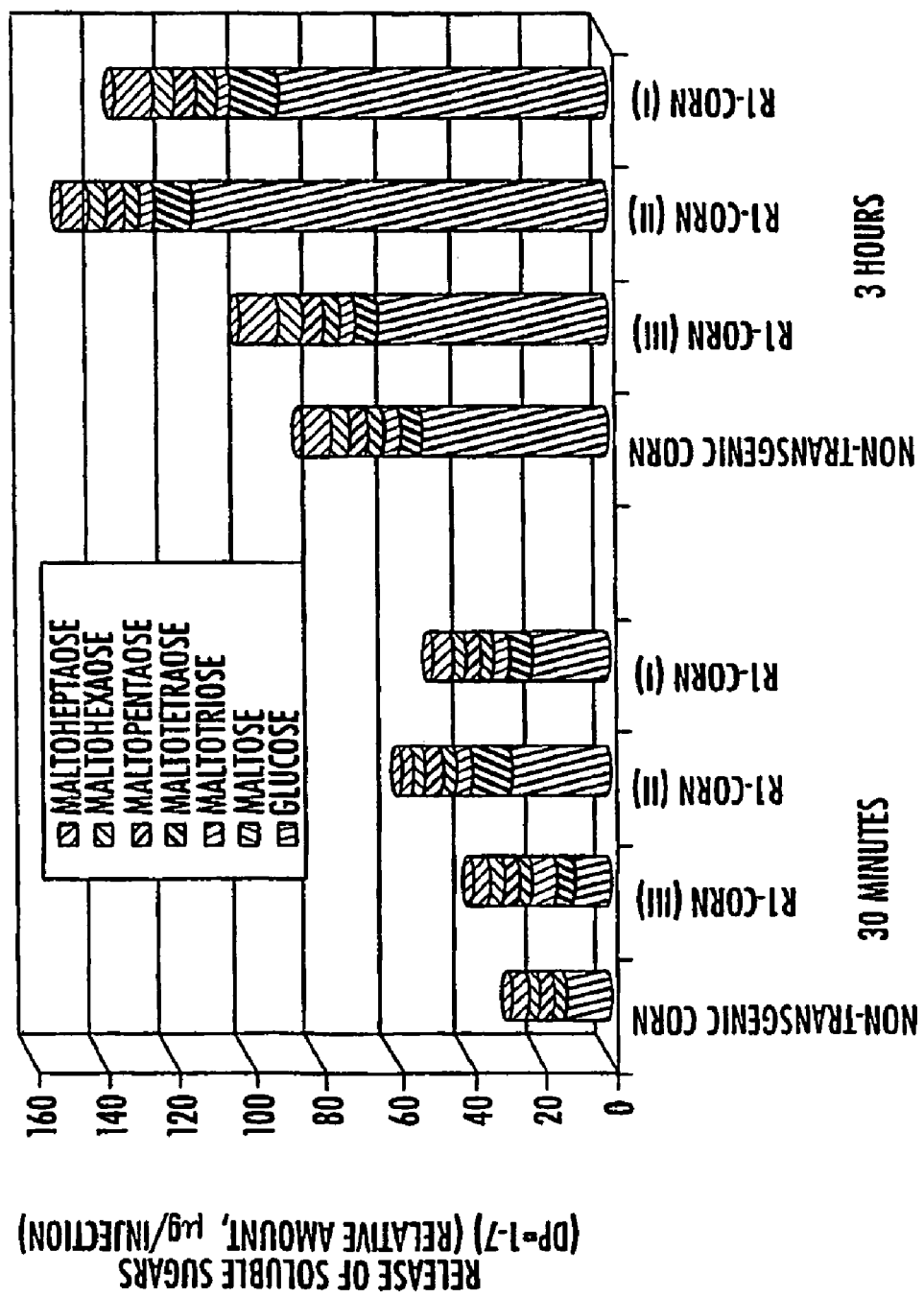
FIG. 7C I

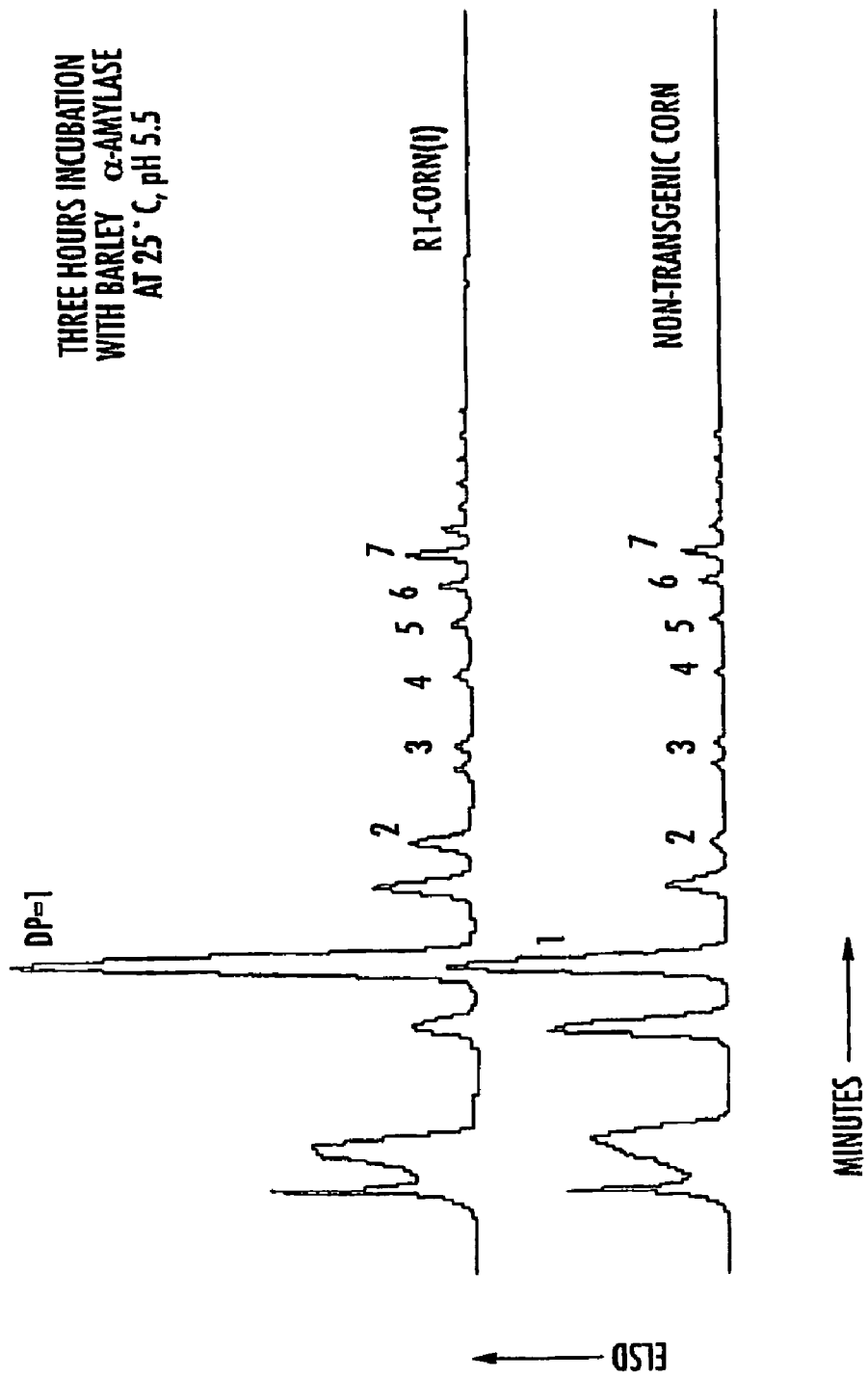
FIG. 7C II

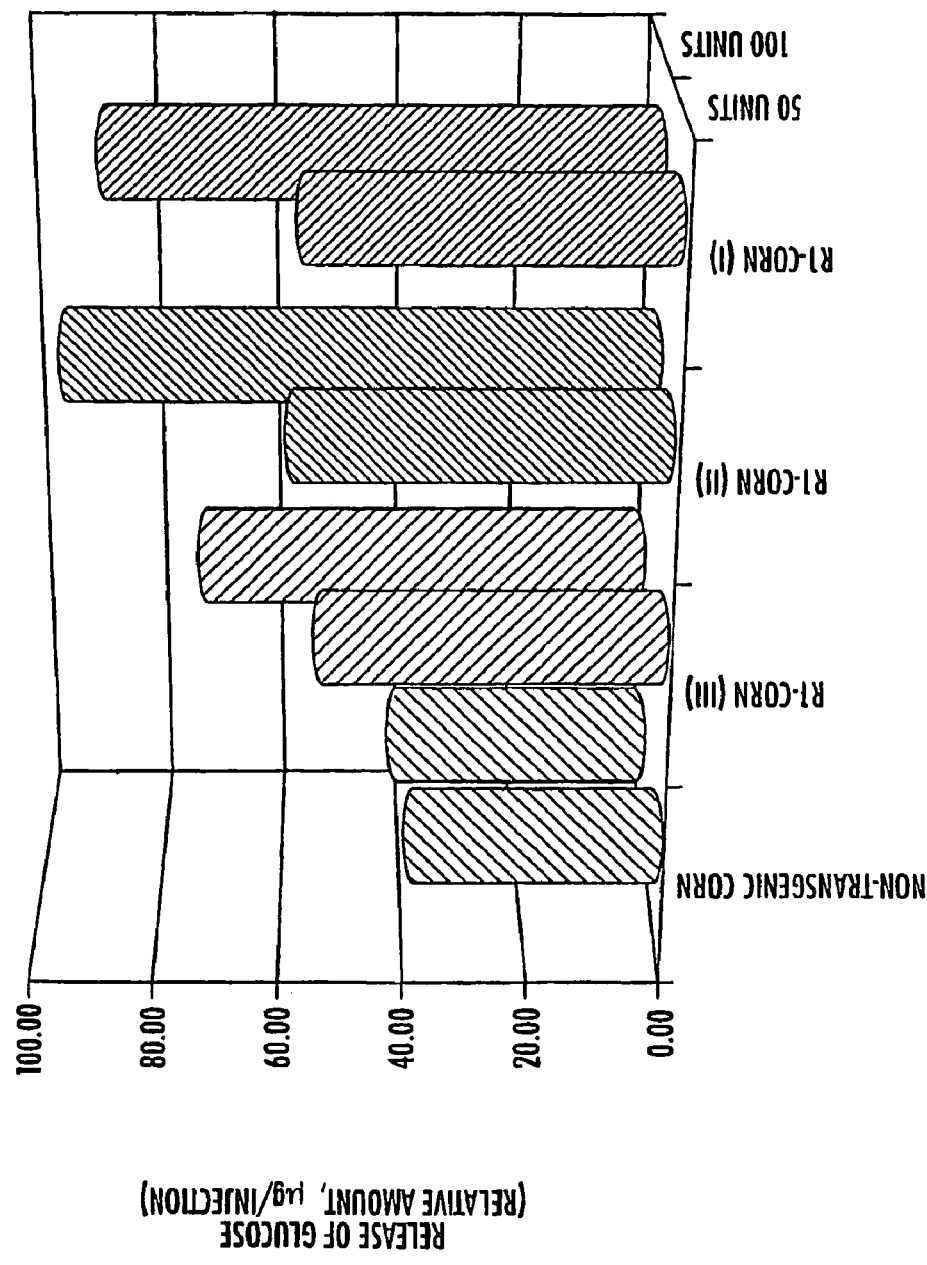
FIG. 7D I

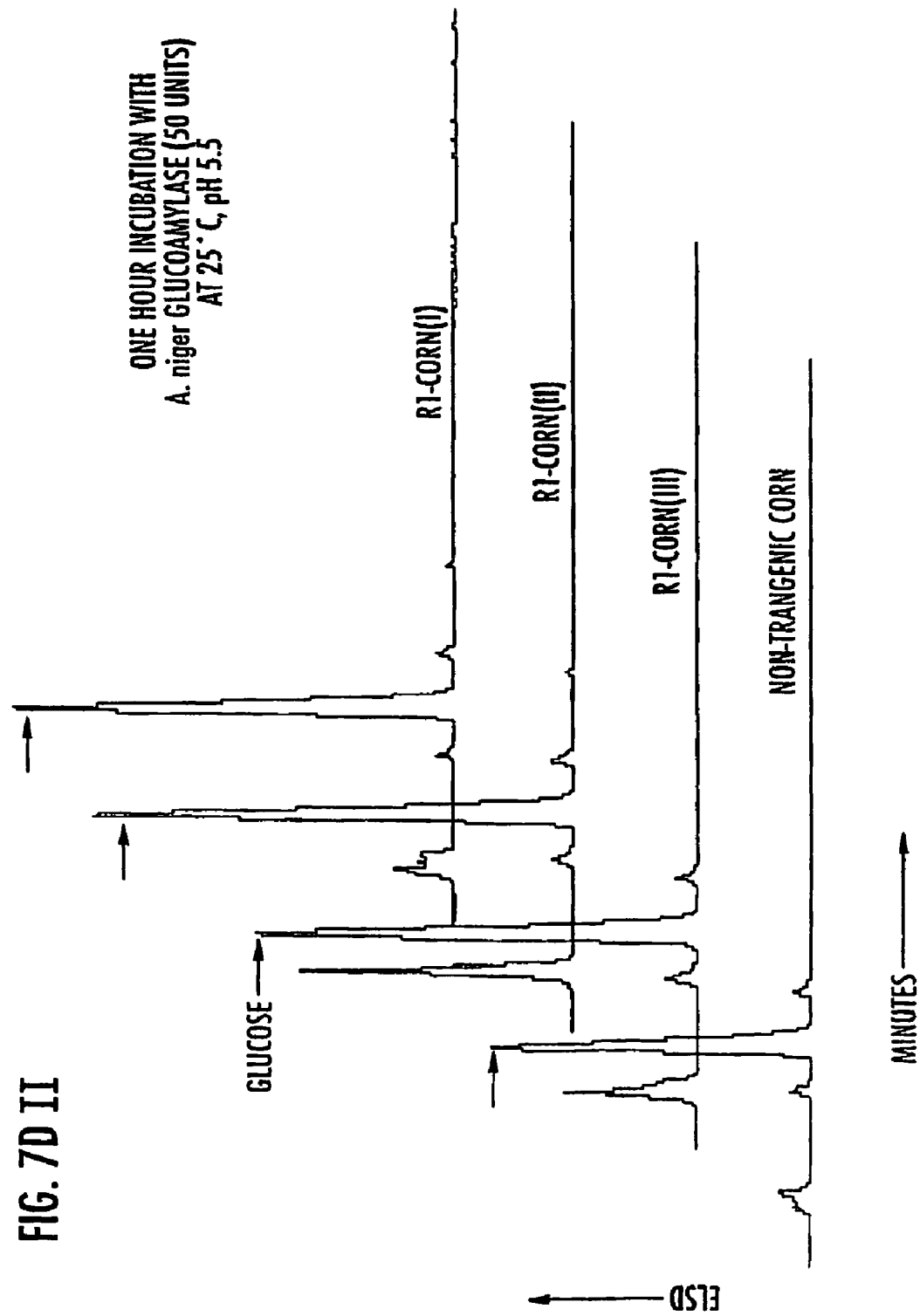

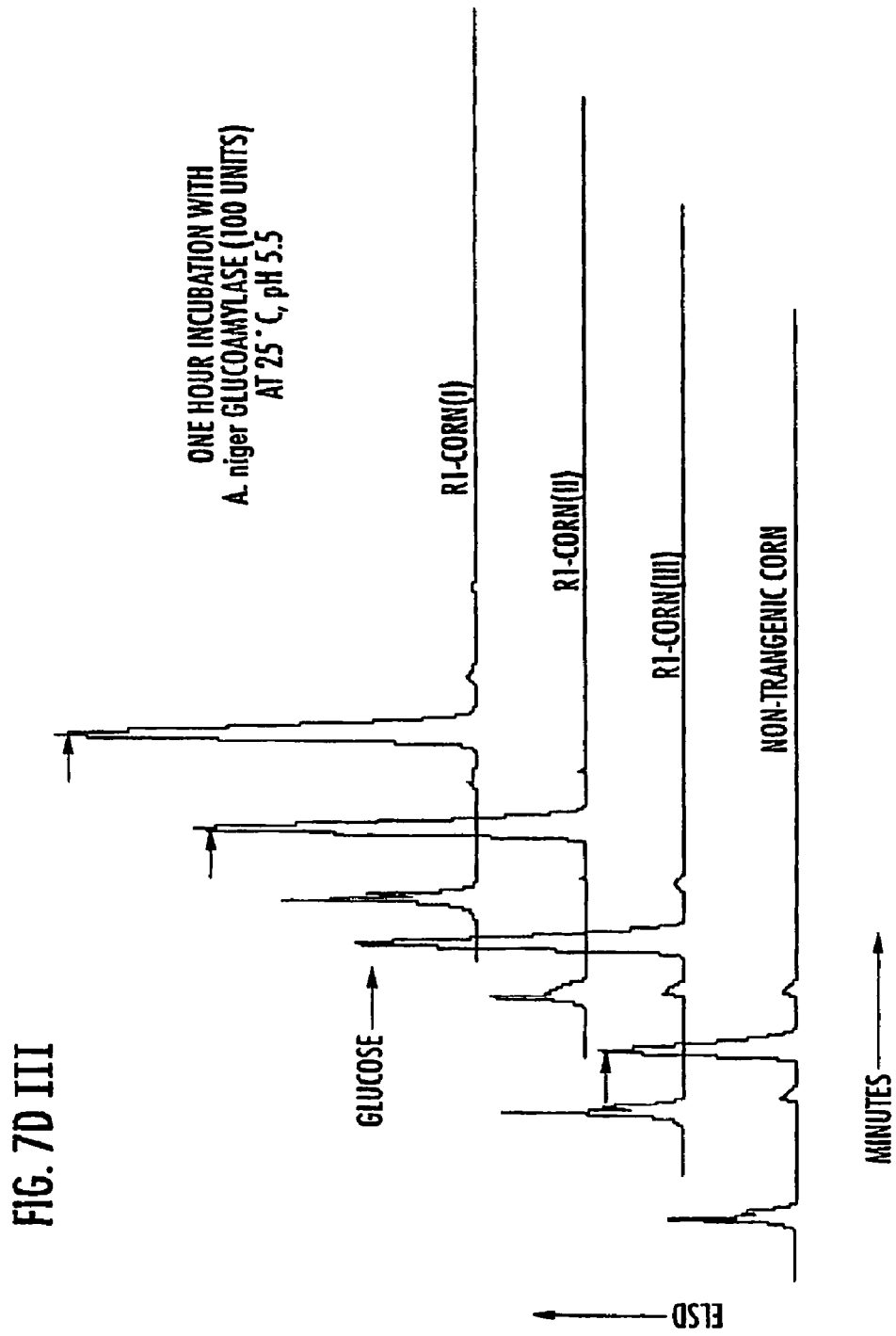

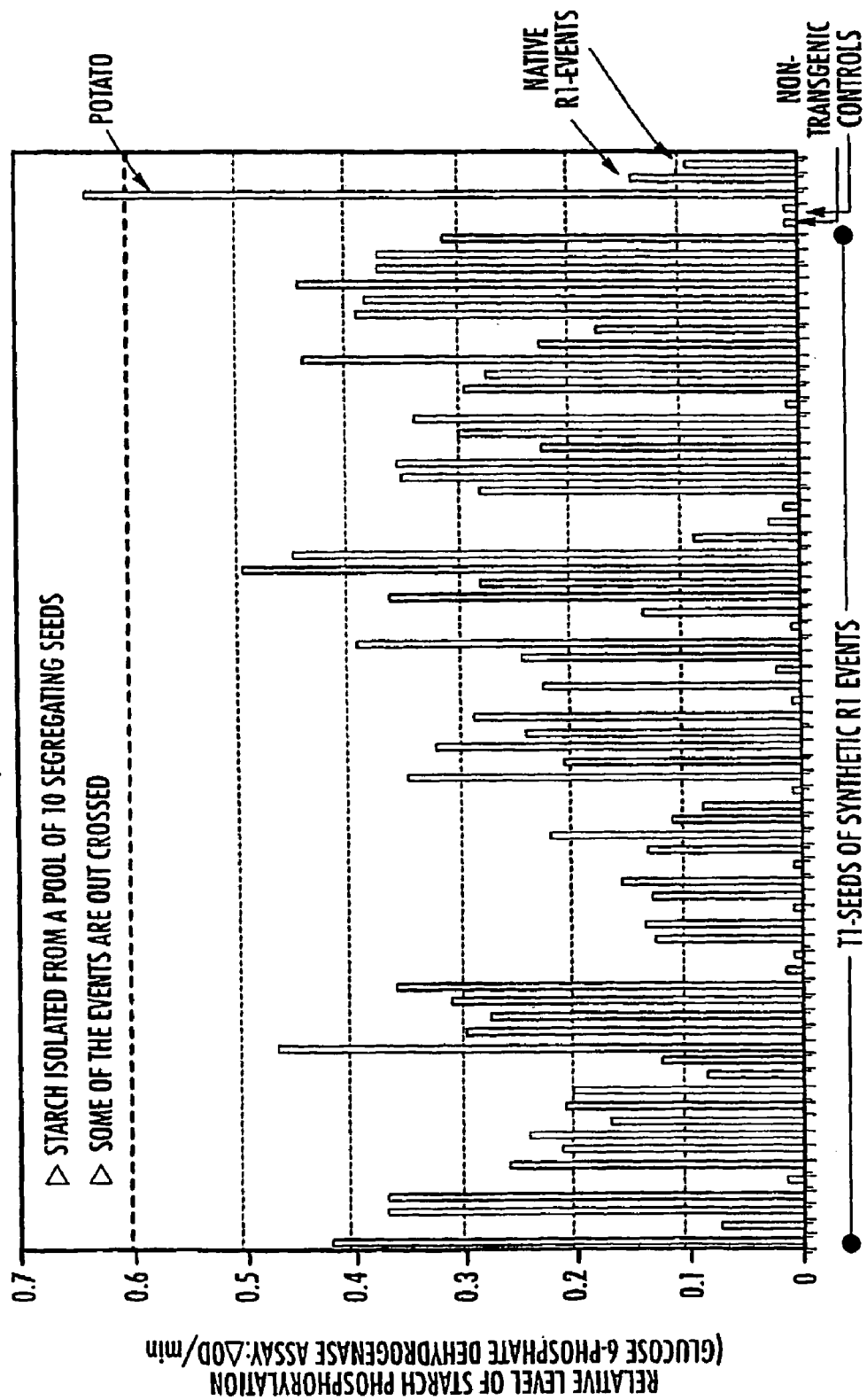

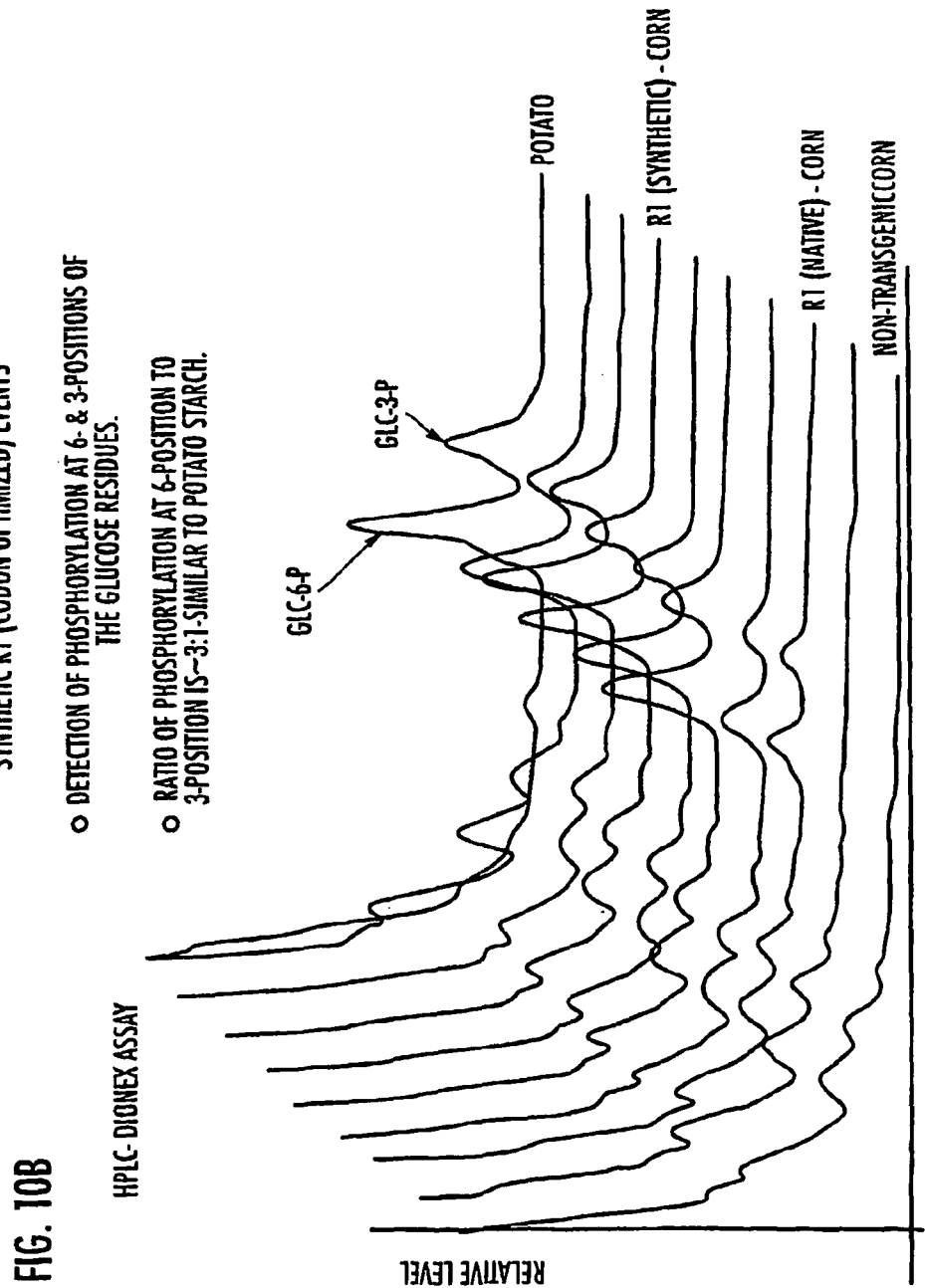

SEQUENCE LISTING

<160> NUMBER OF SEQ ID NOS: 31

<210> SEQ ID NO 1
<211> LENGTH: 31
<212> TYPE: DNA
<213> ORGANISM: Artificial Sequence
<220> FEATURE:
<223> OTHER INFORMATION: Primer
<220> FEATURE:

```
<221> NAME/KEY: misc_feature
<222> LOCATION: (1)..(31)

<400> SEQUENCE: 1
tgcagccatg ggtaattcct tagggaataa c                              31

<210> SEQ ID NO 2
<211> LENGTH: 32
<212> TYPE: DNA
<213> ORGANISM: Artificial Sequence
<220> FEATURE:
<223> OTHER INFORMATION: Primer

<400> SEQUENCE: 2
tccaagtcga ctcacatctg aggtcttgtc tg                             32

<210> SEQ ID NO 3
<211> LENGTH: 25
<212> TYPE: PRT
<213> ORGANISM: Potato

<400> SEQUENCE: 3

Tyr Thr Pro Glu Lys Glu Lys Glu Glu Tyr Glu Ala Ala Arg Thr Glu
1               5                   10                  15

Leu Gln Glu Glu Ile Ala Arg Gly Ala
            20                  25

<210> SEQ ID NO 4
<211> LENGTH: 38
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(38)

<400> SEQUENCE: 4
catatgggga tagacgctgc cgggctggac accaacgg                       38

<210> SEQ ID NO 5
<211> LENGTH: 42
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(42)

<400> SEQUENCE: 5
gaattcctac acctgcgggc gcgtctgcac aacggtgatg gc                  42

<210> SEQ ID NO 6
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(32)

<400> SEQUENCE: 6
ggatccccgg ctcctgccgc ggctacctgg gc                             32

<210> SEQ ID NO 7
```

-continued

<210> SEQ ID NO 7
<211> LENGTH: 33
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(33)

<400> SEQUENCE: 7
ggatcctgtt gccggcggcg ctggcgctgg cgg                          33

<210> SEQ ID NO 8
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(21)

<400> SEQUENCE: 8
gctggagctg aaggagacca g                                      21

<210> SEQ ID NO 9
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(23)

<400> SEQUENCE: 9
ggtgttctgc gagctggtca agg                                    23

<210> SEQ ID NO 10
<211> LENGTH: 22
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(22)

<400> SEQUENCE: 10
gatccggagg gctgcgtggc cc                                     22

<210> SEQ ID NO 11
<211> LENGTH: 19
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(19)

<400> SEQUENCE: 11
gccaccaaca cctggtacg                                         19

<210> SEQ ID NO 12
<211> LENGTH: 21
<212> TYPE: DNA
<213> ORGANISM: Artificial Sequence
<220> FEATURE:
<223> OTHER INFORMATION: Primer

```
<220> FEATURE:
<221> NAME/KEY: misc_feature
<222> LOCATION: (1)..(21)

<400> SEQUENCE: 12
gacgagctgt ggcgcgtggc g                                                   21

<210> SEQ ID NO 13
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(17)

<400> SEQUENCE: 13
cgcaggagtg ggtgcgc                                                        17

<210> SEQ ID NO 14
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(23)

<400> SEQUENCE: 14
ctggcgtgtg ctgtcggacg cag                                                 23

<210> SEQ ID NO 15
<211> LENGTH: 22
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(22)

<400> SEQUENCE: 15
cccgaggacc tgctgggcgt gc                                                  22

<210> SEQ ID NO 16
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(23)

<400> SEQUENCE: 16
agtcatcaac gaccagctgg cgg                                                 23

<210> SEQ ID NO 17
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(25)

<400> SEQUENCE: 17
```
cgtaccgcgc ccaacctgtc tgccg                                              25

<210> SEQ ID NO 18
<211> LENGTH: 27
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(27)

<400> SEQUENCE: 18
gctcccgcga gtgggtgatg ccggacg                                            27

<210> SEQ ID NO 19
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(23)

<400> SEQUENCE: 19
accaccacct gggtgcgctg ctg                                                23

<210> SEQ ID NO 20
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(25)

<400> SEQUENCE: 20
tgggcgtgcc agcgcgcgag gcagc                                              25

<210> SEQ ID NO 21
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(32)

<400> SEQUENCE: 21
tcttccggta gtccgagtac ttccacttgc cc                                      32

<210> SEQ ID NO 22
<211> LENGTH: 31
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(31)

<400> SEQUENCE: 22
cccgacgacg tgcccatctg cgaggcctac c                                       31

<210> SEQ ID NO 23

```
<211> LENGTH: 31
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(31)

<400> SEQUENCE: 23
ggtaggcctc gcagatgggc acgtcgtcgg g                              31

<210> SEQ ID NO 24
<211> LENGTH: 36
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(36)

<400> SEQUENCE: 24
catatggacg acgccaccaa cacctggtac gatgac                         36

<210> SEQ ID NO 25
<211> LENGTH: 34
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(34)

<400> SEQUENCE: 25
gaattctaca cctgcgggcg cgtctgcaca acgg                           34

<210> SEQ ID NO 26
<211> LENGTH: 4074
<212> TYPE: DNA
<213> ORGANISM: Chlamydomonas

<400> SEQUENCE: 26
atggggatag acgctgccgg gctggacacc aacggccgcg cgcgcgtggt gcttcacttg      60
gacggcgagg aggcgtcgga cttcctgaac ttcgtgctga aggacgacgc caccaacacc     120
tggtacgaca caacggcac  caacttcaag gtggagctgc gcgccgacgc ctcgcccagc     180
gcgcccaagc tggaccagct gccaaaggac ctgtgcgaca agtgggcctg ggtgcgctgg     240
gactttgtgg gccggccgca gcgctccgcc gaggcggccg cctccgagta cgaccgcggc     300
gtcagcgaga tgaaggagct gctggcgcgc gggcgggtgc tggacgagct gtggcgcgtg     360
gcggagggca gtggaagta  ttcggactac cgcaagaagg tggtgacgcc caccattggc     420
gacggcaccg cgccgctgtc cgcccagccg caggcgcagc agcccgcggg cgccccggcg     480
gcggcggcgc tgccggccat tcccgaggac ctgctgggcg tgcaggccta catcctagtc     540
atcaacgacc agctggcggc gggctccagc ctggaggagg tggcgggccg cctcaactac     600
acgctgaagc agcccacgcc gccggcctcc acgcgcggca cgcccgccgg cagccgcgcc     660
ggcagcgcca cctcgtcgct ggacggcggc gcggcggcgg cgcccgcgcg gcctcaggc     720 ccgccgccgc aggtgggggc gccgctgggc acgcccaagc gcaacccgct ggacatgatc     780
aagcgtaccg cgcccaacct gtctgccgag cgctcggtgg tggagcggcc gctggacttc     840
ctggtgcagc gctttgcggt ggaccccgcc accaagtggc gccgcacatt cccgctgggc     900
```

```
ggcaaggcgg agatgctggt ggtggtgcgc caggaggctg agaacaagcc cattcgtgtg    960
gacctggtga cggacacggc ctcggacgtg gtgctgcact ggggcgtcag ccccattggc   1020
tcccgcgagt gggtgatgcc ggacgacggc gtgctgcccg agggcagcat ggtgatgcac   1080
aaggcggtgg agacgcccct cctcaactgc gacgacgacg agtgcgacgt ggagatcagc   1140
ggcgccaagg tgccgctgca gcgcatcacc atcaacctgc cggcggacca ccacctgggt   1200
gcgctgctgt tcgtgctgcg ctccagcgac aacaccatgt ggtacaagga cgcgggcggc   1260
aacttcacgg tgccgctgcc ctccaaggac aagcctgttg aggacactcg ctccatggac   1320
gtcatcaagg acgagctcag ccgcaccatc atcgaggcgg aggtcaacag cagcatgtgg   1380
acactcatgc acaggttcaa caaggccgcg gacctggtca gcgaggtgct caacggctac   1440
tacgaccagc tggacgtggc cgacgccatg agccgcatct acgtctggct gcgctacagc   1500
gccacccgcc acctcacctg gcagcgcaac tacaacacgc agccgcgcat cctgtcagca   1560
gcgcaggagc gcctcaccaa caccatcgcc aacgcgcacg gccgcaccac gggagaggcg   1620
caggagtggg tgcgcatgat gctcacaacg gtgggccgcg gcggcgacgg ccagaagatc   1680
cgcgacgaga tcctgcacat catgcaccgc aaccacatcc ccgagcgcaa ggggctgtgg   1740
atggaggagt ggcaccagaa gctgcacaac aacaccacgc ccgacgacgt gcccatctgt   1800
gaggcctacc tggccttcct ggagggcaac ggcaacatcg cgcctactg gcgtgtgctg    1860
tcggacgcag gcatcacgcg gcagcggctg gagggctttg accgcgccat cacgctggag   1920
cccgagtact acccggagaa gcgcgacgcg ctcatccgcg acttccgcaa ctacctgggc   1980
atcctcaagg ccgtgcacag cggcgccgac ctgtccgcca gcgccagcgc cgccggcaac   2040
aggatccccg gctcctgccg cggctacctg ggctacgtgc tgagccacgt gggcgacagc   2100
cagatcctgc cgctgctgga ggcgtgcgtg gaggcgcgca ccgagctggc gctgagcggc   2160
acgctgcccg gcagccgcga gctgctgtac ctggacctgg cgctggagga ccaggcgcgc   2220
caggcggcgg agcggggcgt gggcgcggcg ggcttcggcg ccgccgcctt catgcggccg   2280
ctgctgcaga acctgtgcct cagcctgggc aacaacgagg agctgtgcta ctgcctcaag   2340
gcctggaacg agctgcccca gtcggtgcgc acgggcgggc ggcccaacaa ggaggaggcg   2400
ctgctggcgt ggcggtggt caaccgcgtg cggagagcgc tcgcggacat ctctgaccgc   2460
accgtgaacc gcatcggcga cgtgtcgtcc gcctacggcc gcgcgttcgg cgtggagcac   2520
tgggcctacg agctgtttgc ggaggaggtc atccgcggcg ggccggcctt cgcggtgtcg   2580
ctggtcatca ccgccattga gcccatgctg cgcaacgccg cggcgctggg tgcgtggcag   2640
gtgatcagcc ccattgcggc cacgggccgc gtggaggtgg tggcgggact gcacgaggtg   2700
caggacaaga cctacgacac gcccaccgtg ctcatcgcgg agcaggtgac tggcgaggag   2760
gagatcccgg agggctgcgt ggccgtcatc acgcccgacg cgcccgacgt gctgtcgcac   2820
gtgtcggtgc gcgcgcgcaa catgcgtgtg ctgttcgcca cctgccacga cgacgggccg   2880
ctcaagcagc tgcgcgaggc caagggcaag tggctgcact tcacgccctc tgccagcggc   2940
gccgtgtcct ggaatgagac cactgcgag gcggcgggcg cagcggacga cagctcgcac    3000
tccacagtgt ccaagcccac gaagggcctg aagattgagg tgcccaactg gtgcgggcgc   3060
tgggtggtgg gcatggacga gtacaaggac ggcgtggtgg cgccaagtc caagaacctg   3120
gcgggcctgc gcggccgcct gcccgacaac atcaacctgc cgcctccgt cacgctgccc    3180
ttcggctgct tcgagcaggc gctggagctg aaggagaacc aggacatcaa gaccaagctg   3240
aagaagcacg tggacgaggt gcacaagcac tccaagcacc acgccgacca caccacctcc   3300
```

```
aacgggacgg ggccgtcgcc ggcggcgctg ctggccgagt gccgcaagct ggccatgcag    3360
gtggtggtgc ccaagcagat ccgcgacgac ctggcgcaag ccatgaaggg cgcaggcatc    3420
ccgccgcccg agaccgagga gcgctgggcg ctggcgctgg aggccctgcg cggcgtgtgg    3480
gcgtccaagt acaacgaccg cgcctactac tcgctgcgca aggccgggct ggactttgac    3540
agcgtgcgca tggcggtgct ggtgcagcgc gtggtgccgg cgcagtacgc gttcgtgatc    3600
cacacgcgca accctccaa caacgacgag cgcgaggtgt ctgcgagct ggtcaagggc      3660 ctgggcgagt cgctggtgag cggcatggtg cccggcagcg cggtggcgtt caaggccgcc    3720
aaggacgagg cggggctggg gtcgcccgag gtgctgtgct acgccagcaa gagcgaggcc    3780
atgtacgtgc gcgacagcct catcttcagg tccgactcaa acggcgagga cctggaggga    3840
tacgcaggcg ccggcctgta cgagtccatc accatggacc ccagcctgct caagaaggtg    3900
gactacatgg aggaccggct ggtgcaggac cccgcgtaca ggcgcgacct gctgtcgcgc    3960
atctgccgcc tgggcgcctc cattgagggc gcgctgggca cggcgcagga cattgagggc    4020
gtggtggcgc ccgacggagc catcaccgtt gtgcagacgc gcccgcaggt gtag          4074

<210> SEQ ID NO 27
<211> LENGTH: 1357
<212> TYPE: PRT
<213> ORGANISM: Chlamydomonas

<400> SEQUENCE: 27

Met Gly Ile Asp Ala Ala Gly Leu Asp Thr Asn Gly Arg Ala Arg Val
1               5                   10                  15

Val Leu His Leu Asp Gly Glu Glu Ala Ser Asp Phe Leu Asn Phe Val
            20                  25                  30

Leu Lys Asp Asp Ala Thr Asn Thr Trp Tyr Asp Asn Asn Gly Thr Asn
        35                  40                  45

Phe Lys Val Glu Leu Arg Ala Asp Ala Ser Pro Ser Ala Pro Lys Leu
    50                  55                  60

Asp Gln Leu Pro Lys Asp Leu Cys Asp Lys Trp Ala Trp Val Arg Trp
65                  70                  75                  80

Asp Phe Val Gly Arg Pro Gln Arg Ser Ala Glu Ala Ala Ala Ser Glu
                85                  90                  95

Tyr Asp Arg Gly Val Ser Glu Met Lys Glu Leu Leu Ala Arg Gly Arg
            100                 105                 110

Val Leu Asp Glu Leu Trp Arg Val Ala Glu Gly Lys Trp Lys Tyr Ser
        115                 120                 125

Asp Tyr Arg Lys Lys Val Val Thr Pro Thr Ile Gly Asp Gly Thr Ala
    130                 135                 140

Pro Leu Ser Ala Gln Pro Gln Ala Gln Gln Pro Ala Gly Ala Pro Ala
145                 150                 155                 160

Ala Ala Ala Leu Pro Ala Ile Pro Glu Asp Leu Leu Gly Val Gln Ala
                165                 170                 175

Tyr Ile Leu Val Ile Asn Asp Gln Leu Ala Ala Gly Ser Ser Leu Glu
            180                 185                 190

Glu Val Ala Gly Arg Leu Asn Tyr Thr Leu Lys Gln Pro Thr Pro Pro
        195                 200                 205

Ala Ser Thr Arg Gly Thr Pro Ala Gly Ser Arg Ala Gly Ser Ala Thr
    210                 215                 220

Ser Ser Leu Asp Gly Gly Ala Ala Ala Pro Ala Arg Pro Ser Gly
225                 230                 235                 240
```

-continued

```
Pro Pro Pro Gln Val Gly Ala Pro Leu Gly Thr Pro Lys Arg Asn Pro
            245                 250                 255

Leu Asp Met Ile Lys Arg Thr Ala Pro Asn Leu Ser Ala Glu Arg Ser
        260                 265                 270

Val Val Glu Arg Pro Leu Asp Phe Leu Val Gln Arg Phe Ala Val Asp
    275                 280                 285

Pro Ala Thr Lys Trp Arg Arg Thr Phe Pro Leu Gly Gly Lys Ala Glu
290                 295                 300

Met Leu Val Val Arg Gln Glu Ala Glu Asn Lys Pro Ile Arg Val
305                 310                 315                 320

Asp Leu Val Thr Asp Thr Ala Ser Asp Val Leu His Trp Gly Val
                325                 330                 335

Ser Pro Ile Gly Ser Arg Glu Trp Val Met Pro Asp Asp Gly Val Leu
            340                 345                 350

Pro Glu Gly Ser Met Val Met His Lys Ala Val Glu Thr Pro Phe Leu
        355                 360                 365

Asn Cys Asp Asp Asp Glu Cys Asp Val Glu Ile Ser Gly Ala Lys Val
    370                 375                 380

Pro Leu Gln Arg Ile Thr Ile Asn Leu Pro Ala Asp His His Leu Gly
385                 390                 395                 400

Ala Leu Leu Phe Val Leu Arg Ser Ser Asp Asn Thr Met Trp Tyr Lys
                405                 410                 415

Asp Ala Gly Gly Asn Phe Thr Val Pro Leu Pro Ser Lys Asp Lys Pro
            420                 425                 430

Val Glu Asp Thr Arg Ser Met Asp Val Ile Lys Asp Glu Leu Ser Arg
        435                 440                 445

Thr Ile Ile Glu Ala Glu Val Asn Ser Ser Met Trp Thr Leu Met His
    450                 455                 460

Arg Phe Asn Lys Ala Ala Asp Leu Val Ser Glu Val Leu Asn Gly Tyr
465                 470                 475                 480

Tyr Asp Gln Leu Asp Val Ala Asp Ala Met Ser Arg Ile Tyr Val Trp
                485                 490                 495

Leu Arg Tyr Ser Ala Thr Arg His Leu Thr Trp Gln Arg Asn Tyr Asn
            500                 505                 510

Thr Gln Pro Arg Ile Leu Ser Ala Ala Gln Glu Arg Leu Thr Asn Thr
        515                 520                 525

Ile Ala Asn Ala His Gly Arg Thr Thr Gly Glu Ala Gln Glu Trp Val
    530                 535                 540

Arg Met Met Leu Thr Thr Val Gly Arg Gly Gly Asp Gly Gln Lys Ile
545                 550                 555                 560

Arg Asp Glu Ile Leu His Ile Met His Arg Asn His Ile Pro Glu Arg
                565                 570                 575

Lys Gly Leu Trp Met Glu Glu Trp His Gln Lys Leu His Asn Asn Thr
            580                 585                 590

Thr Pro Asp Asp Val Pro Ile Cys Glu Ala Tyr Leu Ala Phe Leu Glu
        595                 600                 605

Gly Asn Gly Asn Ile Gly Ala Tyr Trp Arg Val Leu Ser Asp Ala Gly
    610                 615                 620

Ile Thr Arg Gln Arg Leu Glu Gly Phe Asp Arg Ala Ile Thr Leu Glu
625                 630                 635                 640

Pro Glu Tyr Tyr Pro Glu Lys Arg Asp Ala Leu Ile Arg Asp Phe Arg
                645                 650                 655

Asn Tyr Leu Gly Ile Leu Lys Ala Val His Ser Gly Ala Asp Leu Ser
            660                 665                 670
```

```
Ala Ser Ala Ser Ala Ala Gly Asn Arg Ile Pro Gly Ser Cys Arg Gly
        675                 680                 685

Tyr Leu Gly Tyr Val Leu Ser His Val Gly Asp Ser Gln Ile Leu Pro
690                 695                 700

Leu Leu Glu Ala Cys Val Glu Ala Arg Thr Glu Leu Ala Leu Ser Gly
705                 710                 715                 720

Thr Leu Pro Gly Ser Arg Glu Leu Leu Tyr Leu Asp Leu Ala Leu Glu
                725                 730                 735

Asp Gln Ala Arg Gln Ala Ala Glu Arg Gly Val Gly Ala Ala Gly Phe
            740                 745                 750

Gly Ala Ala Ala Phe Met Arg Pro Leu Leu Gln Asn Leu Cys Leu Ser
        755                 760                 765

Leu Gly Asn Asn Glu Glu Leu Cys Tyr Cys Leu Lys Ala Trp Asn Glu
770                 775                 780

Leu Pro Gln Ser Val Arg Thr Gly Gly Arg Pro Asn Lys Glu Glu Ala
785                 790                 795                 800

Leu Leu Ala Val Ala Val Asn Arg Val Arg Arg Ala Leu Ala Asp
                805                 810                 815

Ile Ser Asp Arg Thr Val Asn Arg Ile Gly Asp Val Ser Ala Tyr
                820                 825                 830

Gly Arg Ala Phe Gly Val Glu His Trp Ala Tyr Glu Leu Phe Ala Glu
        835                 840                 845

Glu Val Ile Arg Gly Gly Pro Ala Phe Ala Val Ser Leu Val Ile Thr
850                 855                 860

Ala Ile Glu Pro Met Leu Arg Asn Ala Ala Ala Leu Gly Ala Trp Gln
865                 870                 875                 880

Val Ile Ser Pro Ile Ala Ala Thr Gly Arg Val Glu Val Ala Gly
                885                 890                 895

Leu His Glu Val Gln Asp Lys Thr Tyr Asp Thr Pro Thr Val Leu Ile
            900                 905                 910

Ala Glu Gln Val Thr Gly Glu Glu Ile Pro Glu Gly Cys Val Ala
            915                 920                 925

Val Ile Thr Pro Asp Ala Pro Asp Val Leu Ser His Val Ser Val Arg
930                 935                 940

Ala Arg Asn Met Arg Val Leu Phe Ala Thr Cys His Asp Asp Gly Pro
945                 950                 955                 960

Leu Lys Gln Leu Arg Glu Ala Lys Gly Lys Trp Leu His Phe Thr Pro
                965                 970                 975

Ser Ala Ser Gly Ala Val Ser Trp Asn Glu Thr Thr Ala Glu Ala Ala
            980                 985                 990

Gly Ala Ala Asp Asp Ser Ser His  Ser Thr Val Ser Lys  Pro Thr Lys
        995                 1000                1005

Gly Leu  Lys Ile Glu Val Pro  Asn Trp Cys Gly Arg  Trp Val Val
     1010                1015                1020

Gly Met  Asp Glu Tyr Lys Asp  Gly Val Val Gly Ala  Lys Ser Lys
     1025                1030                1035

Asn Leu  Ala Gly Leu Arg Gly  Arg Leu Pro Asp Asn  Ile Asn Leu
     1040                1045                1050

Pro Ala  Ser Val Thr Leu Pro  Phe Gly Cys Phe Glu  Gln Ala Leu
     1055                1060                1065

Glu Leu  Lys Glu Asn Gln Asp  Ile Lys Thr Lys Leu  Lys Lys His
     1070                1075                1080

Val Asp  Glu Val His Lys His  Ser Lys His His Ala  Asp His Thr
```

```
          1085                1090                1095

Thr Ser Asn Gly Thr Gly Pro Ser Pro Ala Ala Leu Leu Ala Glu
        1100                1105                1110

Cys Arg Lys Leu Ala Met Gln Val Val Pro Lys Gln Ile Arg
        1115                1120                1125

Asp Asp Leu Ala Gln Ala Met Lys Gly Ala Gly Ile Pro Pro Pro
        1130                1135                1140

Glu Thr Glu Glu Arg Trp Ala Leu Ala Leu Glu Ala Leu Arg Gly
        1145                1150                1155

Val Trp Ala Ser Lys Tyr Asn Asp Arg Ala Tyr Tyr Ser Leu Arg
        1160                1165                1170

Lys Ala Gly Leu Asp Phe Asp Ser Val Arg Met Ala Val Leu Val
        1175                1180                1185

Gln Arg Val Val Pro Ala Gln Tyr Ala Phe Val Ile His Thr Arg
        1190                1195                1200

Asn Pro Ser Asn Asn Asp Glu Arg Glu Val Phe Cys Glu Leu Val
        1205                1210                1215

Lys Gly Leu Gly Glu Ser Leu Val Ser Gly Met Val Pro Gly Ser
        1220                1225                1230

Ala Val Ala Phe Lys Ala Ala Lys Asp Glu Ala Gly Leu Gly Ser
        1235                1240                1245

Pro Glu Val Leu Cys Tyr Ala Ser Lys Ser Glu Ala Met Tyr Val
        1250                1255                1260

Arg Asp Ser Leu Ile Phe Arg Ser Asp Ser Asn Gly Glu Asp Leu
        1265                1270                1275

Glu Gly Tyr Ala Gly Ala Gly Leu Tyr Glu Ser Ile Thr Met Asp
        1280                1285                1290

Pro Ser Leu Leu Lys Lys Val Asp Tyr Met Glu Asp Arg Leu Val
        1295                1300                1305

Gln Asp Pro Ala Tyr Arg Arg Asp Leu Leu Ser Arg Ile Cys Arg
        1310                1315                1320

Leu Gly Ala Ser Ile Glu Gly Ala Leu Gly Thr Ala Gln Asp Ile
        1325                1330                1335

Glu Gly Val Val Ala Pro Asp Gly Ala Ile Thr Val Val Gln Thr
        1340                1345                1350

Arg Pro Gln Val
        1355

<210> SEQ ID NO 28
<211> LENGTH: 4074
<212> TYPE: DNA
<213> ORGANISM: Artificial Sequence
<220> FEATURE:
<223> OTHER INFORMATION: maize optimized
<220> FEATURE:
<221> NAME/KEY: misc_feature
<222> LOCATION: (1)..(4074)

<400> SEQUENCE: 28
atgggcatcg acgccgccgg cctggacacc aacggcaggg ccagggtggt gctgcacctg      60
gacggcgagg aggccagcga cttcctgaac ttcgtgctga aggacgacgc caccaacacc     120
tggtacgaca caacggcac caacttcaag gtggagctga gggccgacgc cagccccgag     180
gccccgaagc tggaccagct gccgaaggac ctgtgcgaca gtgggcctg ggtgaggtgg     240 gacttcgtgg caggccgca ggagagcgcc gaggccgccg ccagcgagta cgacaggggc     300
gtgagcgaga tgaaggagct gctggccagg ggcagggtgc tggacgagct gtggagggtg     360
```

```
gccgagggca agtggaagta cagcgactac aggaagaagg tggtgacccc gaccatcggc    420
gacggcaccg ccccgctgag cgcccagccg caggcccagc agccggccgg cgccccggcc    480
gccgccgccc tgccggccat cccggaggac ctgctgggcg tgcaggccta catcctggtg    540
atcaacgacc agctggccgc cggcagcagc ctggaggagg tggccggcag gctgaactac    600
accctgaagc agccgacccc gccggccagc accaggggca cccggccgg cagcagggcc    660 ggcagcgcca ccagcagcct ggacggcggc gccgccgccg ccccggccag gccgagcggc    720
ccgccgccgc aggtgggcgc cccgctgggc accccgaaga ggaacccgct ggacatgatc    780
aagaggaccg ccccgaacct gagcgccgag aggagcgtgg tggagaggcc gctggacttc    840
ctggtgcaga ggttcgccgt ggacccggcc accaagtgga ggaggacctt cccgctgggc    900
ggcaaggccg agatgctggt ggtggtgagg caggaggccg agaacaagcc gatcagggtg    960
gacctggtga ccgacaccgc cagcgacgtg gtgctgcact ggggcgtgag cccgatcggc   1020
agcagggagt gggtgatgcc ggacgacggc gtgctgccgg agggcagcat ggtgatgcac   1080
aaggccgtgg agaccccgtt cctgaactgc gacgacgacg agtgcgacgt ggagatcagc   1140
ggcgccaagg tgccgctgca gaggatcacc atcaacctgc cggccgacca ccacctgggc   1200
gccctgctgt tcgtgctgag gagcagcgac aacaccatgt ggtacaagga cgccggcggc   1260
aacttcaccg tgccgctgcc gagcaaggac aagccggtgg aggacaccag gagcatggac   1320
gtgatcaagg acgagctgag caggaccatc atcgaggccg aggtgaacag cagcatgtgg   1380
accctgatgc acaggttcaa caaggccgcc gacctggtga cgaggtgct gaacggctac   1440 tacgaccagc tggacgtggc cgacgccatg agcaggatct acgtgtggct gaggtacagc   1500
gccaccaggc acctgacctg gcagaggaac tacaacaccc agccgaggat cctgagcgcc   1560
gcccaggaga ggctgaccaa caccatcgcc aacgcccacg gcaggaccac cggcgaggcc   1620
caggagtggg tgaggatgat gctgaccacc gtgggcaggg gcggcgacgg ccagaagatc   1680
agggacgaga tcctgcacat catgcacagg aaccacatcc ggagaggaa gggcctgtgg   1740 atggaggagt ggcaccagaa gctgcacaac aacaccaccc cggacgacgt gccgatctgc   1800
gaggcctacc tggccttcct ggagggcaac ggcaacatcg gcgcctactg gagggtgctg   1860
agcgacgccg gcatcaccag gcagaggctg gagggcttcg acagggccat caccctggag   1920
ccggagtact acccggagaa gagggacgcc ctgatcaggg acttcaggaa ctacctgggc   1980
atcctgaagg ccgtgcacag cggcgccgac ctgagcgcca cgccagcgc cgccggcaac   2040 aggatcccgg gcagctgcag gggctacctg ggctacgtgc tgagccacgt gggcgacagc   2100
cagatcctgc cgctgctgga ggcctgcgtg gaggccagga ccgagctggc cctgagcggc   2160
accctgccgg gcagcaggga gctgctgtac ctggacctgg ccctggagga ccaggccagg   2220
caggccgccg agaggggcgt gggcgccgcc ggcttcggcg ccgccgcctt catgaggccg   2280
ctgctgcaga acctgtgcct gagcctgggc aacaacgagg agctgtgcta ctgcctgaag   2340
gcctggaacg agctgccgca gagcgtgagg accggcggca ggccgaacaa ggaggaggcc   2400
ctgctggccg tggccgtggt gaacagggtg aggagggccc tggccgacat cagcgacagg   2460
accgtgaaca ggatcggcga cgtgagcagc gcctacggca gggccttcgg cgtggagcac   2520
tgggcctacg agctgttcgc cgaggaggtg atcaggggcg gccggccttt cgccgtgagc   2580
ctggtgatca ccgccatcga gccgatgctg aggaacgccg ccgccctggg cgcctggcag   2640
gtgatcagcc cgatcgccgc caccggcagg gtggaggtgg tggccggcct gcacgaggtg   2700
caggacaaga cctacgacac cccgaccgtg ctgatcgccg agcaggtgac cggcgaggag   2760
```

```
gagatcccgg agggctgcgt ggccgtgatc accccggacg ccccggacgt gctgagccac    2820
gtgagcgtga gggccaggaa catgagggtg ctgttcgcca cctgccacga cgacggcccg    2880
ctgaagcagc tgagggaggc caagggcaag tggctgcact tcaccccgag cgccagcggc    2940
gccgtgagct ggaacgagac caccgccgag ccgccggcg ccgccgacga cagcagccac    3000
agcaccgtga gcaagccgac caagggcctg aagatcgagg tgccgaactg gtgcggcagg    3060
tgggtggtgg gcatggacga gtacaaggac ggcgtggtgg gcgccaagag caagaacctg    3120
gccggcctga ggggcaggct gccggacaac atcaacctgc cggccagcgt gaccctgccg    3180
ttcggctgct tcgagcaggc cctggagctg aaggagaacc aggacatcaa gaccaagctg    3240
aagaagcacg tggacgaggt gcacaagcac agcaagcacc acgccgacca caccaccagc    3300
aacggcaccg gcccgagccc ggccgccctg ctggccgagt gcaggaagct ggccatgcag    3360
gtggtggtgc cgaagcagat cagggacgac ctggcccagg ccatgaaggg cgccggcatc    3420
ccgccgccgg agaccgagga gaggtgggcc ctggccctgg aggccctgag gggcgtgtgg    3480
gccagcaagt acaacgacag ggcctactac agcctgagga aggccggcct ggacttcgac    3540
agcgtgagga tggccgtgct ggtgcagagg gtggtgccgg cccagtacgc cttcgtgatc    3600
cacaccagga acccgagcaa caacgacgag agggaggtgt tctgcgagct ggtgaagggc    3660
ctgggcgaga gcctggtgag cggcatggtg ccgggcagcg ccgtggcctt caaggccgcc    3720
aaggacgagg ccggcctggg cagcccggag gtgctgtgct acgccagcaa gagcgaggcc    3780
atgtacgtga gggacagcct gatcttcagg agcgacagca acggcgagga cctggagggc    3840
tacgccggcg ccggcctgta cgagagcatc accatggacc cgagcctgct gaagaaggtg    3900
gactacatgg aggacaggct ggtgcaggac ccggcctaca ggagggacct gctgagcagg    3960
atctgcaggc tgggcgccag catcgagggc ccctgggca ccgcccagga catcgagggc    4020
gtggtggccc cggacggcgc catcaccgtg gtgcagacca ggccgcaggt gtga          4074
```

<210> SEQ ID NO 29
<211> LENGTH: 4074
<212> TYPE: DNA
<213> ORGANISM: Artificial Sequence
<220> FEATURE:
<223> OTHER INFORMATION: mutated
<220> FEATURE:
<221> NAME/KEY: misc_feature
<222> LOCATION: (1)..(4074)

<400> SEQUENCE: 29

```
atgggcatcg acgccgccgg cctggacacc aacggcaggg ccagggtggt gctgcacctg      60
gacggcgagg aggccagcga cttcctgaac ttcgtgctga aggacgacgc caccaacacc     120
tggtacgaca caacggcac caacttcaag gtggagctga gggccgacgc cagcccgagc     180
gccccgaagc tggaccagct gccgaaggac ctgtgcgaca gtgggcctg ggtgaggtgg     240 gacttcgtgg gcaggccgca gaggagcgcc gaggccgccg ccagcgagta cgacggggc     300 gtgagcgaga tgaaggagct gctggccagg gcagggtgc tggacgagct gtggagggtg     360
gccgagggca agtggaagta cagcgactac aggaagaagg tggtgacccc gaccatcggc     420
gacggcaccg ccccgctgag cgcccagccg caggcccagc agccggccgg cgccccggcc     480
gccgccggcc tgccggccat cccggaggac ctgctgggcg tgcaggccta catcctggtg     540
atcaacgacc agctggccgg cggcagcagc ctggaggagg tggccggcag gctgaactac     600
accctgaagc agccgacccc gccggccagc accagggga ccccggccgg cagcagggcc     660
```

```
ggcagcgcca ccagcagcct ggacggcggc ggcgccgccg ccccggccag gccgagcggc    720
ccgccgccgc aggtgggcgc cccgctgggc accccgaaga ggaacccgct ggacatgatc    780
aagaggaccg ccccgaacct gagcgccgag aggagcgtgg tggagaggcc gctggacttc    840
ctggtgcaga ggttcgccgt ggacccgccc accaagtgga ggaggacctt cccgctgggc    900
ggcaaggccg agatgctggt ggtggtgagg caggaggccg agaacaagcc gatcagggtg    960
gacctggtga ccgacaccgc cagcgacgtg gtgctgcact ggggcgtgag cccgatcggc   1020
agcagggagt gggtgatgcc ggacgacggc gtgctgccgg agggcagcat ggtgatgcac   1080
aaggccgtgg agaccccgtt cctgaactgc gacgacgacg agtgcgacgt ggagatcagc   1140
ggcgccaagg tgccgctgca ggatcacc atcaacctgc cggccgacca ccacctgggc   1200
gccctgctgt tcgtgctgag gagcagcgac aacaccatgt ggtacaagga cgccggcggc   1260
aacttcaccg tgccgctgcc gagcaaggac aagccggtgg aggacaccag gagcatggac   1320
gtgatcaagg acgagctgag caggaccatc atcgaggccg aggtgaacag cagcatgtgg   1380
accctgatgc acaggttcaa caaggccgcc gacctggtga gcgaggtgct gaacggctac   1440
tacgaccagc tggacgtggc cgacgccatg agcaggatct acgtgtggct gaggtacagc   1500
gccaccaggc acctgacctg cagaggaac tacaacaccc agccgaggat cctgagcgcc   1560
gcccaggaga ggctgaccaa caccatcgcc aacgcccacg gcaggaccac cggcgaggcc   1620
caggagtggg tgaggatgat gctgaccacc gtgggcaggg gcggcgacgg ccagaagatc   1680
agggacgaga tcctgcacat catgcacagg aaccacatcc cggagaggaa gggcctgtgg   1740
atggaggagt ggcaccagaa gctgcacaac aacaccaccc cggacgacgt gccgatctgc   1800
gaggcctacc tggccttcct ggagggcaac ggcaacatcg cgccctactg gagggtgctg   1860
agcgacgccg gcatcaccag gcagaggctg gagggcttcg acagggccat caccctggag   1920
ccggagtact acccggagaa gagggacgcc ctgatcaggg acttcaggaa ctacctgggc   1980
atcctgaagg ccgtgcacag cggcgccgac ctgagcgcca cgccagcgc cggcggcaac   2040 aggatcccgg gcagctgcag gggctacctg gctacgtgc tgagccacgc cggcgacagc   2100
cagatcctgc cgctgctgga ggcctgcgtg gaggccagga ccgagctggc cctgagcggc   2160
accctgccgg gcagcaggga gctgctgtac ctggacctgg ccctggagga ccaggccagg   2220
caggccgccg agaggggcgt gggcgccgcc ggcttcggcg ccgccgcctt catgaggccg   2280
ctgctgcaga acctgtgcct gagcctgggc aacaacgagg agctgtgcta ctgcctgaag   2340
gcctggaacg agctgccgca gagcgtgagg accggcggca gccgaacaa ggaggaggcc   2400 ctgctggccg tggccgtggt gaacagggtg aggagggccc tggccgacat cagcgacagg   2460
accgtgaaca ggatcggcga cgtgagcagc gcctacggca gggccttcgg cgtggagcac   2520
tgggcctacg agctgttcgc cgaggaggtg atcaggggcg gccgggccct cgccgtgagc   2580
ctggtgatca ccgccatcga ccgatgctg aggaacgccg ccgccctggg cgcctggcag   2640
gtgatcagcc cgatcgccgc caccggcagg gtggaggtgg tggccggcct gcacgaggtg   2700
caggacaaga cctacgacac cccgaccgtg ctgatcgccg agcaggtgac cggcgaggag   2760
gagatcccgg agggctgcgt ggccgtgatc accccggacg ccccggacgt gctgagccac   2820
gtgagcgtga gggccaggaa catgagggtg ctgttcgcca cctgccacga cgacggcccg   2880
ctgaagcagc tgagggaggc caagggcaag tggctgcact tcaccccgag cgccagcggc   2940
gccgtgagct ggaacgagac caccgccgag ccgccggcg ccgccgacga cagcagccac   3000
agcaccgtga gcaagccgac caagggcctg aagatcgagg tgccgaactg gtgcggcagg   3060
```

-continued

```
tgggtggtgg gcatggacga gtacaaggac ggcgtggtgg gcgccaagag caagaacctg    3120
gccggcctga ggggcaggct gccggacaac atcaacctgc cggccagcgt gaccctgccg    3180
ttcggctgct tcgagcaggc cctggagctg aaggagaacc aggacatcaa gaccaagctg    3240
aagaagcacg tggacgaggt gcacaagcac agcaagcacc acgccgacca caccaccagc    3300
aacggcaccg gcccgagccc ggccgccctg ctggccgagt gcaggaagct ggccatgcag    3360
gtggtggtgc cgaagcagat cagggacgac ctggcccagg ccatgaaggg cgccggcatc    3420
ccgccgccgg agaccgagga gaggtgggcc ctggccctgg aggccctgag gggcgtgtgg    3480
gccagcaagt acaacgacag ggcctactac agcctgagga aggccggcct ggacttcgac    3540
agcgtgagga tggccgtgct ggtgcagagg gtggtgccgg cccagtacgc cttcgtgatc    3600
cacaccagga acccgagcaa caacgacgag agggaggtgt tctgcgagct ggtgaagggc    3660
ctgggcgaga gcctggtgag cggcatggtg ccgggcagcg ccgtggcctt caaggccgcc    3720
aaggacgagg ccggcctggg cagcccggag gtgctgtgct acgccagcaa gagcgaggcc    3780
atgtacgtga gggacagcct gatcttcagg agcgacagca cggcgagga cctggagggc    3840 tacgccggcg ccggcctgta cgagagcatc accatggacc cgagcctgct gaagaaggtg    3900
gactacatgg aggacaggct ggtgcaggac ccggcctaca ggagggacct gctgagcagg    3960
atctgcaggc tggcgccag catcgagggc gccctgggca ccgcccagga catcgagggc    4020
gtggtggccc cggacggcgc catcaccgtg gtgcagacca ggccgcaggt gtga           4074
```

<210> SEQ ID NO 30
<211> LENGTH: 1357
<212> TYPE: PRT
<213> ORGANISM: Artificial Sequence
<220> FEATURE:
<223> OTHER INFORMATION: mutated
<220> FEATURE:
<221> NAME/KEY: misc_feature
<222> LOCATION: (1)..(1357)

<400> SEQUENCE: 30

```
Met Gly Ile Asp Ala Ala Gly Leu Asp Thr Asn Gly Arg Ala Arg Val
1               5                   10                  15

Val Leu His Leu Asp Gly Glu Glu Ala Ser Asp Phe Leu Asn Phe Val
            20                  25                  30

Leu Lys Asp Asp Ala Thr Asn Thr Trp Tyr Asp Asn Asn Gly Thr Asn
        35                  40                  45

Phe Lys Val Glu Leu Arg Ala Asp Ala Ser Pro Ser Ala Pro Lys Leu
    50                  55                  60

Asp Gln Leu Pro Lys Asp Leu Cys Asp Lys Trp Ala Trp Val Arg Trp
65                  70                  75                  80

Asp Phe Val Gly Arg Pro Gln Arg Ser Ala Glu Ala Ala Ser Glu
                85                  90                  95

Tyr Asp Arg Gly Val Ser Glu Met Lys Glu Leu Leu Ala Arg Gly Arg
            100                 105                 110

Val Leu Asp Glu Leu Trp Arg Val Ala Glu Gly Lys Trp Lys Tyr Ser
        115                 120                 125

Asp Tyr Arg Lys Lys Val Val Thr Pro Thr Ile Gly Asp Gly Thr Ala
    130                 135                 140

Pro Leu Ser Ala Gln Pro Gln Ala Gln Gln Pro Gly Ala Pro Ala
145                 150                 155                 160

Ala Ala Gly Leu Pro Ala Ile Pro Glu Asp Leu Leu Gly Val Gln Ala
                165                 170                 175
```

-continued

```
Tyr Ile Leu Val Ile Asn Asp Gln Leu Ala Gly Gly Ser Ser Leu Glu
            180                 185                 190

Glu Val Ala Gly Arg Leu Asn Tyr Thr Leu Lys Gln Pro Thr Pro Pro
            195                 200                 205

Ala Ser Thr Arg Gly Thr Pro Ala Gly Ser Arg Ala Gly Ser Ala Thr
            210                 215                 220

Ser Ser Leu Asp Gly Gly Ala Ala Pro Ala Arg Pro Ser Gly
225                 230                 235                 240

Pro Pro Pro Gln Val Gly Ala Pro Leu Gly Thr Pro Lys Arg Asn Pro
                245                 250                 255

Leu Asp Met Ile Lys Arg Thr Ala Pro Asn Leu Ser Ala Glu Arg Ser
                260                 265                 270

Val Val Glu Arg Pro Leu Asp Phe Leu Val Gln Arg Phe Ala Val Asp
            275                 280                 285

Pro Ala Thr Lys Trp Arg Arg Thr Phe Pro Leu Gly Gly Lys Ala Glu
            290                 295                 300

Met Leu Val Val Arg Gln Glu Ala Glu Asn Lys Pro Ile Arg Val
305                 310                 315                 320

Asp Leu Val Thr Asp Thr Ala Ser Asp Val Leu His Trp Gly Val
                325                 330                 335

Ser Pro Ile Gly Ser Arg Glu Trp Val Met Pro Asp Asp Gly Val Leu
                340                 345                 350

Pro Glu Gly Ser Met Val Met His Lys Ala Val Glu Thr Pro Phe Leu
            355                 360                 365

Asn Cys Asp Asp Asp Glu Cys Asp Val Glu Ile Ser Gly Ala Lys Val
            370                 375                 380

Pro Leu Gln Arg Ile Thr Ile Asn Leu Pro Ala Asp His His Leu Gly
385                 390                 395                 400

Ala Leu Leu Phe Val Leu Arg Ser Ser Asp Asn Thr Met Trp Tyr Lys
                405                 410                 415

Asp Ala Gly Gly Asn Phe Thr Val Pro Leu Pro Ser Lys Asp Lys Pro
                420                 425                 430

Val Glu Asp Thr Arg Ser Met Asp Val Ile Lys Asp Glu Leu Ser Arg
            435                 440                 445

Thr Ile Ile Glu Ala Glu Val Asn Ser Ser Met Trp Thr Leu Met His
450                 455                 460

Arg Phe Asn Lys Ala Ala Asp Leu Val Ser Glu Val Leu Asn Gly Tyr
465                 470                 475                 480

Tyr Asp Gln Leu Asp Val Ala Asp Ala Met Ser Arg Ile Tyr Val Trp
                485                 490                 495

Leu Arg Tyr Ser Ala Thr Arg His Leu Thr Trp Gln Arg Asn Tyr Asn
            500                 505                 510

Thr Gln Pro Arg Ile Leu Ser Ala Ala Gln Glu Arg Leu Thr Asn Thr
            515                 520                 525

Ile Ala Asn Ala His Gly Arg Thr Gly Glu Ala Gln Glu Trp Val
530                 535                 540

Arg Met Met Leu Thr Thr Val Gly Arg Gly Gly Asp Gly Gln Lys Ile
545                 550                 555                 560

Arg Asp Glu Ile Leu His Ile Met His Arg Asn His Ile Pro Glu Arg
                565                 570                 575

Lys Gly Leu Trp Met Glu Glu Trp His Gln Lys Leu His Asn Asn Thr
                580                 585                 590

Thr Pro Asp Asp Val Pro Ile Cys Glu Ala Tyr Leu Ala Phe Leu Glu
            595                 600                 605
```

```
Gly Asn Gly Asn Ile Gly Ala Tyr Trp Arg Val Leu Ser Asp Ala Gly
    610                 615                 620
Ile Thr Arg Gln Arg Leu Glu Gly Phe Asp Arg Ala Ile Thr Leu Glu
625                 630                 635                 640
Pro Glu Tyr Tyr Pro Glu Lys Arg Asp Ala Leu Ile Arg Asp Phe Arg
                645                 650                 655
Asn Tyr Leu Gly Ile Leu Lys Ala Val His Ser Gly Ala Asp Leu Ser
            660                 665                 670
Ala Ser Ala Ser Ala Gly Gly Asn Arg Ile Pro Gly Ser Cys Arg Gly
        675                 680                 685
Tyr Leu Gly Tyr Val Leu Ser His Ala Gly Asp Ser Gln Ile Leu Pro
    690                 695                 700
Leu Leu Glu Ala Cys Val Glu Ala Arg Thr Glu Leu Ala Leu Ser Gly
705                 710                 715                 720
Thr Leu Pro Gly Ser Arg Glu Leu Leu Tyr Leu Asp Leu Ala Leu Glu
                725                 730                 735
Asp Gln Ala Arg Gln Ala Ala Glu Arg Gly Val Gly Ala Ala Gly Phe
            740                 745                 750
Gly Ala Ala Ala Phe Met Arg Pro Leu Leu Gln Asn Leu Cys Leu Ser
        755                 760                 765
Leu Gly Asn Asn Glu Glu Leu Cys Tyr Cys Leu Lys Ala Trp Asn Glu
    770                 775                 780
Leu Pro Gln Ser Val Arg Thr Gly Gly Arg Pro Asn Lys Glu Glu Ala
785                 790                 795                 800
Leu Leu Ala Val Ala Val Asn Arg Val Arg Arg Ala Leu Ala Asp
                805                 810                 815
Ile Ser Asp Arg Thr Val Asn Arg Ile Gly Asp Val Ser Ala Tyr
            820                 825                 830
Gly Arg Ala Phe Gly Val Glu His Trp Ala Tyr Glu Leu Phe Ala Glu
        835                 840                 845
Glu Val Ile Arg Gly Gly Pro Ala Phe Ala Val Ser Leu Val Ile Thr
    850                 855                 860
Ala Ile Glu Pro Met Leu Arg Asn Ala Ala Ala Leu Gly Ala Trp Gln
865                 870                 875                 880
Val Ile Ser Pro Ile Ala Ala Thr Gly Arg Val Glu Val Val Ala Gly
                885                 890                 895
Leu His Glu Val Gln Asp Lys Thr Tyr Asp Thr Pro Thr Val Leu Ile
            900                 905                 910
Ala Glu Gln Val Thr Gly Glu Glu Ile Pro Glu Gly Cys Val Ala
        915                 920                 925
Val Ile Thr Pro Asp Ala Pro Asp Val Leu Ser His Val Ser Val Arg
    930                 935                 940
Ala Arg Asn Met Arg Val Leu Phe Ala Thr Cys His Asp Asp Gly Pro
945                 950                 955                 960
Leu Lys Gln Leu Arg Glu Ala Lys Gly Lys Trp Leu His Phe Thr Pro
                965                 970                 975
Ser Ala Ser Gly Ala Val Ser Trp Asn Glu Thr Thr Ala Glu Ala Ala
            980                 985                 990
Gly Ala Ala Asp Asp Ser Ser His Ser Thr Val Ser Lys Pro Thr Lys
        995                 1000                1005
Gly Leu Lys Ile Glu Val Pro Asn Trp Cys Gly Arg Trp Val Val
    1010                1015                1020
Gly Met Asp Glu Tyr Lys Asp Gly Val Val Gly Ala Lys Ser Lys
```

|  |  |  |  |  |  |  |  |  |  |
|--|--|--|--|--|--|--|--|--|--|
| | 1025 | | | 1030 | | | 1035 | | |

Asn Leu Ala Gly Leu Arg Gly Arg Leu Pro Asp Asn Ile Asn Leu
1040                1045                1050

Pro Ala Ser Val Thr Leu Pro Phe Gly Cys Phe Glu Gln Ala Leu
1055                1060                1065

Glu Leu Lys Glu Asn Gln Asp Ile Lys Thr Lys Leu Lys Lys His
1070                1075                1080

Val Asp Glu Val His Lys His Ser Lys His Ala Asp His Thr
1085                1090                1095

Thr Ser Asn Gly Thr Gly Pro Ser Pro Ala Ala Leu Leu Ala Glu
1100                1105                1110

Cys Arg Lys Leu Ala Met Gln Val Val Pro Lys Gln Ile Arg
1115                1120                1125

Asp Asp Leu Ala Gln Ala Met Lys Gly Ala Gly Ile Pro Pro Pro
1130                1135                1140

Glu Thr Glu Glu Arg Trp Ala Leu Ala Leu Glu Ala Leu Arg Gly
1145                1150                1155

Val Trp Ala Ser Lys Tyr Asn Asp Arg Ala Tyr Tyr Ser Leu Arg
1160                1165                1170

Lys Ala Gly Leu Asp Phe Asp Ser Val Arg Met Ala Val Leu Val
1175                1180                1185

Gln Arg Val Val Pro Ala Gln Tyr Ala Phe Val Ile His Thr Arg
1190                1195                1200

Asn Pro Ser Asn Asn Asp Glu Arg Glu Val Phe Cys Glu Leu Val
1205                1210                1215

Lys Gly Leu Gly Glu Ser Leu Val Ser Gly Met Val Pro Gly Ser
1220                1225                1230

Ala Val Ala Phe Lys Ala Ala Lys Asp Glu Ala Gly Leu Gly Ser
1235                1240                1245

Pro Glu Val Leu Cys Tyr Ala Ser Lys Ser Glu Ala Met Tyr Val
1250                1255                1260

Arg Asp Ser Leu Ile Phe Arg Ser Asp Ser Asn Gly Glu Asp Leu
1265                1270                1275

Glu Gly Tyr Ala Gly Ala Gly Leu Tyr Glu Ser Ile Thr Met Asp
1280                1285                1290

Pro Ser Leu Leu Lys Lys Val Asp Tyr Met Glu Asp Arg Leu Val
1295                1300                1305

Gln Asp Pro Ala Tyr Arg Arg Asp Leu Leu Ser Arg Ile Cys Arg
1310                1315                1320

Leu Gly Ala Ser Ile Glu Gly Ala Leu Gly Thr Ala Gln Asp Ile
1325                1330                1335

Glu Gly Val Val Ala Pro Asp Gly Ala Ile Thr Val Val Gln Thr
1340                1345                1350

Arg Pro Gln Val
    1355

<210> SEQ ID NO 31
<211> LENGTH: 4409
<212> TYPE: DNA
<213> ORGANISM: Artificial Sequence
<220> FEATURE:
<223> OTHER INFORMATION: maize optimized
<220> FEATURE:
<221> NAME/KEY: misc_feature
<222> LOCATION: (1)..(4409)

<400> SEQUENCE: 31

```
ggatccacca tgggtaattc cctcggcaac aacctcctct accagggctt cctcacctcc     60
accgtgctcg agcacaagtc ccgcatctcc ccgccgtgcg tgggcggcaa ctccctcttc    120
cagcagcagg tgatctccaa gtccccgctc tccaccgagt tccgcggcaa ccgcctcaag    180
gtgcagaaga agaagatccc gatggagaag aagcgcgcct tctcctcctc cccgcacgcc    240
gtgctcacca ccgacacctc ctccgaactc gccgagaagt tctccctcgg cggcaacatc    300
gaactccagg tggacgtgcg cccgccgacc tccggcgacg tgtccttcgt ggacttccag    360
gtgaccaacg gctccgacaa gctcttcctc cactggggcg ccgtgaagtt cggcaaggag    420
acctggtccc tcccgaacga ccgcccggac ggcaccaagg tgtacaagaa caaggccctc    480
cgcaccccgt tcgtgaagtc cggctccaac tccatcctcc gcctcgagat ccgcgacacc    540
gccatcgagg ccatcgagtt cctcatctac gacgaggccc acgacaagtg gatcaagaac    600
aacggcggca acttccgcgt gaagctctcc cgcaaggaga tccgcggccc ggacgtgtcc    660
gtgccggagg aactcgtgca gatccagtcc tacctccgct gggagcgcaa gggcaagcag    720
aactacccgc cggagaagga gaaggaggag tacgaggctg ctcgcaccgt gctccaggag    780
gagatcgctc gcggtgcctc catccaggac atccgcgccc gctcaccaa gaccaacgac    840
aagtcccagt ccaaggagga gccgctccac gtgaccaagt ccgacatccc ggacgacctc    900
gcccaggccc aggcctacat ccgctgggag aaggccggca agccgaacta cccgccggag    960
aagcagatcg aggaactcga ggaggcccgc cgcgaactcc agctcgaact cgagaagggc   1020
atcaccctcg acgaactccg caagaccatc accaagggcg agatcaagac caaggtggag   1080
aagcacctca gcgctcctc cttcgccgtg gagcgcatcc agcgcaagaa gcgcgacttc   1140
ggccacctca tcaacaagta cacctcctcc cctgccgtgc aggtgcagaa ggtgctcgag   1200
gagccaccag ccctctccaa gatcaagctc tacgccaagg agaaggagga gcagatcgac   1260
gacccgatcc tcaacaagaa gatcttcaag gtggacgacg cgaactcct cgtgctcgtg   1320
gccaagtcct ccggcaagac caaggtgcac ctcgccaccg acctcaacca gccgatcacc   1380
ctccactggg ccctctccaa gtccccgggc gagtggatgg tgccgccgtc ctccatcctc   1440
ccgccgggct ccatcatcct cgacaaggcc gccgagaccc cgttctccgc ctcctcctcc   1500
gacggcctca cctccaaggt gcagtccctc gacatcgtga tcgaggacgg caacttcgtg   1560
ggcatgccgt tcgtgctcct ctccggcgag aagtggatca agaaccaggg ctccgacttc   1620
tacgtgggct tctccgccgc ctccaagctc gccctcaagg ctgctggcga cggctccggc   1680
accgccaagt ccctcctcga caagatcgcc gacatggagt ccgaggccca gaagtccttc   1740
atgcaccgct tcaacatcgc cgccgacctc atcgaggacg ccacctccgc cggcgaactc   1800
ggcttcgccg gcatcctcgt gtggatgcgc ttcatggcca cccgccagct catctggaac   1860
aagaactaca cgtgaagcc gcgcgagatc tccaaggccc aggaccgcct caccgacctc   1920
ctccagaacg ccttcacctc ccacccgcag taccgcgaga tcctccgcat gatcatgtcc   1980
accgtgggtc gcggtggcga gggcgacgtg ggccagcgca tccgcgacga gatcctcgtg   2040
atccagcgca acaacgactg caagggcggc atgatgcagg agtggcacca gaagctccac   2100
aacaacacct ccccggacga cgtggtgatc tgccaggccc tcatcgacta catcaagtcc   2160
gacttcgacc tcgcgtgta ctggaagacc ctcaacgaga acggcatcac caaggagcgc   2220
ctcctctcct acgaccgcgc catccactcc gagccgaact ccgcggcga ccagaagggc   2280
ggcctcctcc gcgacctcgg ccactacatg cgcaccctca ggccgtgca ctccggcgcc   2340
gacctcgagt ccgccatcgc caactgcatg ggctacaaga ccgagggcga gggcttcatg   2400
```

```
gtgggcgtgc agatcaaccc ggtgtccggc ctcccgtccg gcttccagga cctcctccac    2460
ttcgtgctcg accacgtgga ggacaagaac gtggagaccc tcctcgagcg cctcctcgag    2520
gcccgcgagg aactccgccc gctcctcctc aagccgaaca accgcctcaa ggacctcctc    2580
ttcctcgaca tcgccctcga ctccaccgtg cgcaccgccg tggagcgcgg ctacgaggaa    2640
ctcaacaacg ccaacccgga gaagatcatg tacttcatct ccctcgtgct cgagaacctc    2700
gccctctccg tggacgacaa cgaggacctc gtgtactgcc tcaagggctg gaaccaggcc    2760
ctctccatgt ccaacggcgg cgacaaccac tgggccctct tcgccaaggc cgtgctcgac    2820
cgcacccgcc tcgccctcgc ctccaaggcc gagtggtatc accacctcct ccagccgtcc    2880
gccgagtacc tcggctccat cctcggcgtg accagtgggc cctcaacat cttcaccgag    2940 gagatcatcc gcgccggctc cgccgcctcc ctctcctccc cctcaaccg cctcgacccg    3000 gtgctccgca agaccgccaa cctcggctcc tggcagatca tctccccggt ggaggccgtg    3060
ggctacgtgg tggtggtgga cgaactcctc tccgtgcaga cgagatcta cgagaagccg    3120 accatcctcg tggccaagtc cgtgaagggc gaggaggaga tcccgacgg cgccgtggcc    3180 ctcatcaccc cggacatgcc ggacgtgctc tcccacgtgt ccgtgcgcgc ccgcaacggc    3240
aaggtgtgct cgccaccctg cttcgacccg aacatcctcg ccgacctcca ggccaaggag    3300
ggccgcatcc tcctcctcaa gccgaccccg tccgacatca tctactccga ggtgaacgag    3360
atcgaactcc agtcctcctc caacctcgtg gaggccgaga cctccgccac cctccgcctc    3420
gtgaagaagc agttcggcgg ctgctacgcc atctccgccg acgagttcac ctccgagatg    3480
gtgggcgcca gtcccgcaa catcgcctac ctcaagggca aggtgccgtc ctccgtgggc    3540
atcccgacct ccgtggccct cccgttcggc gtgttcgaga aggtgctctc cgacgacatc    3600
aaccagggcg tggccaagga actccagatc ctcatgaaga agctctccga gggcgacttc    3660
tccgccctcg gcgagatccg caccaccgtg ctcgacctct ccgcccccggc ccagctcgtg    3720 aaggaactca aggagaagat gcagggctcc ggcatgccgt ggccgggcga cgagggcccg    3780
aagcgctggg agcaggcctg gatggccatc aagaaggtgt gggcctccaa gtggaacgag    3840
cgcgcctact tctccacccg caaggtgaag ctcgaccacg actacctctg catggccgtg    3900
ctcgtgcagg agatcatcaa cgccgactac gccttcgtga tccacaccac caacccgtcc    3960
tccggcgacg actccgagat ctacgccgag gtggtgcgcg cctcggcga cccctcgtg    4020 ggagcctacc caggacgcgc actctccttc atctgcaaga agaaggacct caactccccg    4080
caggtgctcg gctaccgtc caagccgatc ggcctcttca tcaagcgctc catcatcttc    4140
cgctccgact ccaacggcga ggacctcgag ggctacgccg cgccggcct ctacgactcc    4200 gtgccgatgg acgaggagga gaaggtggtg atcgactact cctccgaccc gctcatcacc    4260
gacggcaact tccgccagac catcctctcc aacatcgccc gcgccggcca cgccatcgag    4320
gaactctacg gctccccgca ggacatcgag ggcgtggtgc gcgacggcaa gatctacgtg    4380
gtgcagaccc gcccgcagat gtagagctc                                     4409
```

CHLAMYDOMONAS GLUCAN DIKINASE GENE, ENZYME AND MODIFIED STARCH, USES, METHODS FOR PRODUCTION THEREOF

SUMMARY OF THE INVENTION

The present invention relates the nucleotide sequence from *Chlamydomonas reinhardtii* encoding a glucan dikinase enzyme and to methods of use; to modified starch, as well as production and uses thereof. The starch has modified properties of viscosity and a modified phosphate content.

BACKGROUND OF THE INVENTION

This invention describes the glucan dikinase enzyme and gene sequence from *Chlamydomonas reinhardtii*. Although glucan dikinase enzyme activity has been previously described in higher plants, there was no report describing this enzyme in microorganisms in this case a single-celled green alga. Comparison of the gene sequence of this enzyme from *Chlamydomonas reinhardtii* to that of higher plants also shows that the genes are distantly related with low sequence homology, both at the nucleic acid and at the amino acid level.

Other phosphorylating enzymes, such as the R1 gene from potato, have been cloned as described in WO 94/28146 and U.S. Pat. No. 6,596,928, and the production of modified starch is described in WO2005/002359A2 and U.S. Pat. No. 6,734,340.

BRIEF DESCRIPTION OF THE FIGURES

FIG. 10 shows the starch phosphorylation level of T1 seed expressing synthetic R1 (codon-optimized).

DETAILED DESCRIPTION OF THE INVENTION

Figure 1:
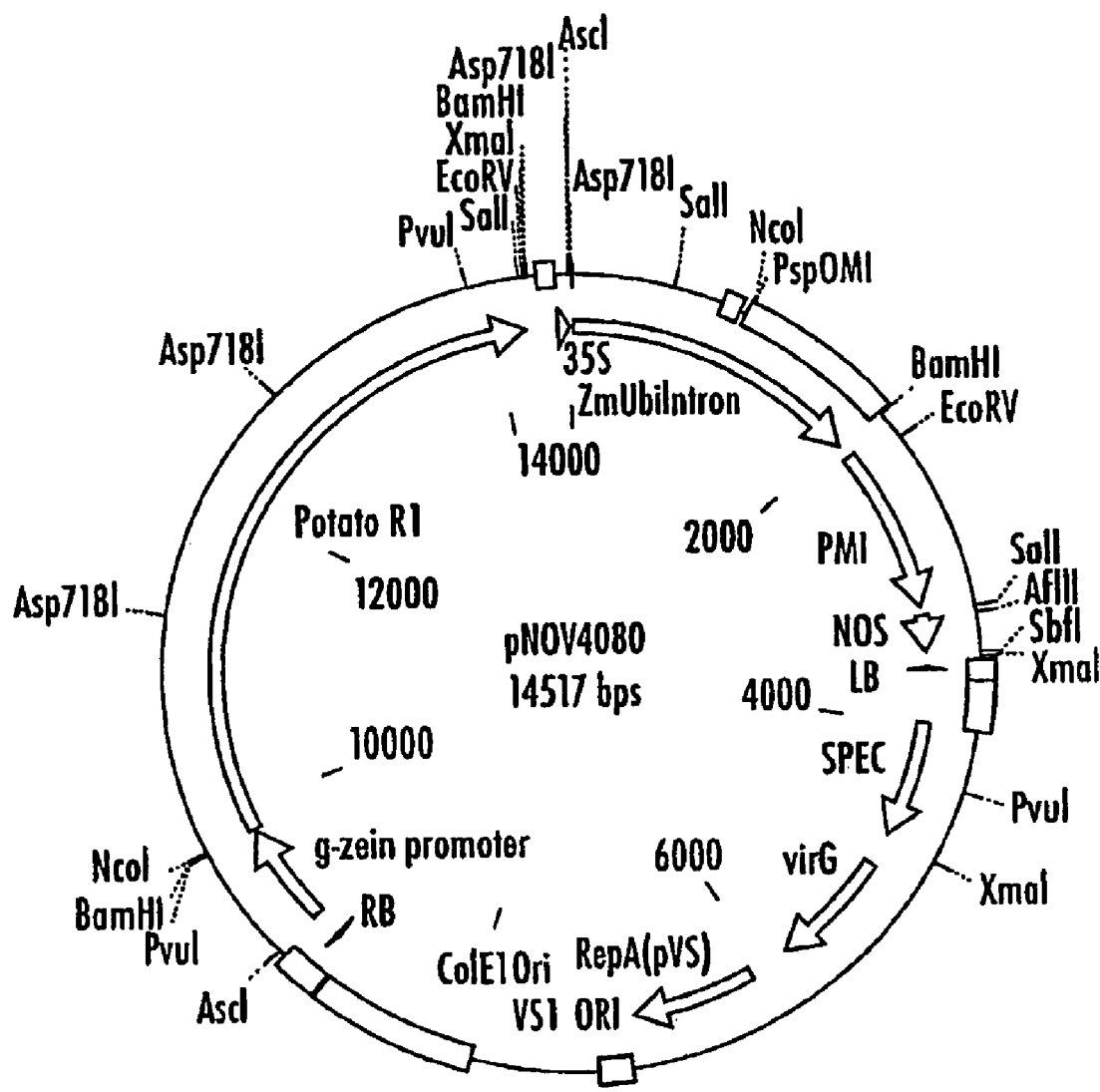
FIG. 1 depicts an *Agrobacterium*-vector containing a PCR-amplified potato-R1 as insert.

The protein encoded by the nucleic acid molecules of the invention is a glucan dikinase gene isolated from *Chlamydomonas reinhardtii*. The coding region is a nucleotide sequence of 4076 bp isolated from the *Chlamydomonas reinhardtii* genome by PCR from cDNA and was expressed in *E. coli*. A higher level of phosphorylation, due to in vivo phosphorylation-expression of dikinase activity) was observed in the glycogen isolated from the *E. coli* expressing the protein product of the gene when compared to the glycogen from *E. coli* with the vector only. Secondly, in vitro assays showed that the gene product behaves as a glucan dikinase capable of phosphorylating (in vitro) amylopectin and glycogen.

The protein encoded by the nucleic acid molecules described herein is an glucan dikinase protein which influences starch synthesis and/or modification. It was found that changes in the amount of the protein in plant cells can lead to changes in the starch metabolism of the plant, and in particular to the synthesis of starch with modified physical and chemical properties.

Using the nucleic acid molecules encoding glucan dikinase protein can allow production of transgenic plants, by means of recombinant DNA techniques synthesizing a modified starch that differs from the starch synthesized in wild-type plants with respect to its structure and its physical and chemical properties. To achieve this, the nucleic acid molecules encoding glucan dikinase protein can be linked to regulatory elements, which ensure transcription and translation in plant cells, and is then introduced into plant cells. The nucleic acid molecule of the invention is preferably a maize optimized nucleic acid sequence, such as the sequence, provided below.

The polynucleotide encoding the processing enzyme is preferably modified to include codons that are optimized for expression in a selected organism such as a plant (see, e.g., Wada et al., *Nucl. Acids Res.*, 18:2367 (1990), Murray et al., *Nucl. Acids Res.*, 17:477 (1989), U.S. Pat. Nos. 5,096,825, 5,625,136, 5,670,356 and 5,874,304). Codon optimized sequences are synthetic sequences, i.e., they do not occur in nature, and preferably encode the identical polypeptide (or an enzymatically active fragment of a full length polypeptide which has substantially the same activity as the full length polypeptide) encoded by the non-codon optimized parent polynucleotide which encodes a processing enzyme.

Therefore, the present invention can use transgenic plant cells containing a nucleic acid molecule encoding glucan dikinase protein whereby the nucleic acid molecule is linked to a regulatory elements that ensure the transcription in plant cells. The regulatory elements are preferably heterologous with respect to the nucleic acid molecule.

Controlling Gene Expression in Transgenic Plants

The invention further relates to transformed cells comprising the nucleic acid molecules, transformed plants, seeds, and plant parts, and methods of modifying phenotypic traits of interest by altering the expression of the genes of the invention.

A. Modification of Coding Sequences and Adjacent Sequences

The transgenic expression in plants of genes derived from heterologous sources may involve the modification of those genes to achieve and optimize their expression in plants. In particular, bacterial ORFs which encode separate enzymes but which are encoded by the same transcript in the native microbe are best expressed in plants on separate transcripts. To achieve this, each microbial ORF is isolated individually and cloned within a cassette which provides a plant promoter sequence at the 5' end of the ORE and a plant transcriptional terminator at the 3' end of the ORF. The isolated ORF sequence preferably includes the initiating ATG codon and the terminating STOP codon but may include additional sequence beyond the initiating ATG and the STOP codon. In addition, the ORF may be truncated, but still retain the required activity; for particularly long ORFs, truncated versions which retain activity may be preferable for expression in transgenic organisms. By "plant promoter" and "plant transcriptional terminator" it is intended to mean promoters and transcriptional terminators which operate within plant cells. This includes promoters and transcription terminators which may be derived from non-plant sources such as viruses (an example is the Cauliflower Mosaic Virus).

In some cases, modification to the ORF coding sequences and adjacent sequence is not required. It is sufficient to isolate a fragment containing the ORF of interest and to insert it downstream of a plant promoter. For example, Gaffney et al. (*Science* 261: 754-756 (1993)) have expressed the *Pseudomonas* nahG gene in transgenic plants under the control of the CaMV 35S promoter and the CaMV tml terminator successfully without modification of the coding sequence and with nucleotides of the *Pseudomonas* gene upstream of the ATG still attached, and nucleotides downstream of the STOP codon still attached to the nahG ORF. Preferably as little adjacent microbial sequence should be left attached upstream of the ATG and downstream of the STOP codon. In practice, such construction may depend on the availability of restriction sites.

In other cases, the expression of genes derived from microbial sources may provide problems in expression. These problems have been well characterized in the art and are particularly common with genes derived from certain sources such as *Bacillus*. These problems may apply to the nucleotide sequence of this invention and the modification of these genes can be undertaken using techniques now well known in the art. The following problems may be encountered:

1. Codon Usage.

The preferred codon usage in plants differs from the preferred codon usage in certain microorganisms. Comparison of the usage of codons within a cloned microbial ORF to usage in plant genes (and in particular genes from the target plant) will enable an identification of the codons within the ORF which should preferably be changed. Typically plant evolution has tended towards a strong preference of the nucleotides C and G in the third base position of monocotyledons, whereas dicotyledons often use the nucleotides A or T at this position. By modifying a gene to incorporate preferred codon usage for a particular target transgenic species, many of the problems described below for GC/AT content and illegitimate splicing will be overcome.

2. GC/AT Content.

Plant genes typically have a GC content of more than 35%. ORF sequences which are rich in A and T nucleotides can cause several problems in plants. Firstly, motifs of ATTTA are believed to cause destabilization of messages and are found at the 3' end of many short-lived mRNAs. Secondly, the occurrence of polyadenylation signals such as AATAAA at inappropriate positions within the message is believed to cause premature truncation of transcription. In addition, monocotyledons may recognize AT-rich sequences as splice sites (see below).

3. Sequences Adjacent to the Initiating Methionine.

Plants differ from microorganisms in that their messages do not possess a defined ribosome binding site. Rather, it is believed that ribosomes attach to the 5' end of the message and scan for the first available ATG at which to start translation. Nevertheless, it is believed that there is a preference for certain nucleotides adjacent to the ATG and that expression of microbial genes can be enhanced by the inclusion of a eukaryotic consensus translation initiator at the ATG. Clontech (1993/1994 catalog, page 210, incorporated herein by reference) have suggested one sequence as a consensus translation initiator for the expression of the *E. coli* uidA gene in plants. Further, Joshi (*N.A.R.* 15: 6643-6653 (1987), incorporated herein by reference) has compared many plant sequences adjacent to the ATG and suggests another consensus sequence. In situations where difficulties are encountered in the expression of microbial ORFs in plants, inclusion of one of these sequences at the initiating ATG may improve translation. In such cases the last three nucleotides of the consensus may not be appropriate for inclusion in the modified sequence due to their modification of the second AA residue. Preferred sequences adjacent to the initiating methionine may differ between different plant species. A survey of 14 maize genes located in the GenBank database provided the following results:

Position Before the Initiating ATG in 14 Maize Genes

|   | −10 | −9 | −8 | −7 | −6 | −5 | −4 | −3 | −2 | −1 |
|---|-----|----|----|----|----|----|----|----|----|----|
| C | 3 | 8 | 4 | 6 | 2 | 5 | 6 | 0 | 10 | 7 |
| T | 3 | 0 | 3 | 4 | 3 | 2 | 1 | 1 | 1 | 0 |
| A | 2 | 3 | 1 | 4 | 3 | 2 | 3 | 7 | 2 | 3 |
| G | 6 | 3 | 6 | 0 | 6 | 5 | 4 | 6 | 1 | 5 |

This analysis can be done for the desired plant species into which the nucleotide sequence is being incorporated, and the sequence adjacent to the ATG modified to incorporate the preferred nucleotides.

4. Removal of Illegitimate Splice Sites.

Genes cloned from non-plant sources and not optimized for expression in plants may also contain motifs which may be recognized in plants as 5' or 3' splice sites, and be cleaved, thus generating truncated or deleted messages. These sites can be removed using the techniques well known in the art.

Techniques for the modification of coding sequences and adjacent sequences are well known in the art. In cases where the initial expression of a microbial ORF is low and it is deemed appropriate to make alterations to the sequence as described above, then the construction of synthetic genes can be accomplished according to methods well known in the art. These are, for example, described in the published patent disclosures EP 0 385 962 (to Monsanto), EP 0 359 472 (to Lubrizol) and WO 93/07278 (to Ciba-Geigy), all of which are incorporated herein by reference. In most cases it is preferable to assay the expression of gene constructions using transient assay protocols (which are well known in the art) prior to their transfer to transgenic plants.

B. Construction of Plant Expression Cassettes

Coding sequences intended for expression in transgenic plants are first assembled in expression cassettes behind a suitable promoter expressible in plants. The expression cassettes may also comprise any further sequences required or selected for the expression of the transgene. Such sequences include, but are not restricted to, transcription terminators, extraneous sequences to enhance expression such as introns, vital sequences, and sequences intended for the targeting of the gene product to specific organelles and cell compartments. These expression cassettes can then be easily transferred to the plant transformation vectors described below. The following is a description of various components of typical expression cassettes.

1. Promoters

The selection of the promoter used in expression cassettes will determine the spatial and temporal expression pattern of the transgene in the transgenic plant. Selected promoters will express transgenes in specific cell types (such as leaf epidermal cells, mesophyll cells, root cortex cells) or in specific tissues or organs (roots, leaves or flowers, for example) and the selection will reflect the desired location of accumulation of the gene product. Alternatively, the selected promoter may drive expression of the gene under various inducing conditions. Promoters vary in their strength, i.e., ability to promote transcription. Depending upon the host cell system utilized, any one of a number of suitable promoters can be used, including the gene's native promoter. The following are non-limiting examples of promoters that may be used in expression cassettes.

a. Constitutive Expression, the Ubiquitin Promoter:

Ubiquitin is a gene product known to accumulate in many cell types and its promoter has been cloned from several species for use in transgenic plants (e.g. sunflower—Binet et al. Plant Science 79: 87-94 (1991); maize—Christensen et al. Plant Molec. Biol. 12: 619-632 (1989); and *Arabidopsis*—Callis et al., *J. Biol. Chem.* 265:12486-12493 (1990) and Norris et al., *Plant Mol. Biol.* 21:895-906 (1993)). The maize ubiquitin promoter has been developed in transgenic monocot systems and its sequence and vectors constructed for monocot transformation are disclosed in the patent publication EP 0 342 926 (to Lubrizol) which is herein incorporated by reference. Taylor et al. (Plant Cell Rep. 12: 491-495 (1993)) describe a vector (pAHC25) that comprises the maize ubiquitin promoter and first intron and its high activity in cell suspensions of numerous monocotyledons when introduced via microprojectile bombardment. The *Arabidopsis* ubiquitin promoter is ideal for use with the nucleotide sequences of the present invention. The ubiquitin promoter is suitable for gene expression in transgenic plants, both monocotyledons and dicotyledons. Suitable vectors are derivatives of pAHC25 or any of the transformation vectors described in this application, modified by the introduction of the appropriate ubiquitin promoter and/or intron sequences.

b. Constitutive Expression, the CaMV 35S Promoter:

Construction of the plasmid pCGN1761 is described in the published patent application EP 0 392 225 (Example 23), which is hereby incorporated by reference. pCGN1761 contains the "double" CaMV 35S promoter and the tml transcriptional terminator with a unique EcoRI site between the promoter and the terminator and has a pUC-type backbone. A derivative of pCGN1761 is constructed which has a modified polylinker which includes NotI and XhoI sites in addition to the existing EcoRI site. This derivative is designated pCGN1761ENX. pCGN1761ENX is useful for the cloning of cDNA sequences or coding sequences (including microbial ORF sequences) within its polylinker for the purpose of their expression under the control of the 35S promoter in transgenic plants. The entire 35S promoter-coding sequence-tml terminator cassette of such a construction can be excised by HindIII, SphI, SalI, and xbaI sites 5' to the promoter and XbaI, BamHI and BglI sites 3' to the terminator for transfer to transformation vectors such as those described below. Furthermore, the double 35S promoter fragment can be removed by 5' excision with HindIII, SphI, SalI, XbaI, or PstI, and 3' excision with any of the polylinker restriction sites (EcoRI, NotI or XhoI) for replacement with another promoter. If desired, modifications around the cloning sites can be made by the introduction of sequences that may enhance translation. This is particularly useful when overexpression is desired. For example, pCGN1761ENX may be modified by optimization of the translational initiation site as described in Example 37 of U.S. Pat. No. 5,639,949, incorporated herein by reference.

c. Constitutive Expression, the Actin Promoter:

Several isoforms of actin are known to be expressed in most cell types and consequently the actin promoter is a good choice for a constitutive promoter. In particular, the promoter from the rice ActI gene has been cloned and characterized (McElroy et al. Plant Cell 2: 163-171 (1990)). A 1.3 kb fragment of the promoter was found to contain all the regulatory elements required for expression in rice protoplasts. Furthermore, numerous expression vectors based on the ActI promoter have been constructed specifically for use in monocotyledons (McElroy et al. Mol. Gen. Genet. 231: 150-160 (1991)). These incorporate the ActI-intron 1, AdhI 5' flanking sequence and AdhI-intron 1 (from the maize alcohol dehydrogenase gene) and sequence from the CaMV 35S promoter. Vectors showing highest expression were fusions of 35S and ActI intron or the ActI 5' flanking sequence and the ActI intron. Optimization of sequences around the initiating ATG (of the GUS reporter gene) also enhanced expression. The promoter expression cassettes described by McElroy et al. (Mol. Gen. Genet. 231: 150-160 (1991)) can be easily modified for gene expression and are particularly suitable for use in monocotyledonous hosts. For example, promoter-containing fragments is removed from the McElroy constructions and used to replace the double 35S promoter in pCGN1761ENX, which is then available for the insertion of specific gene sequences. The fusion genes thus constructed can then be transferred to appropriate transformation vectors. In a separate report, the rice ActI promoter with its first intron has also been found to direct high expression in cultured barley cells (Chibbar et al. Plant Cell Rep. 12: 506-509 (1993)).

d. Inducible Expression, PR-1 Promoters:

The double 35S promoter in pCGN1761ENX may be replaced with any other promoter of choice that will result in suitably high expression levels. By way of example, one of the chemically regulatable promoters described in U.S. Pat. No. 5,614,395, such as the tobacco PR-1a promoter, may replace the double 35S promoter. Alternately, the *Arabidopsis* PR-1 promoter described in Lebel et al., *Plant J.* 16:223-233 (1998) may be used. The promoter of choice is preferably excised from its source by restriction enzymes, but can alternatively be PCR-amplified using primers that carry appropriate terminal restriction sites. Should PCR-amplification be undertaken, then the promoter should be re-sequenced to check for amplification errors after the cloning of the amplified promoter in the target vector. The chemically/pathogen regulatable tobacco PR-1a promoter is cleaved from plasmid pCIB1004 (for construction, see example 21 of EP 0 332 104, which is hereby incorporated by reference) and transferred to plasmid pCGN1761 ENX (Uknes et al., *Plant Cell* 4: 645-656 (1992)). pCIB1004 is cleaved with NcoI and the resultant 3' overhang of the linearized fragment is rendered blunt by treatment with T4 DNA polymerase. The fragment is then cleaved with HindIII and the resultant PR-1a promoter-containing fragment is gel purified and cloned into pCGN1761ENX from which the double 35S promoter has been removed. This is done by cleavage with XhoI and blunting with T4 polymerase, followed by cleavage with HindIII and isolation of the larger vector-terminator containing fragment into which the pCIB1004 promoter fragment is cloned. This generates a pCGN1761ENX derivative with the PR-1a promoter and the tml terminator and an intervening polylinker with unique EcoRI and NotI sites. The selected coding sequence can be inserted into this vector, and the fusion products (i.e. promoter-gene-terminator) can subsequently be transferred to any selected transformation vector, including those described infra. Various chemical regulators may be employed to induce expression of the selected coding sequence in the plants transformed according to the present invention, including the benzothiadiazole, isonicotinic acid, and salicylic acid compounds disclosed in U.S. Pat. Nos. 5,523,311 and 5,614,395.

e. Inducible Expression, an Ethanol-Inducible Promoter:

A promoter inducible by certain alcohols or ketones, such as ethanol, may also be used to confer inducible expression of a coding sequence of the present invention. Such a promoter is for example the alcA gene promoter from *Aspergillus nidulans* (Caddick et al. (1998) *Nat. Biotechnol* 16:177-180). In *A. nidulans*, the alcA gene encodes alcohol dehydrogenase I, the expression of which is regulated by the AlcR transcription factors in presence of the chemical inducer. For the purposes of the present invention, the CAT coding sequences in plasmid palcA:CAT comprising a alcA gene promoter sequence fused to a minimal 35S promoter (Caddick et al. (1998) *Nat. Biotechnol* 16:177-180) are replaced by a coding sequence of the present invention to form an expression cassette having the coding sequence under the control of the alcA gene promoter. This is carried out using methods well known in the art.

f. Inducible Expression, a Glucocorticoid-Inducible Promoter:

Induction of expression of a nucleic acid sequence of the present invention using systems based on steroid hormones is also contemplated. For example, a glucocorticoid-mediated induction system is used (Aoyama and Chua (1997) *The Plant Journal* 11: 605-612) and gene expression is induced by application of a glucocorticoid, for example a synthetic glucocorticoid, preferably dexamethasone, preferably at a concentration ranging from 0.1 mM to 1 mM, more preferably from 10 mM to 100 mM. For the purposes of the present invention, the luciferase gene sequences are replaced by a nucleic acid sequence of the invention to form an expression cassette having a nucleic acid sequence of the invention under the control of six copies of the GAL4 upstream activating sequences fused to the 35S minimal promoter. This is carried out using methods well known in the art. The trans-acting factor comprises the GAL4 DNA-binding domain (Keegan et al. (1986) *Science* 231: 699-704) fused to the transactivating domain of the herpes viral protein VP16 (Triezenberg et al. (1988) *Genes Devel.* 2: 718-729) fused to the hormone-binding domain of the rat glucocorticoid receptor (Picard et al. (1988) *Cell* 54: 1073-1080). The expression of the fusion protein is controlled by any promoter suitable for expression in plants known in the art or described here. This expression cassette is also comprised in the plant comprising a nucleic acid sequence of the invention fused to the 6×GAL4/minimal promoter. Thus, tissue- or organ-specificity of the fusion protein is achieved leading to inducible tissue- or organ-specificity of the insecticidal toxin.

g. Root Specific Expression:

Another pattern of gene expression is root expression. A suitable root promoter is the promoter of the maize metallothionein-like (MTL) gene described by de Framond (FEBS 290: 103-106 (1991)) and also in U.S. Pat. No. 5,466,785, incorporated herein by reference. This "MTL" promoter is transferred to a suitable vector such as pCGN1761ENX for the insertion of a selected gene and subsequent transfer of the entire promoter-gene-terminator cassette to a transformation vector of interest.

h. Wound-Inducible Promoters:

Wound-inducible promoters may also be suitable for gene expression. Numerous such promoters have been described (e.g. Xu et al. Plant Molec. Biol. 22: 573-588 (1993), Logemann et al. Plant Cell 1: 151-158 (1989), Rohrmeier & Lehle, Plant Molec. Biol. 22: 783-792 (1993), Firek et al. Plant Molec. Biol. 22: 129-142 (1993), Warner et al. Plant J. 3: 191-201 (1993)) and all are suitable for use with the instant invention. Logemann et al. describe the 5' upstream sequences of the dicotyledonous potato wunI gene. Xu et al. show that a wound-inducible promoter from the dicotyledon potato (pin2) is active in the monocotyledon rice. Further, Rohrmeier & Lehle describe the cloning of the maize WipI cDNA which is wound induced and which can be used to isolate the cognate promoter using standard techniques. Similar, Firek et al. and Warner et al. have described a wound-induced gene from the monocotyledon *Asparagus officinalis*, which is expressed at local wound and pathogen invasion sites. Using cloning techniques well known in the art, these promoters can be transferred to suitable vectors, fused to the genes pertaining to this invention, and used to express these genes at the sites of plant wounding.

i. Pith-Preferred Expression:

Patent Application WO 93/07278, which is herein incorporated by reference, describes the isolation of the maize trpA gene, which is preferentially expressed in pith cells. The gene sequence and promoter extending up to −1726 bp from the start of transcription are presented. Using standard molecular biological techniques, this promoter, or parts thereof, can be transferred to a vector such as pCGN1761 where it can replace the 35S promoter and be used to drive the expression of a foreign gene in a pith-preferred manner. In fact, fragments containing the pith-preferred promoter or parts thereof can be transferred to any vector and modified for utility in transgenic plants.

j. Leaf-Specific Expression:

A maize gene encoding phosphoenol carboxylase (PEPC) has been described by Hudspeth & Grula (Plant Molec Biol 12: 579-589 (1989)). Using standard molecular biological techniques the promoter for this gene can be used to drive the expression of any gene in a leaf-specific manner in transgenic plants.

k. Pollen-Specific Expression:

WO 93/07278 describes the isolation of the maize calcium-dependent protein kinase (CDPK) gene which is expressed in pollen cells. The gene sequence and promoter extend up to 1400 bp from the start of transcription. Using standard molecular biological techniques, this promoter or parts thereof, can be transferred to a vector such as pCGN1761 where it can replace the 35S promoter and be used to drive the expression of a nucleic acid sequence of the invention in a pollen-specific manner.

2. Transcriptional Terminators

A variety of transcriptional terminators are available for use in expression cassettes. These are responsible for the termination of transcription beyond the transgene and correct mRNA polyadenylation. Appropriate transcriptional terminators are those that are known to function in plants and include the CaMV 35S terminator, the tml terminator, the nopaline synthase terminator and the pea rbcS E9 terminator. These can be used in both monocotyledons and dicotyledons. In addition, a gene's native transcription terminator may be used.

3. Sequences for the Enhancement or Regulation of Expression

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize AdhI gene have been found to significantly enhance the expression of the wild-type gene under its cognate promoter when introduced into maize cells.

Intron 1 was found to be particularly effective and enhanced expression in fusion constructs with the chloramphenicol acetyltransferase gene (Callis et al., *Genes Develop.* 1: 1183-1200 (1987)). In the same experimental system, the intron from the maize bronze1 gene had a similar effect in enhancing expression. Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. *Nucl. Acids Res.* 15: 8693-8711 (1987); Skuzeski et al. *Plant Molec. Biol.* 15: 65-79 (1990)). Other leader sequences known in the art include but are not limited to: picornavirus leaders, for example, EMCV leader (Encephalomyocarditis 5' noncoding region) (Elroy-Stein, O., Fuerst, T. R., and Moss, B. PNAS USA 86:6126-6130 (1989)); potyvirus leaders, for example, TEV leader (Tobacco Etch Virus) (Allison et al., 1986); MDMV leader (Maize Dwarf Mosaic Virus); *Virology* 154: 9-20); human immunoglobulin heavy-chain binding protein (BiP) leader, (Macejak, D. G., and Sarnow, P., *Nature* 353: 90-94 (1991); untranslated leader from the coat protein mRNA of alfalfa mosaic virus (AMV RNA 4), (Jobling, S. A., and Gehrke, L., *Nature* 325:622-625 (1987); tobacco mosaic virus leader (TMV), (Gallie, D. R. et al., *Molecular Biology of RNA*, pages 237-256 (1989); and Maize Chlorotic Mottle Virus leader (MCMV) (Lommel, S. A. et al., *Virology* 81:382-385 (1991). See also, Della-Cioppa et al., *Plant Physiology* 84:965-968 (1987).

In addition to incorporating one or more of the aforementioned elements into the 5' regulatory region of a target expression cassette of the invention, other elements peculiar to the target expression cassette may also be incorporated. Such elements include but are not limited to a minimal promoter. By minimal promoter it is intended that the basal promoter elements are inactive or nearly so without upstream activation. Such a promoter has low background activity in plants when there is no transactivator present or when enhancer or response element binding sites are absent. One minimal promoter that is particularly useful for target genes in plants is the Bz1 minimal promoter, which is obtained from the bronze1 gene of maize. The Bz1 core promoter is obtained from the "myc" mutant Bz1-luciferase construct pBz1LucR98 via cleavage at the NheI site located at −53 to −58. Roth et al., *Plant Cell* 3: 317 (1991). The derived Bz1 core promoter fragment thus extends from −53 to +227 and includes the Bz1 intron-1 in the 5' untranslated region. Also useful for the invention is a minimal promoter created by use of a synthetic TATA element. The TATA element allows recognition of the promoter by RNA polymerase factors and confers a basal level of gene expression in the absence of activation (see generally, Mukumoto (1993) *Plant Mol Biol* 23: 995-1003; Green (2000) *Trends Biochem Sci* 25: 59-63)

4. Targeting of the Gene Product Within the Cell

Various mechanisms for targeting gene products are known to exist in plants and the sequences controlling the functioning of these mechanisms have been characterized in some detail. For example, the targeting of gene products to the chloroplast is controlled by a signal sequence found at the amino terminal end of various proteins which is cleaved during chloroplast import to yield the mature protein (e.g. Comai et al. J. Biol. Chem. 263: 15104-15109 (1988)). These signal sequences can be fused to heterologous gene products to effect the import of heterologous products into the chloroplast (van den Broeck, et al. Nature 313: 358-363 (1985)). DNA encoding for appropriate signal sequences can be isolated from the 5' end of the cDNAs encoding the RUBISCO protein, the CAB protein, the EPSP synthase enzyme, the GS2 protein and many other proteins which are known to be chloroplast localized. See also, the section entitled "Expression With Chloroplast Targeting" in Example 37 of U.S. Pat. No. 5,639,949.

Other gene products are localized to other organelles such as the mitochondrion and the peroxisome (e.g. Unger et al. Plant Molec. Biol. 13: 411-418 (1989)). The cDNAs encoding these products can also be manipulated to effect the targeting of heterologous gene products to these organelles. Examples of such sequences are the nuclear-encoded ATPases and specific aspartate amino transferase isoforms for mitochondria. Targeting cellular protein bodies has been described by Rogers et al. (Proc. Natl. Acad. Sci. USA 82: 6512-6516 (1985)).

In addition, sequences have been characterized which cause the targeting of gene products to other cell compartments. Amino terminal sequences are responsible for targeting to the ER, the apoplast, and extracellular secretion from aleurone cells (Koehler & Ho, Plant Cell 2: 769-783 (1990)). Additionally, amino terminal sequences in conjunction with carboxy terminal sequences are responsible for vacuolar targeting of gene products (Shinshi et al. Plant Molec. Biol. 14: 357-368 (1990)).

By the fusion of the appropriate targeting sequences described above to transgene sequences of interest it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the amino terminal ATG of the transgene. The signal sequence selected should include the known cleavage site, and the fusion constructed should take into account any amino acids after the cleavage site which are required for cleavage. In some cases this requirement may be fulfilled by the addition of a small number of amino acids between the cleavage site and the transgene ATG or, alternatively, replacement of some amino acids within the transgene sequence. Fusions constructed for chloroplast import can be tested for efficacy of chloroplast uptake by in vitro translation of in vitro transcribed constructions followed by in vitro chloroplast uptake using techniques described by Bartlett et al. In: Edelmann et al. (Eds.) Methods in Chloroplast Molecular Biology, Elsevier pp 1081-1091 (1982) and Wasmann et al. Mol. Gen. Genet. 205: 446-453 (1986). These construction techniques are well known in the art and are equally applicable to mitochondria and peroxisomes.

The above-described mechanisms for cellular targeting can be utilized not only in conjunction with their cognate promoters, but also in conjunction with heterologous promoters so as to effect a specific cell-targeting goal under the transcriptional regulation of a promoter that has an expression pattern different to that of the promoter from which the targeting signal derives.

C. Construction of Plant Transformation Vectors

Numerous transformation vectors available for plant transformation are known to those of ordinary skill in the plant transformation arts, and the genes pertinent to this invention can be used in conjunction with any such vectors. The selection of vector will depend upon the preferred transformation technique and the target species for transformation. For certain target species, different antibiotic or herbicide selection markers may be preferred. Selection markers used routinely in transformation include the nptII gene, which confers resistance to kanamycin and related antibiotics (Messing & Vierra. Gene 19: 259-268 (1982); Bevan et al., Nature 304:184-187 (1983)), the bar gene, which confers resistance to the herbicide phosphinothricin (White et al., Nucl. Acids Res 18: 1062 (1990), Spencer et al. Theor. Appl. Genet 79: 625-631 (1990)), the hph gene, which confers resistance to the antibiotic hygromycin (Blochinger & Diggelmann, Mol Cell Biol 4: 2929-2931), and the dhfr gene, which confers resistance to methatrexate (Bourouis et al., EMBO J. 2(7): 1099-1104 (1983)), the EPSPS gene, which confers resistance to glyphosate (U.S. Pat. Nos. 4,940,935 and 5,188,642), and the mannose-6-phosphate isomerase gene, which provides the ability to metabolize mannose (U.S. Pat. Nos. 5,767,378 and 5,994,629).

1. Vectors Suitable for *Agrobacterium* Transformation

Many vectors are available for transformation using *Agrobacterium tumefaciens*. These typically carry at least one T-DNA border sequence and include vectors such as pBIN19 (Bevan, Nucl. Acids Res. (1984)). Below, the construction of two typical vectors suitable for *Agrobacterium* transformation is described.

a. pCIB200 and pCIB2001:

The binary vectors pCIB200 and pCIB2001 are used for the construction of recombinant vectors for use with *Agrobacterium* and are constructed in the following manner. pTJS75kan is created by NarI digestion of pTJS75 (Schmidhauser & Helinski, J. Bacteriol. 164: 446-455 (1985)) allowing excision of the tetracycline-resistance gene, followed by insertion of an AccI fragment from pUC4K carrying an NPTII (Messing & Vierra, Gene 19: 259-268 (1982): Bevan et al., Nature 304: 184-187 (1983): McBride et al., Plant Molecular Biology 14: 266-276 (1990)). XhoI linkers are ligated to the EcoRV fragment of PCIB7 which contains the left and right T-DNA borders, a plant selectable nos/nptII chimeric gene and the pUC polylinker (Rothstein et al., Gene 53: 153-161 (1987)), and the XhoI-digested fragment are cloned into SalI-digested pTJS75kan to create pCIB200 (see also EP 0 332 104, example 19). pCIB200 contains the following unique polylinker restriction sites: EcoRI, SstI, KpnI, BglII, XbaI, and SalI. pCIB2001 is a derivative of pCIB200 created by the insertion into the polylinker of additional restriction sites. Unique restriction sites in the polylinker of pCIB2001 are EcoRI, SstI, KpnI, BglII, XbaI, SalI, MluI, BclI, AvrII, ApaI, HpaI, and StuI. pCIB2001, in addition to containing these unique restriction sites also has plant and bacterial kanamycin selection, left and right T-DNA borders for *Agrobacterium*-mediated transformation, the RK2-derived trfA function for mobilization between *E. coli* and other hosts, and the OriT and OriV functions also from RK2. The pCIB2001 polylinker is suitable for the cloning of plant expression cassettes containing their own regulatory signals.

b. pCIB10 and Hygromycin Selection Derivatives Thereof:

The binary vector pCIB10 contains a gene encoding kanamycin resistance for selection in plants and T-DNA right and left border sequences and incorporates sequences from the wide host-range plasmid pRK252 allowing it to replicate in both *E. coli* and *Agrobacterium*. Its construction is described by Rothstein et al. (Gene 53: 153-161 (1987)). Various derivatives of pCIB10 are constructed which incorporate the gene for hygromycin B phosphotransferase described by Gritz et al. (Gene 25: 179-188 (1983)). These derivatives enable selection of transgenic plant cells on hygromycin only (pCIB743), or hygromycin and kanamycin (pCIB715, pCIB717).

2. Vectors Suitable for Non-Agrobacterium Transformation

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques that do not rely on *Agrobacterium* include transformation via particle bombardment, protoplast uptake (e.g. PEG and electroporation) and microinjection. The choice of vector depends largely on the preferred selection for the species being transformed. Below, the construction of typical vectors suitable for non-*Agrobacterium* transformation is described.

a. pCIB3064:

pCIB3064 is a pUC-derived vector suitable for direct gene transfer techniques in combination with selection by the herbicide basta (or phosphinothricin). The plasmid pCIB246 comprises the CaMV 35S promoter in operational fusion to the *E. coli* GUS gene and the CaMV 35S transcriptional terminator and is described in the PCT published application WO 93/07278. The 35S promoter of this vector contains two ATG sequences 5' of the start site. These sites are mutated using standard PCR techniques in such a way as to remove the ATGs and generate the restriction sites SspI and PvuII. The new restriction sites are 96 and 37 bp away from the unique SalI site and 101 and 42 bp away from the actual start site. The resultant derivative of pCIB246 is designated pCIB3025. The GUS gene is then excised from pCIB3025 by digestion with SalI and SacI, the termini rendered blunt and religated to generate plasmid pCIB3060. The plasmid pJIT82 is obtained from the John Innes Centre, Norwich and the a 400 bp SmaI fragment containing the bar gene from *Streptomyces viridochromogenes* is excised and inserted into the HpaI site of pCIB3060 (Thompson et al. EMBO J 6: 2519-2523 (1987)). This generated pCIB3064, which comprises the bar gene under the control of the CaMV 35S promoter and terminator for herbicide selection, a gene for ampicillin resistance (for selection in *E. coli*) and a polylinker with the unique sites SphI, PstI, HindIII, and BamHI. This vector is suitable for the cloning of plant expression cassettes containing their own regulatory signals.

b. pSOG19 and pSOG35:

pSOG35 is a transformation vector that utilizes the *E. coli* gene dihydrofolate reductase (DFR) as a selectable marker conferring resistance to methotrexate. PCR is used to amplify the 35S promoter (~800 bp), intron 6 from the maize Adh1 gene (~550 bp) and 18 bp of the GUS untranslated leader sequence from pSOG10. A 250-bp fragment encoding the *E. coli* dihydrofolate reductase type II gene is also amplified by PCR and these two PCR fragments are assembled with a SacI-PstI fragment from pB1221 (Clontech) which comprises the pUC19 vector backbone and the nopaline synthase terminator. Assembly of these fragments generates pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus (MCMV) generates the vector pSOG35. pSOG19 and pSOG35 carry the pUC gene for ampicillin resistance and have HindIII, SphI, PstI and EcoRI sites available for the cloning of foreign substances.

3. Vector Suitable for Chloroplast Transformation

For expression of a nucleotide sequence of the present invention in plant plastids, plastid transformation vector pPH143 (WO 97/32011, example 36) is used. The nucleotide sequence is inserted into pPH143 thereby replacing the PRO- TOX coding sequence. This vector is then used for plastid transformation and selection of transformants for spectinomycin resistance. Alternatively, the nucleotide sequence is inserted in pPH143 so that it replaces the aadH gene. In this case, transformants are selected for resistance to PROTOX inhibitors.

D. Transformation

Once a nucleic acid sequence of the invention has been cloned into an expression system, it is transformed into a plant cell. The receptor and target expression cassettes of the present invention can be introduced into the plant cell in a number of art-recognized ways. Methods for regeneration of plants are also well known in the art. For example, Ti plasmid vectors have been utilized for the delivery of foreign DNA, as well as direct DNA uptake, liposomes, electroporation, microinjection, and microprojectiles. In addition, bacteria from the genus *Agrobacterium* can be utilized to transform plant cells. Below are descriptions of representative techniques for transforming both dicotyledonous and monocotyledonous plants, as well as a representative plastid transformation technique.

1. Transformation of Dicotyledons

Transformation techniques for dicotyledons are well known in the art and include *Agrobacterium*-based techniques and techniques that do not require *Agrobacterium*. Non-Agrobacterium techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., EMBO J 3: 2717-2722 (1984), Potrykus et al., Mol. Gen. Genet. 199: 169-177 (1985), Reich et al., Biotechnology 4: 1001-1004 (1986), and Klein et al., Nature 327: 70-73 (1987). In each case the transformed cells are regenerated to whole plants using standard techniques known in the art.

*Agrobacterium*-mediated transformation is a preferred technique for transformation of dicotyledons because of its high efficiency of transformation and its broad utility with many different species. *Agrobacterium* transformation typically involves the transfer of the binary vector carrying the foreign DNA of interest (e.g. pCIB200 or pCIB2001) to an appropriate *Agrobacterium* strain which may depend of the complement of vir genes carried by the host *Agrobacterium* strain either on a co-resident Ti plasmid or chromosomally (e.g. strain CIB542 for pCIB200 and pCIB2001 (Uknes et al. Plant Cell 5: 159-169 (1993)). The transfer of the recombinant binary vector to *Agrobacterium* is accomplished by a triparental mating procedure using *E. coli* carrying the recombinant binary vector, a helper *E. coli* strain which carries a plasmid such as pRK2013 and which is able to mobilize the recombinant binary vector to the target *Agrobacterium* strain. Alternatively, the recombinant binary vector can be transferred to *Agrobacterium* by DNA transformation (Höfgen & Willmitzer, Nucl. Acids Res. 16: 9877 (1988)).

Transformation of the target plant species by recombinant *Agrobacterium* usually involves co-cultivation of the *Agrobacterium* with explants from the plant and follows protocols well known in the art. Transformed tissue is regenerated on selectable medium carrying the antibiotic or herbicide resistance marker present between the binary plasmid T-DNA borders.

Another approach to transforming plant cells with a gene involves propelling inert or biologically active particles at plant tissues and cells. This technique is disclosed in U.S. Pat. Nos. 4,945,050, 5,036,006, and 5,100,792 all to Sanford et al. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium or a bacteriophage, each containing DNA sought to be introduced) can also be propelled into plant cell tissue.

2. Transformation of Monocotyledons

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both these techniques are suitable for use with this invention. Co-transformation may have the advantage of avoiding complete vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. Biotechnology 4: 1093-1096 (1986)).

Patent Applications EP 0 292 435, EP 0 392 225, and WO 93/07278 describe techniques for the preparation of callus and protoplasts from an elite inbred line of maize, transformation of protoplasts using PEG or electroporation, and the regeneration of maize plants from transformed protoplasts. Gordon-Kamm et al. (Plant Cell 2: 603-618 (1990)) and Fromm et al. (Biotechnology 8: 833-839 (1990)) have published techniques for transformation of A188-derived maize line using particle bombardment. Furthermore, WO 93/07278 and Koziel et al. (Biotechnology 11: 194-200 (1993)) describe techniques for the transformation of elite inbred lines of maize by particle bombardment. This technique utilizes immature maize embryos of 1.5-2.5 mm length excised from a maize ear 14-15 days after pollination and a PDS-1000 He Biolistics device for bombardment.

Transformation of rice can also be undertaken by direct gene transfer techniques utilizing protoplasts or particle bombardment. Protoplast-mediated transformation has been described for Japonica-types and Indica-types (Zhang et al. Plant Cell Rep 7: 379-384 (1988); Shimamoto et al. Nature 338: 274-277 (1989); Datta et al Biotechnology 8: 736-740 (1990)). Both types are also routinely transformable using particle bombardment (Christou et al. Biotechnology 9: 957-962 (1991)). Furthermore, WO 93/21335 describes techniques for the transformation of rice via electroporation.

Patent Application EP 0 332 581 describes techniques for the generation, transformation and regeneration of Pooideae protoplasts. These techniques allow the transformation of *Dactylis* and wheat. Furthermore, wheat transformation has been described by Vasil et al. (Biotechnology 10: 667-674 (1992)) using particle bombardment into cells of type C long-term regenerable callus, and also by Vasil et al. (Biotechnology 11: 1553-1558 (1993)) and Weeks et al. (Plant Physiol. 102: 1077-1084 (1993)) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75-1 mm in length) are plated onto MS medium with 3% sucrose (Murashiga & Skoog, Physiologia Plantarum 15: 473-497 (1962)) and 3 mg/l 2,4-D for induction of somatic embryos, which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2-3 hours and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics® helium device using a burst pressure of ~1000 psi using a standard 80 mesh screen. After bombardment, the embryos are placed back into the dark to recover for about 24 hours (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contain half-strength MS, 2% sucrose, and the same concentration of selection agent.

Transformation of monocotyledons using *Agrobacterium* has also been described. See, WO 94/00977 and U.S. Pat. No. 5,591,616, both of which are incorporated herein by reference. See also, Negrotto et al., *Plant Cell Reports* 19: 798-803 (2000), incorporated herein by reference.

3. Transformation of Plastids

Seeds of *Nicotiana tabacum* c.v. 'Xanthi nc' are germinated seven per plate in a 1" circular array on T agar medium and bombarded 12-14 days after sowing with 1 μm tungsten particles (M10, Biorad, Hercules, Calif.) coated with DNA from plasmids pPH143 and pPH145 essentially as described (Svab, Z. and Maliga, P. (1993) PNAS 90, 913-917). Bombarded seedlings are incubated on T medium for two days after which leaves are excised and placed abaxial side up in bright light (350-500 μmol photons/$m^2$/s) on plates of RMOP medium (Svab, Z., Hajdukiewicz, P. and Maliga, P. (1990) PNAS 87, 8526-8530) containing 500 μg/ml spectinomycin dihydrochloride (Sigma, St. Louis, Mo.). Resistant shoots appearing underneath the bleached leaves three to eight weeks after bombardment are subcloned onto the same selective medium, allowed to form callus, and secondary shoots isolated and subcloned. Complete segregation of transformed plastid genome copies (homoplasmicity) in independent subclones is assessed by standard techniques of Southern blotting (Sambrook et al., (1989) *Molecular Cloning: A Laboratory Manual*, Cold Spring Harbor Laboratory, Cold Spring Harbor). BamHI/EcoRI-digested total cellular DNA (Mettler, I. J. (1987) *Plant Mol Biol Reporter* 5, 346-349) is separated on 1% Tris-borate (TBE) agarose gels, transferred to nylon membranes (Amersham) and probed with $^{32}$P-labeled random primed DNA sequences corresponding to a 0.7 kb BamHI/HindIII DNA fragment from pC8 containing a portion of the rps7/12 plastid targeting sequence. Homoplasmic shoots are rooted aseptically on spectinomycin-containing MS/IBA medium (McBride, K. E. et al. (1994) *PNAS* 91, 7301-7305) and transferred to the greenhouse.

Breeding and Seed Production

A. Breeding

The plants obtained via transformation with a nucleic acid sequence of the present invention can be any of a wide variety of plant species, including those of monocots and dicots; however, the plants used in the method of the invention are preferably selected from the list of agronomically important target crops set forth supra. The expression of a gene of the present invention in combination with other characteristics important for production and quality can be incorporated into plant lines through breeding. Breeding approaches and techniques are known in the art. See, for example, Welsh J. R., *Fundamentals of Plant Genetics and Breeding*, John Wiley & Sons, NY (1981); *Crop Breeding*, Wood D. R (Ed.) American Society of Agronomy Madison, Wis. (1983); Mayo O., *The Theory of Plant Breeding*, Second Edition, Clarendon Press, Oxford (1987); Singh, D. P., *Breeding for Resistance to Diseases and Insect Pests*, Springer-Verlag, N Y (986); and Wricke and Weber, *Quantitative Genetics and Selection Plant Breeding*, Walter de Gruyter and Co., Berlin (1986).

The genetic properties engineered into the transgenic seeds and plants described above are passed on by sexual reproduction or vegetative growth and can thus be maintained and propagated in progeny plants. Generally said maintenance and propagation make use of known agricultural methods developed to fit specific purposes such as tilling, sowing or harvesting. Specialized processes such as hydroponics or greenhouse technologies can also be applied. As the growing crop is vulnerable to attack and damages caused by insects or infections as well as to competition by weed plants, measures are undertaken to control weeds, plant diseases, insects, nematodes, and other adverse conditions to improve yield. These include mechanical measures such a tillage of the soil or removal of weeds and infected plants, as well as the application of agrochemicals such as herbicides, fungicides, gametocides, nematicides, growth regulants, ripening agents and insecticides.

Use of the advantageous genetic properties of the transgenic plants and seeds according to the invention can further be made in plant breeding, which aims at the development of plants with improved properties such as tolerance of pests, herbicides, or stress, improved nutritional value, increased yield, or improved structure causing less loss from lodging or shattering. The various breeding steps are characterized by well-defined human intervention such as selecting the lines to be crossed, directing pollination of the parental lines, or selecting appropriate progeny plants. Depending on the desired properties, different breeding measures are taken. The relevant techniques are well known in the art and include but are not limited to hybridization, inbreeding, backcross breeding, multiline breeding, variety blend, interspecific hybridization, aneuploid techniques, etc. Hybridization techniques also include the sterilization of plants to yield male or female sterile plants by mechanical, chemical, or biochemical means. Cross pollination of a male sterile plant with pollen of a different line assures that the genome of the male sterile but female fertile plant will uniformly obtain properties of both parental lines. Thus, the transgenic seeds and plants according to the invention can be used for the breeding of improved plant lines, that for example, increase the effectiveness of conventional methods such as herbicide or pesticide treatment or allow one to dispense with said methods due to their modified genetic properties. Alternatively new crops with improved stress tolerance can be obtained, which, due to their optimized genetic "equipment", yield harvested product of better quality than products that were not able to tolerate comparable adverse developmental conditions.

B. Seed Production

In seed production, germination quality and uniformity of seeds are essential product characteristics. As it is difficult to keep a crop free from other crop and weed seeds, to control seedborne diseases, and to produce seed with good germination, fairly extensive and well-defined seed production practices have been developed by seed producers, who are experienced in the art of growing, conditioning and marketing of pure seed. Thus, it is common practice for the farmer to buy certified seed meeting specific quality standards instead of using seed harvested from his own crop. Propagation material to be used as seeds is customarily treated with a protectant coating comprising herbicides, insecticides, fungicides, bactericides, nematicides, molluscicides, or mixtures thereof. Customarily used protectant coatings comprise compounds such as captan, carboxin, thiram (TMTD®), methalaxyl (Apron®), and pirimiphos-methyl (Actellic®). If desired, these compounds are formulated together with further carriers, surfactants or application-promoting adjuvants customarily employed in the art of formulation to provide protection against damage caused by bacterial, fungal or animal pests. The protectant coatings may be applied by impregnating propagation material with a liquid formulation or by coating with a combined wet or dry formulation. Other methods of application are also possible such as treatment directed at the buds or the fruit.

Employing methods known to the skilled artisan, the transgenic plant cells may be regenerated to whole plants. A further subject matter of the invention includes plants that contain the above-described transgenic plant cells. The transgenic plants may in principle be plants of any desired species, i.e. they may be monocotyledonous as well as dicotyledonous plants. Preferably, the plant and plant cells utilized in the invention are transgenic maize or transgenic rice.

Due to the expression or the additional expression of a nucleic acid molecule encoding glucan dikinase protein, the transgenic plant cells and plants used in the invention synthesize a starch which is modified when compared to starch from wild-type plants, i.e. non-transformed plants, particularly with respect to the viscosity of aqueous solutions of this starch and/or to the phosphate content.

Hence, the starch obtainable from the transgenic plant cells and plants of the invention is the subject matter of the present invention.

Covalent derivatization of starch with ionic functional group(s) increases its solubility and swelling capacity in any ionic medium, making the modified starch molecules more accessible to other molecules (e.g., modifying agents chemicals and/or enzymes). For example, covalently modifying glucose residues of starch with an ionic phosphate group can increase the affinity of the starch molecules for water or any polar solvent. This derivatization can also assists the swelling of the starch through electrical repulsion between the doubly negatively charged phosphate groups attached to strands of glucose residues. The swelled and hydrated phosphorylated starch is more susceptible to attack by a modifying agent, including for example, hydrolytic enzyme, chemicals and/or enzymes for further derivatization.

Examples of modifying agents include, but are not limited to, cross linking agents such as phosphorus oxychloride, sodium trimetaphosphate, adipic-acetic anhydride etc. and substituting agents like proplene oxide, 1-octenyl succinic anhydride, and acetic anhydride.

The starch obtainable from the transgenic plants of the invention may be used for food and feed applications. The use of the starch, derivatized with ionic functional group(s) (e.g. phosphate) may not only increase the proportion of starch available for hydrolysis, but may also increase the rate of starch hydrolysis and/or decrease the enzyme requirement to achieve complete hydrolysis.

The modified starch of the invention may be used, for example, in the following:

In animal feed. Formulation of diet with easily digestible starch and hence more extractable dietary energy. While the modified starch may be used in the diets of any animal, it is preferred that such starch is used in the diets of monogastric animals, including, but not limited to, chicken and pig. The modified starch is also useful in diets for ruminants, such as cows, goats, and sheep.

In human food. Formulation of diet with easily digestible starch and hence more extractable dietary energy.

In the fermentation process, as fermentable raw-material. Starch, useful in different fermentation processes (e.g. ethanol production), is first broken down to easily fermentable sugars (degree of polymerization usually less than or equal to 3) by amylase and/or glucoamylase. This enzymatic hydrolysis is followed by fermentation, which converts sugars to various fermentation products (e.g. ethanol). Hence, a starch that can be more easily (in less time and/or by using of lower enzyme dose) hydrolyzed by amylase and/or glucoamylase may serve as a better starting substrate for the fermentation process.

The modified starch of the invention may be used in any fermentation process, including, but not limited to, ethanol production, lactic acid production, and polyol production (such as glyercol production).

Improved digestibility of the modified starch of the invention, i.e., the glucan dikinase-cornstarch, at ambient temperature can make the 'raw-starch fermentation' process economically profitable by making larger portion of the starch available and accessible for hydrolysis by the hydrolases.

Accordingly, the modified starch of the invention may be used in raw starch fermentation. In the raw starch fermentation, the starch is not liquefied before enzymatic hydrolysis, the hydrolysis is carried at ambient temperature simultaneously with the fermentation process.

Derivatization of starch in-planta using the method of the invention, namely, the method of transgenic expression of glucan dikinase protein allows improved starch solubility and swelling power and increased starch digestibility when used as feed, food or as a fermentable substrate.

Also included in the invention is a method to prepare a solution of hydrolyzed starch product comprising treating a plant or plant part comprising starch granules under conditions which activate the glucan dikinase polypeptide thereby processing the starch granules to form an aqueous solution comprising hydrolyzed starch product. The plant or plant part utilized in the invention is a transgenic plant or plant part, the genome of which is augmented with an expression cassette encoding a glucan dikinase polypeptide. The hydrolyzed starch product may comprise a dextrin, maltooligosaccharide, glucose and/or mixtures thereof. The method may further comprise isolating the hydrolyzed starch product and/or fermenting the hydrolyzed starch product.

The glucan dikinase polypeptide is preferably expressed in the endosperm. The sequence of the glucan dikinase gene may be operably linked to a promoter and to a signal sequence that targets the enzyme to the starch granule.

The invention also encompasses a method of preparing hydrolyzed starch product comprising treating a plant or plant part comprising starch granules under conditions which activate the glucan dikinase polypeptide thereby processing the starch granules to form an aqueous solution comprising a hydrolyzed starch product. The plant or plant part utilized in the invention is a transgenic plant or plant part, the genome of which is augmented with an expression cassette encoding a glucan dikinase polypeptide.

Also included is a method of preparing fermentation products, such as ethanol, comprising treating a plant or plant part comprising starch granules under conditions to activate the glucan dikinase polypeptide thereby digesting polysaccharide to form oligosaccharide or fermentable sugar, and incubating the fermentable sugar under conditions that promote the conversion of the fermentable sugar or oligosaccharide into ethanol. The plant or plant part utilized in the invention is a transgenic plant or plant part, the genome of which is augmented with an expression cassette encoding a glucan dikinase polypeptide.

The plant part may be a grain, fruit, seed, stalks, wood, vegetable or root, Preferably the plant part is obtained from a plant such as oats, barley, corn or rice. Fermentation products include, but are not limited to, ethanol, acetic acid, glycerol, and lactic acid.

Also encompassed is a method of preparing maltodextrin comprising mixing transgenic grain with water, heating said mixture, separating solid from the dextrin syrup generated, and collecting the maltodextrin. In addition, a method of preparing dextrins or sugars from grain expressing glucan dikinase is included.

The invention is further directed to a method of producing fermentable sugar employing transgenic grain expressing glucan dikinase.;

The increased solubility and swelling power of the modified starches derivatized with ionic functional groups make them more susceptible to attack not only by hydrolytic enzymes but also by any modifying agent. Hence the modified starches may be even further modified by additional enzymatic and/or chemical modifications. Swelled and solvated starch may allow increased penetration of the modifying agent into the starch molecule/granule, and therefore may accommodate a higher degree of substitution, as well as uniform distribution of the functional groups in the starch molecule/granule.

The invention will be further described by the following methods and examples, which are not intended to limit the scope of the invention in any manner.

EXAMPLES

Example 1

Constructs for Expression of R1 in Corn

PCR Amplification and Cloning of Potato R1-cDNA.

The full-length cDNA was amplified by PCR from a cDNA-library of potato (*Solanum tuberosum*) tissues using primers R1-5'-pr: 5'-T GCA GCC ATG GGT AAT TCC TTA GGG AAT AAC-3' (SEQ ID NO:1) and R1-3'-pr: 5'-TC CAA GTC GAC TCA CAT CTG AGG TCT TGT CTG-3' (SEQ ID NO:2) designed from GenBank Accession No. Y09533 [Lorberth R., Ritte G., Willmitzer L., Kossmann J., Nature Biotech. 1998, 16, 473-477]. The amplified DNA was cloned into pCR vector using TA cloning kit (Invitrogen). The sequence of the insert was confirmed and then moved (cut and ligated) into agro-transformation vector described below.

Construction of Maize Codon-Optimized Genes for R1:

The amino acid sequence for R1-protein from was obtained from the literature [Lorberth R., Ritte G., Willmitzer L., Kossmann J., Nature Biotech. 1998, 16, 473-477]. Based on the published amino acid sequence of the protein, the maize-optimized synthetic gene (SEQ ID NO: 28) encoding the R1 was designed.

Isolation of Promoter Fragments (γ-Zein) for Endosperm-Specific Expression

The (γ-zein) promoter used in the constructs described herein was isolated as disclosed in International Publication No. WO 03/018766, published Mar. 6, 2003, which is incorporated by reference in its entirety herein.

Construction of Agro-Transformation Vectors for R1:

The plasmid pNOV4080 (FIG. 1) was constructed by ligating the PCR amplified potato R1-DNA (NcoI and SalI are the two flanking restriction sites) behind (i.e., 3' of) the maize γ-zein promoter. The transformation into maize was carried out via *Agrobacterium* infection. The transformation vector contained the phosphomannose isomerase (PMI) gene that allows selection of transgenic cells with mannose. Transformed maize plants were either self-pollinated and seed was collected for analysis.

Figure 2:
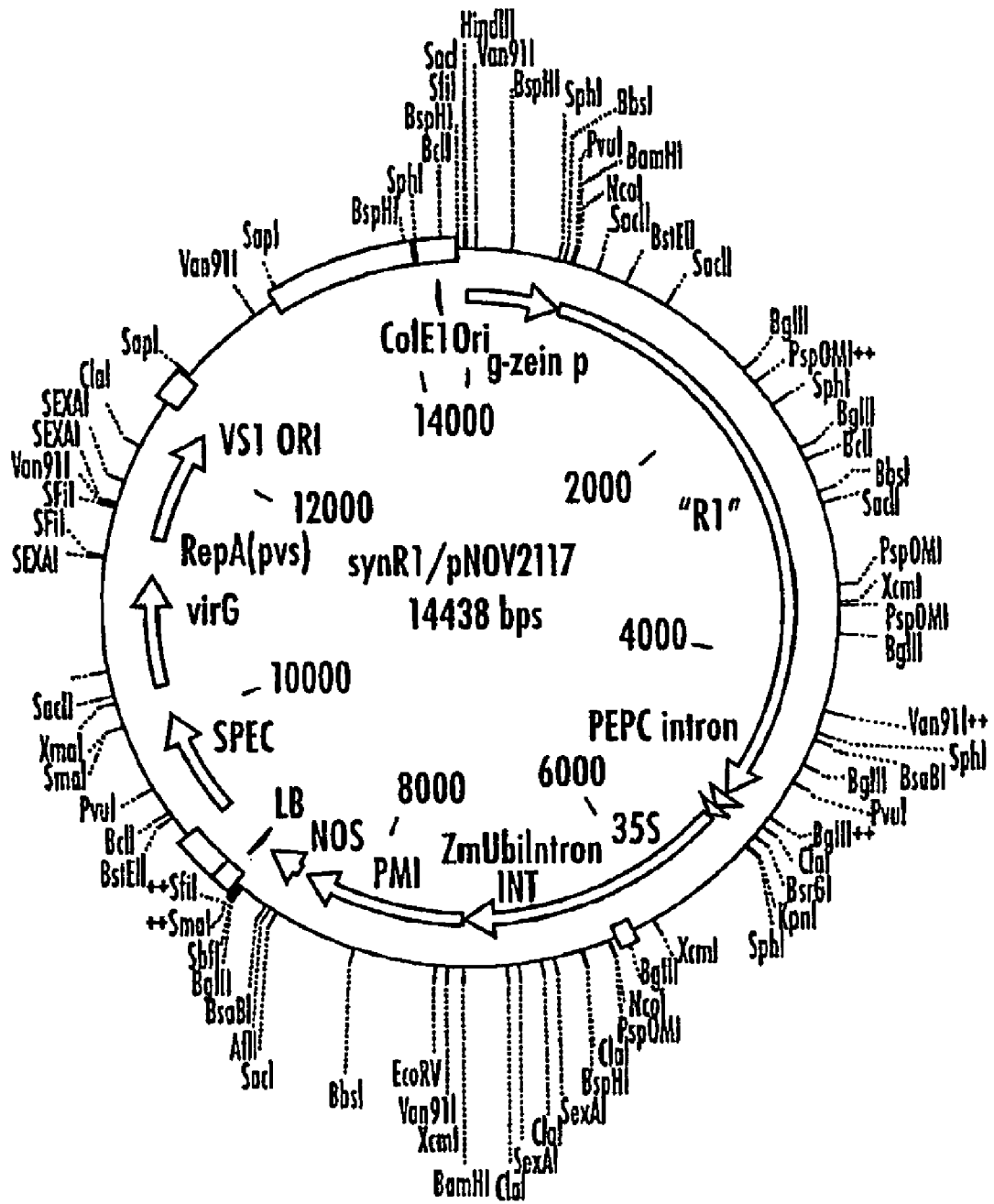
FIG. 2 depicts an *Agrobacterium*-vector with synthetic R1 as insert.

The plasmid pNOV 2117 (FIG. 2) was constructed in a similar manner. The insert is a synthetically made R1-DNA with maize-codon optimized sequence coding for the amino acid sequence shown in SEQ ID NO: 27. A description of pNOV2117 is disclosed in International Publication No. WO 03/018766, published Mar. 6, 2003.

Example 2

*Agrobacterium* Transformation

A. Transformation Plasmids and Selectable Marker.

The genes used for transformation were cloned into a vector suitable for maize transformation. Vectors used in this example contained the phosphomannose isomerase (PMI) gene for selection of transgenic lines (Negrotto et al. (2000) Plant Cell Reports 19: 798-803).

B. Preparation of *Agrobacterium tumefaciens*.

*Agrobacterium* strain LBA4404 (pSB1) containing the plant transformation plasmid was grown on YEP (yeast extract (5 g/L), peptone (10 g/L), NaCl (5 g/L), 15 g/l agar, pH 6.8) solid medium for 2-4 days at 28° C. Approximately $0.8 \times 10^9$ *Agrobacterium* were suspended in LS-inf media supplemented with 100 μM As (Negrotto et al., (2000) Plant Cell Rep 19: 798-803). Bacteria were pre-induced in this medium for 30-60 minutes.

C. Inoculation.

Immature embryos from A188 or other suitable genotype were excised from 8-12 day old ears into liquid LS-inf+100 μM As. Embryos were rinsed once with fresh infection medium. *Agrobacterium* solution was then added and embryos were vortexed for 30 seconds and allowed to settle with the bacteria for 5 minutes. The embryos were then transferred scutellum side up to LSAs medium and cultured in the dark for two to three days. Subsequently, between 20 and 25 embryos per petri plate were transferred to LSDc medium supplemented with cefotaxime (250 mg/l) and silver nitrate (1.6 mg/l) and cultured in the dark for 28° C. for 10 days.

D. Selection of Transformed Cells and Regeneration of Transformed Plant.

Immature embryos producing embryogenic callus were transferred to LSD1M0.5S medium. The cultures were selected on this medium for 6 weeks with a subculture step at 3 weeks. Surviving calli were transferred to Reg1 medium supplemented with mannose. Following culturing in the light (16 hour light/8 hour dark regiment), green tissues were then transferred to Reg2 medium without growth regulators and incubated for 1-2 weeks. Plantlets are transferred to Magenta GA-7 boxes (Magenta Corp, Chicago Ill.) containing Reg3 medium and grown in the light. After 2-3 weeks, plants were tested for the presence of the PMI genes and other genes of interest by PCR. Positive plants from the PCR assay were transferred to the greenhouse.

Expression of R1 in Maize Seed Endosperm.

T2 or T3 seed from self-pollinated maize plants transformed with either pNOV 4080 were obtained. The pNOV 4080 construct targets the expression of the R1 in the endosperm. Normal accumulation of the starch in the kernels was observed, as determined by staining for starch with an iodine solution. The expression of R1 was detected by Western blot analysis using an antibody raised against a R1-peptide fragment (YTPEKEKEEYEAARTELQEEIARGA) (SEQ ID NO:3). The increased dikinase activity of R1 [Ritte G., Lloyd J. R., Eckermann N., Rottmann A., Kossmann J., Steup M., 2002, PNAS, 99 (10) 7166-7171; Ritte G., Steup M., Kossmann J., Lloyd J. R., 2003, Planta 216, 798-801.] can also be detected in the extract made from the endosperm of the transgenic corn overexpressing R1-protein.

Example 3

Phosphorylated Starch from the Transgenic R1-Corn

Isolation of Starch from Corn:

The endosperm was obtained after removing the embryo and pericarp from the kernel, and kept on ice. To 12.6 g of endosperm add 60 ml of buffer (1.25 mM DTT, 10 mM EDTA, 10% glycerol, and 50 mM Tris-HCl, pH 7.0) and the mixture was homogenized. The homogenate was filtered through a layer of Miracloth (Calbiochem) to remove cell debris. Centrifugation of the filtrate was carried out at 15,000 g for 15 minutes, at 4° C. The delicate yellow gel-like layer on top of the packed white layer of sedimented starch granules was removed by gentle aspiration to obtaine clean-white granules. The resultant starch granules was washed twice with the buffer, twice with 80% ethanol to remove low molecular storage proteins, twice with cold acetone, and dried. The starch was isolated and stored at room temperature. [Chen Mu-Forster, Chee Harn, Yuan-Tih ko, George W. Singletary, Peter L. Keeling and Bruce P. Wasserman (1994) *The Plant Journal* 6(2), 151-159.]

Preparation of Starch Hydrolysate by Mild-Acid Hydrolysis of the Starch Sample:

Starch (100-500 mg) was suspended in 0.5-2.5 ml of 0.7 N HCl and kept at 95° C. for 4 hours. The glucose in the starch hydrolysate was quantified by glucose estimation kit (Sigma) and by HPLC analysis.

Glucose in the starch hydrolysate was oxidized to gluconic acid in the reaction catalyzed by Glucose Oxidase [from Starch/Glucose estimation kit (Sigma)]. The mixture was incubated at 37° C. for 30 minutes. Hydrogen peroxide released during the reaction changes the colorless o-Dianisidine to brown oxidized o-Dianisidine in presence of Peroxidase. Then, 12 N sulfuric acid was added to stop the reaction and to form a stable pink-colored product. Absorbance at 540 nm was measured for quantification of the amount of glucose in the sample, with respect to standard glucose solution.

An aliquot of the sample was diluted 5 to 25-fold, filtered through 0.2-micron filter for HPLC analysis.

The samples were analyzed by HPLC using the following conditions:
Column: Alltech Prevail Carbohydrate ES 5 micron 250×4.6 mm
Detector: Alltech ELSD 2000
Pump: Gilson 322
Injector: Gilson 215 injector/diluter
Solvents: HPLC grade Acetonitrile (Fisher Scientific) and Water (purified by Waters Millipore System)
Gradient used for oligosaccharides of low degree of polymerization (DP1-15).

| Time | % Water | % Acetonitrile |
|---|---|---|
| 0 | 15 | 85 |
| 5 | 15 | 85 |
| 25 | 50 | 50 |
| 35 | 50 | 50 |
| 36 | 80 | 20 |
| 55 | 80 | 20 |
| 56 | 15 | 85 |
| 76 | 15 | 85 |

Gradient used for saccharides of high degree of polymerization (DP 20-100 and above).

| Time | % Water | % Acetonitrile |
|---|---|---|
| 0 | 35 | 65 |
| 60 | 85 | 15 |
| 70 | 85 | 15 |
| 85 | 35 | 65 |
| 100 | 35 | 65 |

System used for data analysis: Gilson Unipoint Software System Version 3.2. Estimation of sample sugar was done by integration of the peak-area generated on a HPLC profile and comparison with calibration-curve (peak-area vs weight) obtained using authentic sugar standards.

Glucose 6-Phosphate Dehydrogenase Assay to Determine the Level of Phosphorylation at the 6-Position of Glucose Residues in Starch:

To an aliquot (100 µl) of the mild-acid starch hydrolysate sample 800 µl of buffer containing 100 mM MOPS-KOH (pH 7.5), 100 mM $MgCl_2$, 2 mM EDTA in a cuvette and neutralize with 80-100 µl of 0.7 N KOH. The reaction was started by adding NAD (final concentration 0.4 mM) and 2 unit of Glucose 6-Phosphate dehydrogenase in a final assay volume of 1 mL. The reaction rate was calculated by measuring the change in absorption at 340 nm for 2 minutes.

[Nielsen, T. H., Wichmann, B., Enevoldsen, K., and Moller, B. L. Plant Physiol. (1994) 105, 111-117.]

Figure 3:
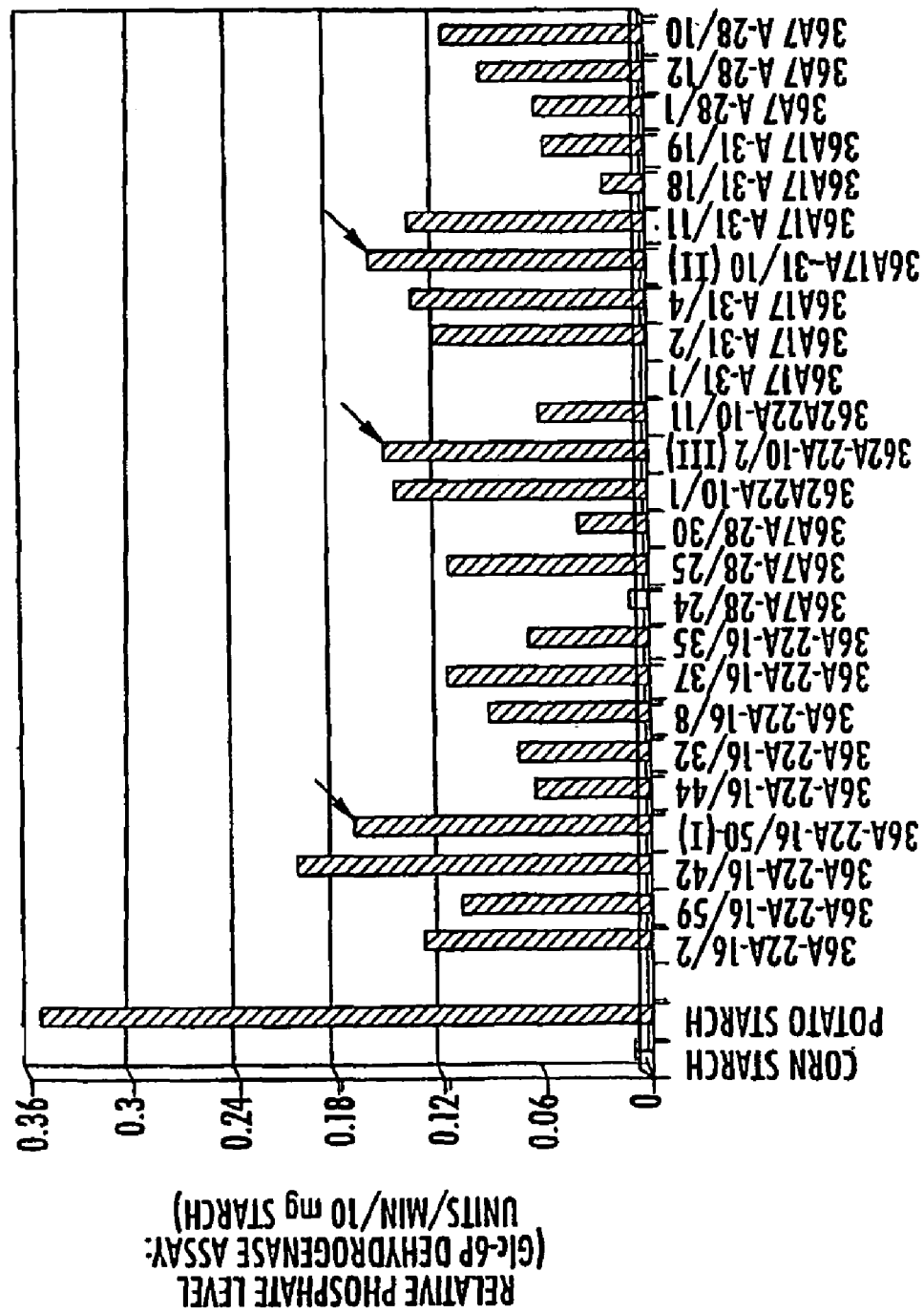
FIG. 3 is a graph showing estimations of glucose 6-phosphate after complete hydrolysis of starch and Increased phosphorylation of R1-cornstarch.

FIG. 3. Estimation of glucose 6-phosphate after complete hydrolysis of starch. Increased phosphorylation of R1-corn-starch. Starch samples (~100 mg) isolated from the corn kernels (T3 seeds) of different events (transgenic R1-corn) were completely hydrolyzed (mild-acid hydrolysis, as described above) to glucose. The glucose and glucose 6-phosphate in the hydrolysates were quantified as described above. FIG. 3 shows the relative level of phosphorylation of the starch in different samples, as measure by the glucose 6-phosphate dehydrogenase assays and normalized with respect to the estimated glucose in the samples.

Screening of different R1-transgenic corn events using method above described method indicated high level of in planta phosphorylation of starch in corn expressing potato R1-transgene. The starch sample isolated from non-transgenic corn is not phosphorylated, as it is hardly detectable by this assay. The level of phosphorylation that is observed in case of R1-cornstarch is almost half the level that is observed in potato starch (commercially available sample). It is to be noted that this assay method detects the phosphorylation at the 6-position only, phosphorylation at any 3- or 2-position of glucose residue of starch is not detectable by this method. The three events (labeled as I, II & III, indicated with arrow) were used for further characterization (experiments described below) of the R1-corn.

$^{31}$P-NMR Analysis to Estimate the Level of Ester-Linked Phosphate in Starch Sample:

Mild-acid hydrolyzed starch sample was cooled down to room temperature, buffered with 100 mM acetate buffer (pH 5.5) and finally neutralized with 2.8 N KOH. The samples were blown down under a stream of $N_2$ gas. A known amount of β-NAD was added to the sample. The sample was dissolved in 300 µl $H_2O$ and 300 µl DMSO $d_6$. Spectral data was acquired on a DPX-300 at 30° C. β-NAD was used as the standard, used for quantification of the ester-linked phosphate in the sample. The quantification was carried out by intregation of the peak. Estimation of the phosphate level in the sample took into account the any presence of contaminating inorganic phosphate in the sample.

Table 1. Estimation of covalently-bound phosphate by 31P-NMR. The % phosphate shown here is amount of ester-linked phosphate present in the starch hydrolysate compared to the glucose in the sample. The experiments were carried out as described above.

| STARCH SAMPLE | PHOSPHATE (%) |
| --- | --- |
| Non-transgenic cornstarch | 0 |
| R1-Cornstarch I (T3 seeds) | 0.0736 |
| R1-Cornstarch II (T3 seeds) | 0.0634 |
| R1-Cornstarch II (T3 seeds) | 0.0388 |
| Potato Starch | 0.1263 |

This result corroborates with that obtained by the glucose 6-phosphate assay; the phosphorylation level observed in R1-cornstarch samples was up to half of that observed in case of potato starch. Unlike, the glucose 6-phosphate assay method described above, this method estimates the total ester-linked phosphate associated with the starch sample.

Example 4

Swelling and Solubility of R1-Cornstarch

The starch samples from the R1-corns, non-transgenic corn and the transgenic negative-control corn were prepared as described above; while the other starch samples were commercially obtained. The swelling power of starch samples were determined as described by Subramanian et al. (Subramanian, V., Hosney, R. C., Bramel-Cox, P. 1994, Cereal Chem. 71, 2772-275.) with minor modifications. The 1% (w/w) suspension of starch and distilled water was heated to 95° C. for 30 minutes. Lump formation was prevented by shaking. The mixture was centrifuged at 3000 rpm for 15 minutes. The supernatant was carefully removed and the swollen starch sediment was weighed the swelling power was the ratio in weight of the wet sediment to the initial weight of the dry starch.

Figure 4:
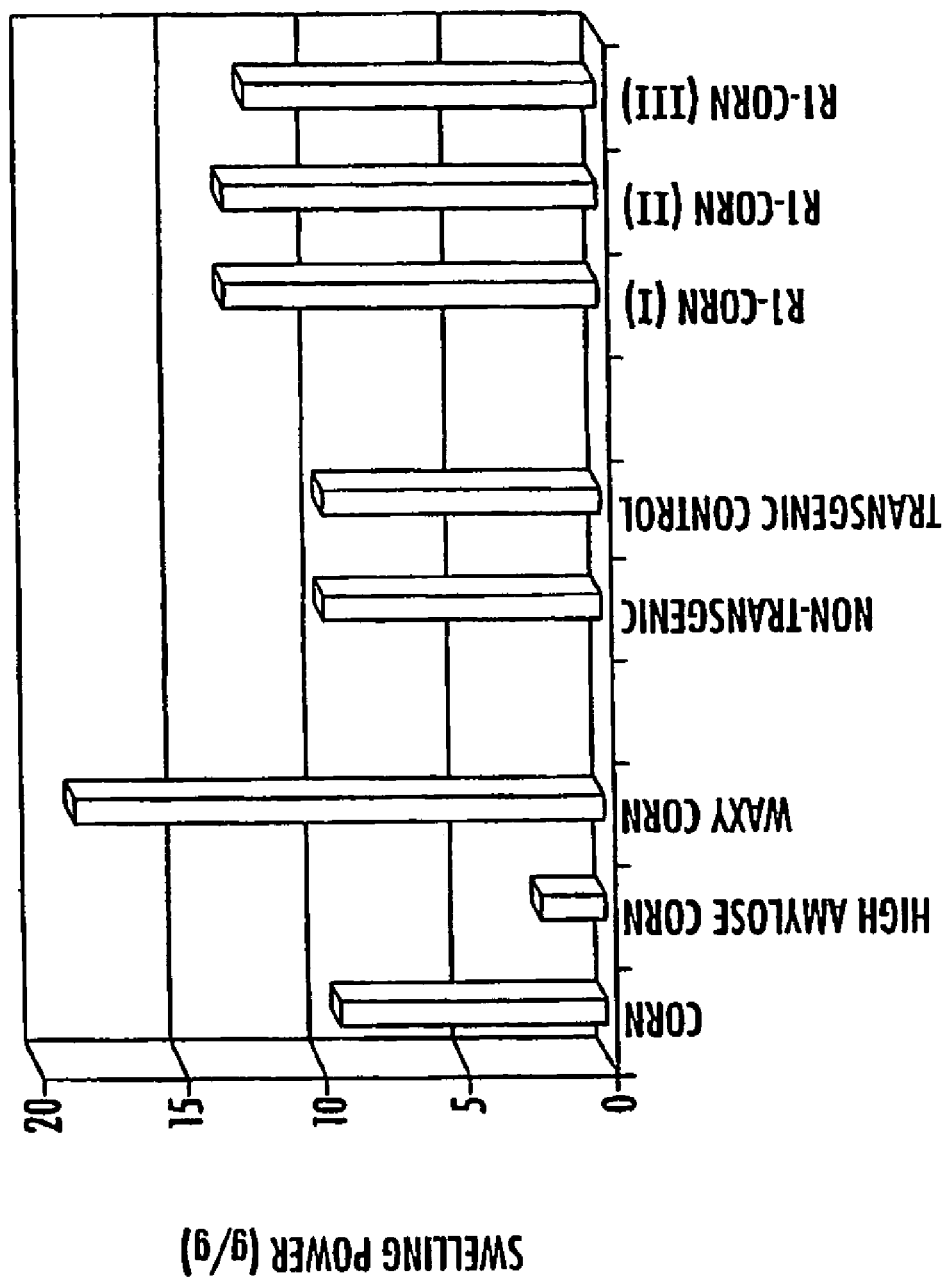
FIG. 4 shows the relative swelling-power of R1-cornstarch compared to non-transgenic cornstarch.
Figure 5:
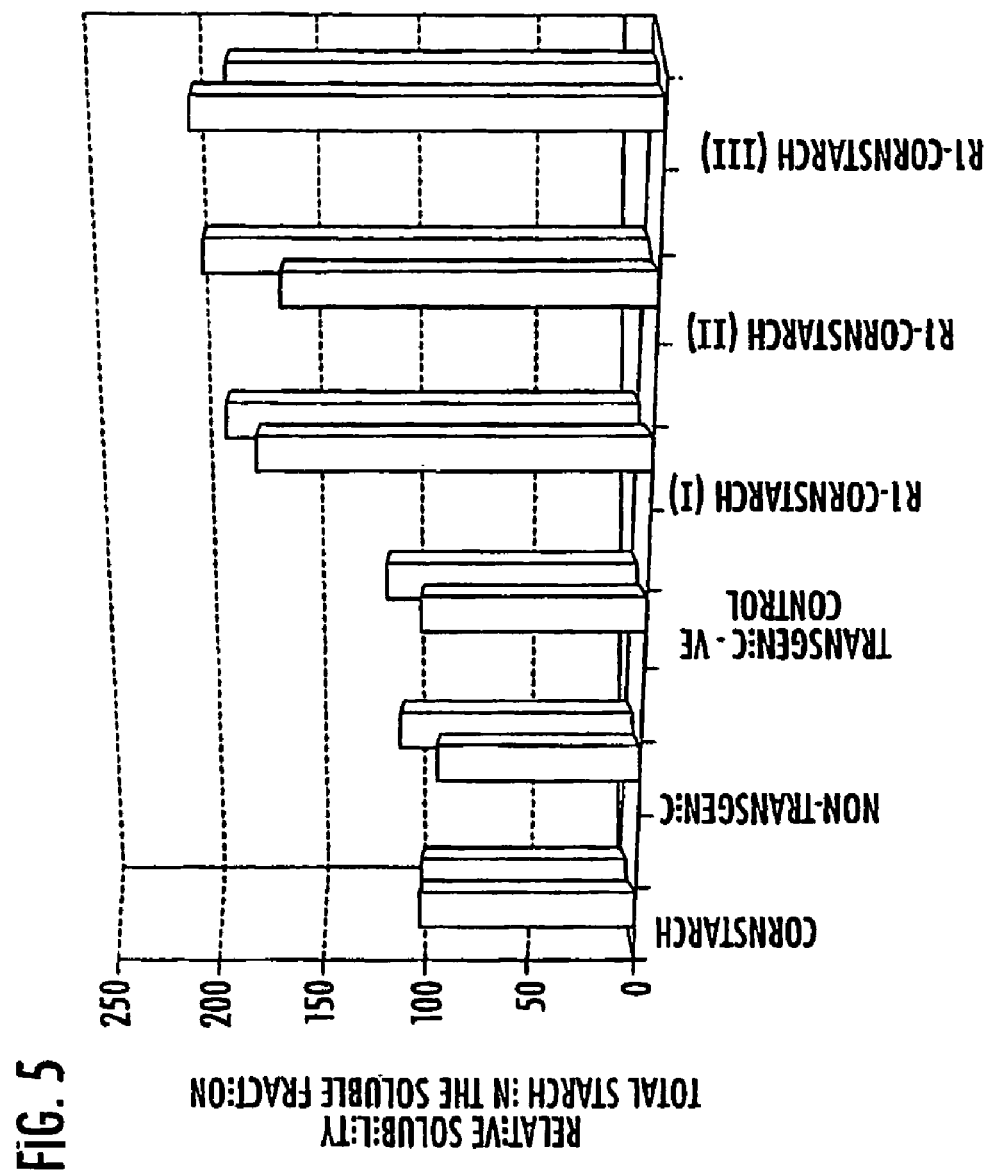
FIG. 5 shows the relative solubility of the R1-cornstarch compared to the non-transgenic cornstarch.

FIG. 4 shows the relative swelling-power of R1-cornstarch compared to non-transgenic cornstarch. The solubility of the starch samples were compared as follows. Starch sample (1% w/w) in 4.5 M urea was stirred for 30 minutes at 50° C. The mixture was centrifuged at 3000 rpm for 15 minutes. The supernatant was carefully removed. The starch present in the supernatant was estimated by Starch/Glucose estimation kit (Sigma) and by iodine staining. FIG. 5 shows the relative solubility of the R1-cornstarch compared to the non-transgenic cornstarch. Results from two independent set of experiment shown in the figure.

FIG. 5 shows the relative solubility of R1-cornstarch compared to non-transgenic cornstarch.

Phosphate, as a doubly-charged functional group, has high affinity for water; also, when covalently-bound to the glucose strands of starch the phosphate groups can assist swelling through electrical repulsion. Thus, by phosphorylating cornstarch its solubility in ionic solvents (including water) and its swelling power (e.g. in water) can be increased R1-cornstarch is a phosphorylated form of cornstarch, which usually is not phosphorylated. Hence, as expected, we observe increase in the swelling power (by 30-40%, FIG. 4) of R1-cornstarch (from T2 seeds of corn expressing potato R1 gene). The relative solubility (FIG. 5) of R1-cornstarch (from T2-seeds) also appears to be significantly higher than observed in case of non-transgenic control.

Susceptibility of R1-Corn to Enzymatic Hydrolysis.
Susceptibility to Hydrolysis Under Simulated Digestive Conditions:

The samples for the assay were prepared by passing ground-up corn flour (seeds grinded in Kleco) through a sieve having a 300 micron pore-size. The sample (500 mg) was treated, for 30 min at 37° C. (on a reciprocating shaker), with 5 ml of pepsin/HCl (2000 units/ml in 0.1 N HCl) solution in acidic pH, simulating gastric digestive conditions. The incubated reaction mixture was then neutralized with NaOH and the next step of digestion was carried out with 2.5 ml pancreatin (5 mg/m in 150 mM KPO4, pH 7.0 buffer). The tube was vortexed and incubated with shaking on the reciprocating shaker at low speed at 37° C. for 120 min. At the end of the incubation 7.5 ml of water was added to each tube and vortexed. The undigested portion of the corn flour was precipitated by centrifugation in a table-top centrifuge at 24° C., 4000 rpm for 30 min and the supernatant of the sample was heated at 100° C. for 15 minutes, allowed to cool, centrifuged and the supernatant was used to assay the amount of the total soluble sugar (measure glucose with BCA reagent after complete enzymatic hydrolysis of the sugar chain), small oligosaccharides (HPLC analysis described above) and glucose (BCA reagent) released due to digestion. The results obtained from different assay methods corroborated with each other. Shown in FIG. 6 is the HPLC analysis; the results clearly demonstrate an increase (10-20%) in the release of total small oligosaccharides (degree of polymerization 1-7) from R1-corn flour samples, as compared to the normal corn flour.

Figure 6:
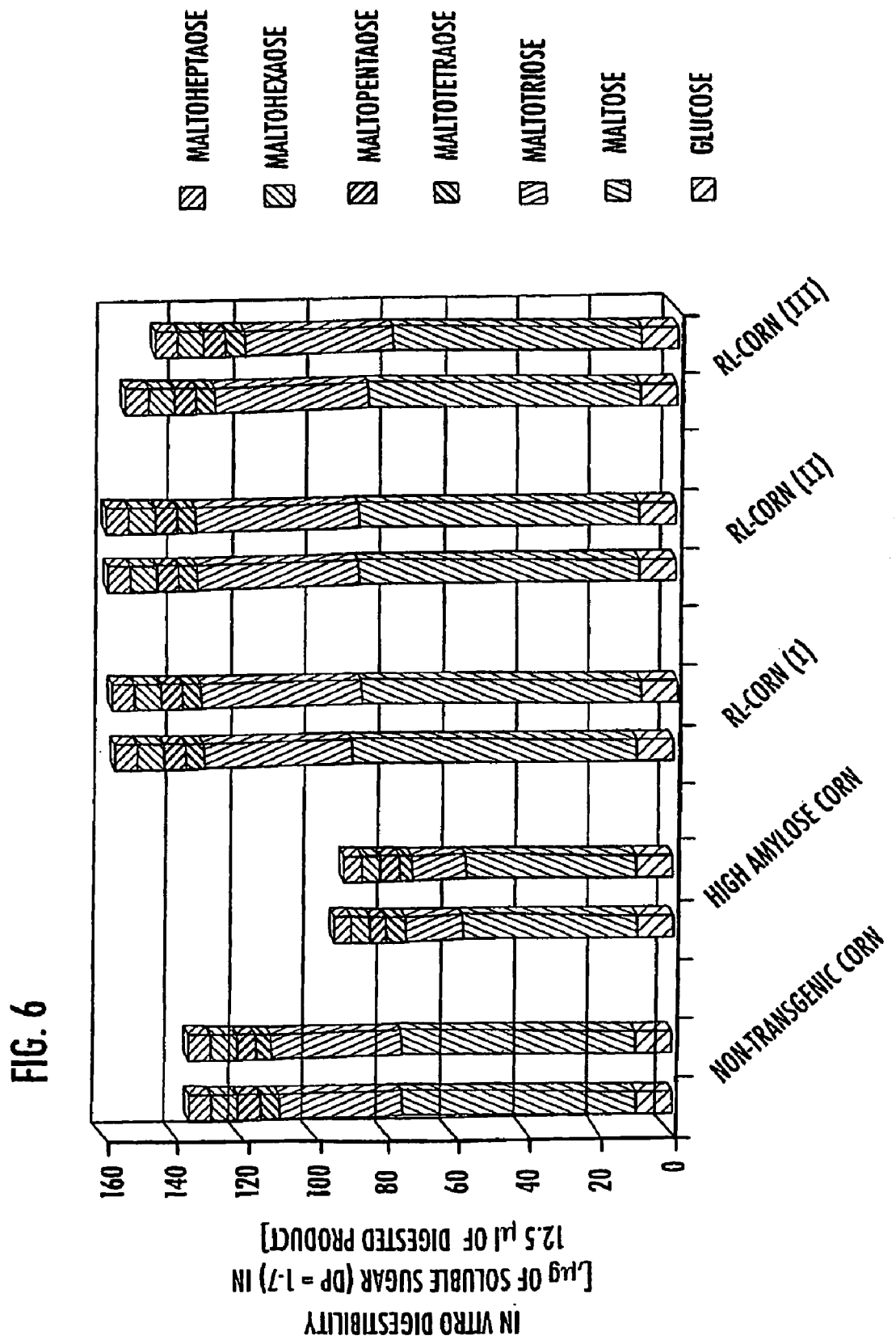
FIG. 6 shows an HPLC analysis demonstrating in vitro digestibility of R1-corn flour under simulated digestive conditions.

FIG. 6 demonstrates in vitro digestibility of R1-corn flour under simulated digestive conditions. The figure shows the pile-up of the glucose and other small (<8) oligosaccharides obtained at the end of the simulated GI-track digestion process. The sugars are estimated by integration of the peak-area in the HPLC analysis profile.

Susceptibility to Hydrolysis in Presence (In Vitro) of Different Starch Hydrolyzing Enzymes:

Enzymatic digestibility of R1-cornstarch in R1-corn flour was tested using three α-amylases from different sources and one glucoamylase. The corn flour samples for the assay were prepared by passing ground-up corn flour (seeds grinded in Kleco) through a sieve having a 300 micron pore-size. Corn flour (50 mg) suspended in 500 µl of 100 mM sodium acetate (pH 5.5) was used for each enzyme reaction. In all these enzymatic digestions the amount of enzyme used was below the level required for complete hydrolysis of the available starch in the sample. The reactions were carried out with or without pre-incubation in the absence of enzyme as indicated in the figure legends.

Figure 7A:
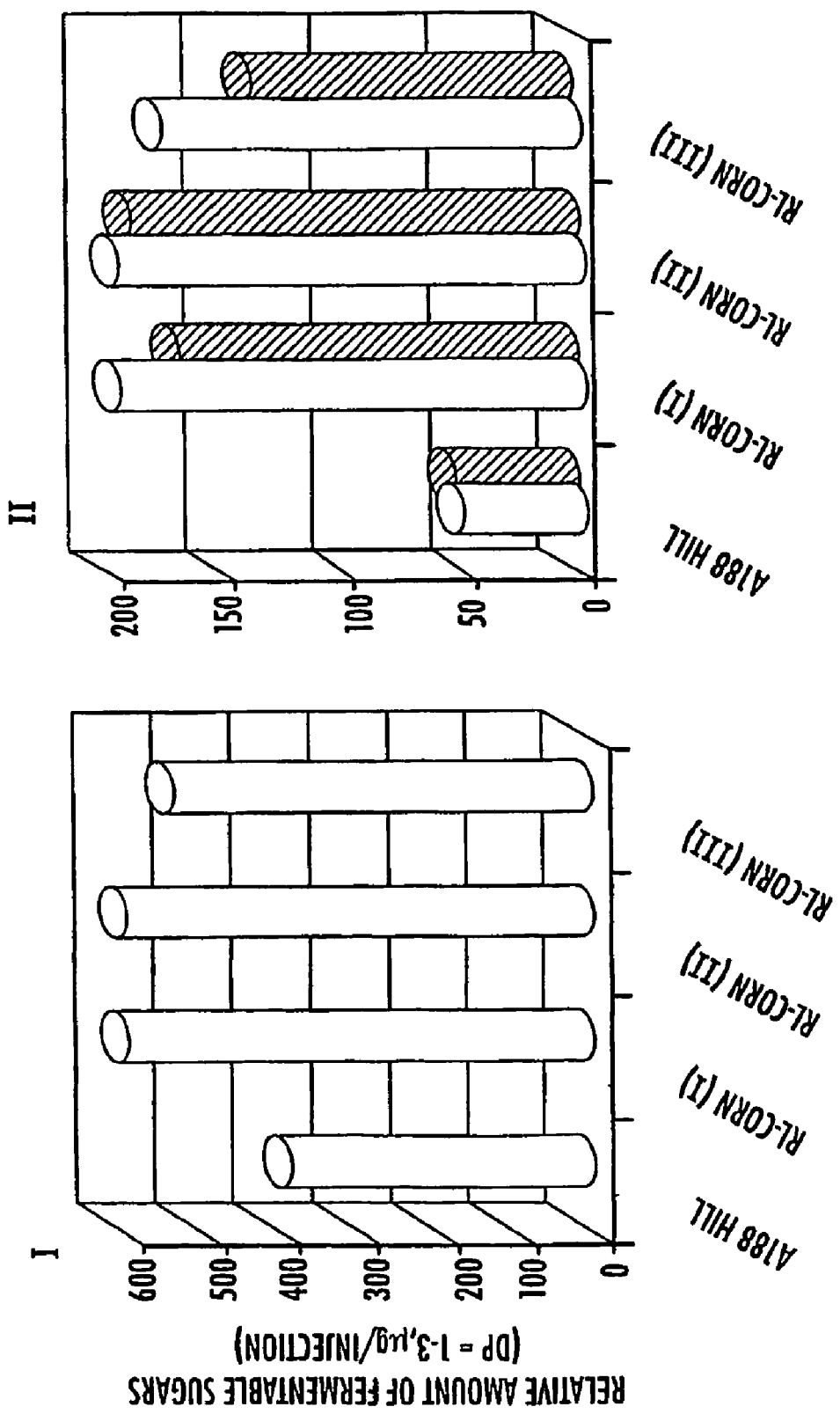
FIG. 7 shows the susceptibility of R1-corn flour to enzymatic hydrolysis by starch hydrolyzing enzymes.

FIG. 7 shows the susceptibility of R1-corn flour to enzymatic hydrolysis by starch hydrolyzing enzymes. For results depicted in FIG. 7A, corn flour sample in sodium acetate buffer was pre-incubated at 75° C. (I) at 60° C. or 25° C. (II) for 15 minutes. At the end of the pre-incubation, the samples were cooled down to room temperature, 10 µl of α-amylase from *Aspergillus oryzae* (Sigma) was added each reaction mixture, vortexted and the incubation for 30 minutes at room temperature was carried out with constant shaking. The reaction mixture was then centrifuged at 14000 rpm for 2 minutes, the supernatant was collected and heated at 95° C. to deactivate any residual enzyme, centrifuged and the supernatant was filtered through 0.4 micron filter to prepare sample for HPLC analysis (method described above). The figure depicts the relative amount of easily soluble fermentable glucose oligosaccharides (Degree of polymerization=1-3) released as a result of the enzymatic hydrolysis. The amount of fermentable sugars is the sum of amount of glucose, maltose and maltotriose product, estimated from the HPLC analysis (integration of peak area and comparison with calibration-curves generated with authentic sugars).

The difference in the relative susceptibility to hydrolysis is much more prominent when the corn-flour samples were not heated above the gelling-temperature (~70° C., during pre-incubation or incubation with enzyme) of cornstarch (FIG. 7).

For FIG. 7B, susceptibility of different corn flour samples towards a thermophillic α-amylase (expressed as transgene in corn) was carried out in similar manner as describe in case of *A. oryzea* α-amylase. Corn flour sample (non-transgenic control and R1-corn) was mixed with the flour from corn expressing the α-amylase in 10:1 ratio and incubated at 85° C., for 90 minutes (I), 3 hours (I) or 24 hours (II). The released soluble sugar analyzed and quantified by HPLC, as described previously.

For FIG. 7C, digestibility of non-transgenic corn and R1-corn samples (50 mg) towards o-amylase from barley (10 µl of purified enzyme, protein concentration 5 mg/ml) was measured by mixing enzyme after 15 minutes pre-incubation at room temperature. The reaction was carried out as described in case *A. oryzea* α-amylase. Incubation at room temperature was done for 30 minutes and 3 hours. The FIG. 7C I, shows the relative amount of soluble glucose oligosaccharides released after the enzymatic reaction; while the HPLC profiles generated for one of the R1-corn sample and the non-transgenic corn sample are shown in FIG. 7C II.

FIG. 7D shows the results of an experiment similar to those described above was also carried out with Glucoamylase from *Aspergillus niger* (Sigma) as the enzyme and non-transgenic corn or R1-corn sample (50 mg) as the substrate. Enzyme (50 or 100 units) was mixed with corn flour sample (in 100 mM sodium acetate buffer pH 5.5) that is pre-incubated at room temperature and the incubation was continued at room temperature for 60 minutes. The glucose released into the reaction mixture was analyzed by HPLC as described above. The FIG. 7D I, shows the relative amount of glucose produced after the enzymatic reaction; while the HPLC profile generated for the R1-corn and the non-transgenic corn samples are shown in FIG. 7D III (100 units of enzyme).

FIG. 8 shows the effect of incubation time and enzyme concentration on the rate of hydrolysis of R1-cornstarch.

Figure 8A:
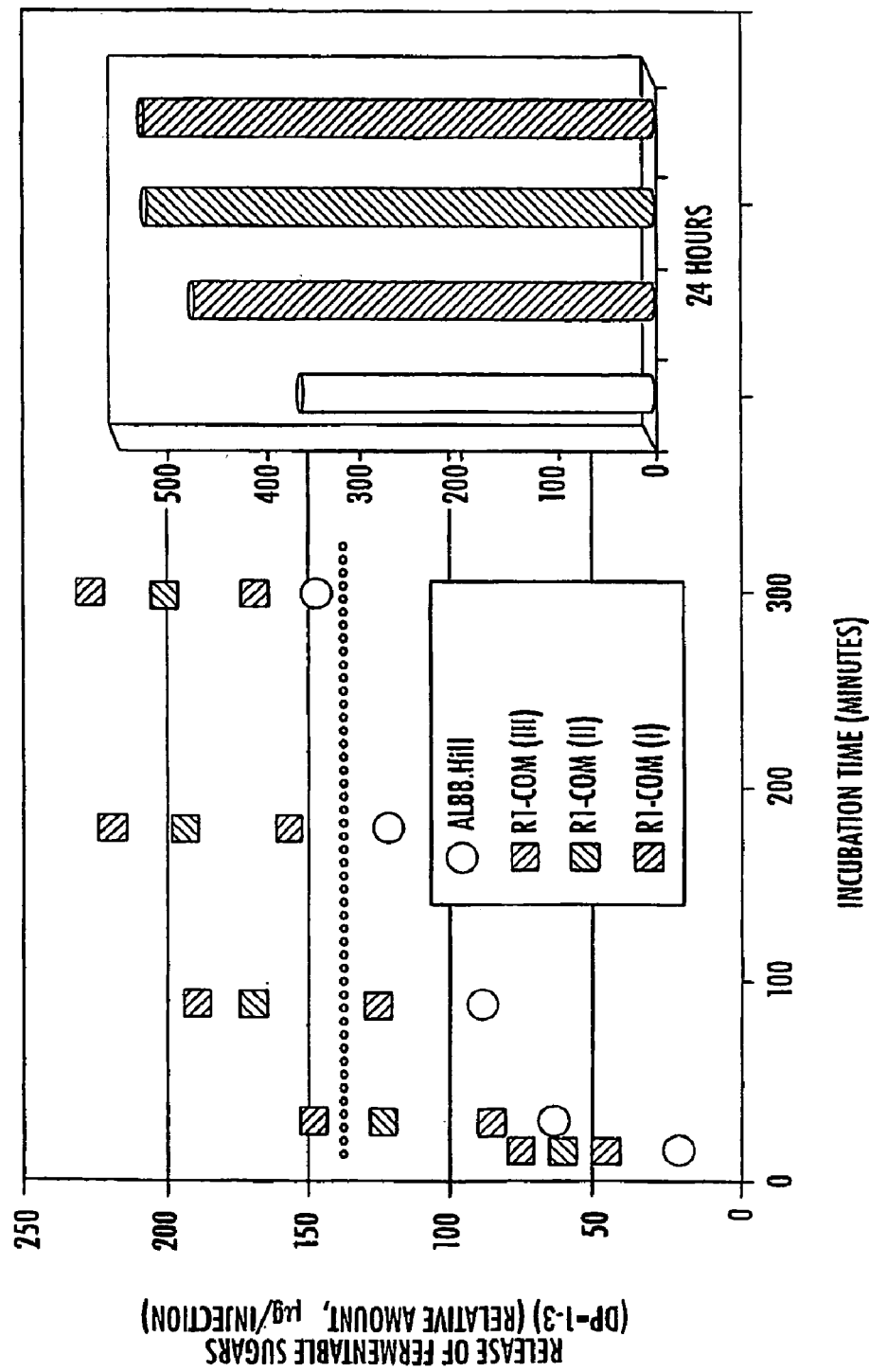
FIG. 8 shows the effect of incubation time and enzyme concentration on the rate of hydrolysis of R1-cornstarch.
Figure 8B:
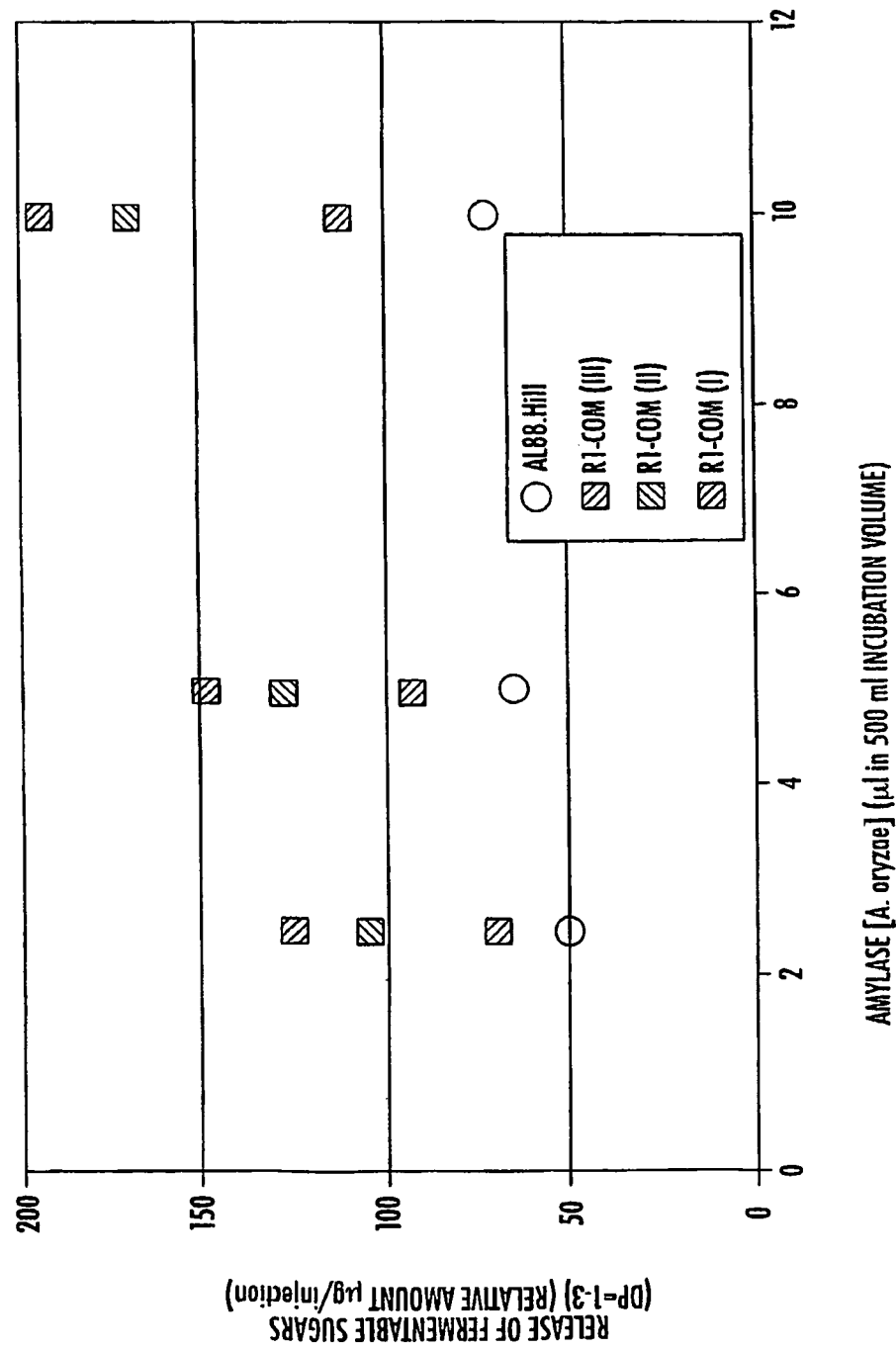

The experiment was carried out as described previously in case of FIG. 7A. The pre-incubation and incubation temperature is 25° C. (room temperature). The amount of enzyme [α-amylase (*A. oryzae*)] used to test the effect of incubation time on the hydrolysis is 10 µl in 500 µl of reaction volume (FIG. 8A). Incubation time for the experiment shown in FIG. 8B is 30 minutes. As shown above, covalent derivatization of starch with hydrophillic functional group(s) (e.g. phosphate, as in case of R1-cornstarch) increases its swelling as well as solubility in aqueous medium, making the modified starch molecules more accessible to hydrolytic enzymes. Hence, the use of such a derivatized form of starch not only will increase the proportion of starch available for enzymatic degradation it possibly can also increase the rate of hydrolysis. Here, this hypothesis is tested using phosphorylated cornstarch that was made in transgenic corn plant by expressing R1-protein gene from potato in the endosperm of corn.

As shown in FIG. 6, the R1-cornstarch (in corn flour) is comparatively more digestible (as measured by the in vitro assay) compared to normal cornstarch (non-transgenic). In this in vitro assay effort has been made to mimic the enzymatic reaction conditions found in the digestive track of mono-gastric animal. A difference of more that 10-15% was found between the R1-corns samples and the control non-transgenic corn.

Compared to cornstarch, R1-cornstarch is also more susceptible to attack by all the starch hydrolyzing enzymes tested (FIGS. 7 & 8). This again is consistent with the idea that R1-starch, being phosphorylated, swells and hydrates more (compared to normal cornstarch, which is not phosphorylated) in aqueous solution, making the R1-starch molecules more accessible to attack by hydrolytic enzymes. Collectively the experiments described in FIGS. 7 & 8 demonstrate that the R1-cornstarch in corn flour is hydrolyzed at a faster rate compared to non-transgenic control. Thus, same amount of fermentable/soluble glucose oligosaccharides can be released from R1-cornstarch by using less amount of enzyme and/or with shorter period of incubation that that is required for non-transgenic control starch.

It should be also noted that the difference in the relative susceptibility to hydrolysis was more prominent when the corn-flour samples were not heated above the gelling-temperature (~70° C., during pre-incubation or incubation with enzyme) of cornstarch (FIG. 7).

Example 5

Fermentability of R1-Corn Starch

Fermentation procedure: Corn flour sample of the transgenic and non-transgenic corn were prepared by grinding corn kernel to a fine powder (>75% of the weight passes a 0.5 mm screen) using a hammer mill (Perten 3100). The moisture content of the corn flour samples were determined using a Halogen Moisture Analyzer (Metler). Typically the moisture content of the samples ranges between 11-14% (w/w). Corn flour samples were weighed into 17×100 mm polypropylene sterile disposable culture tubes. The approximate weight of the dry sample is 1.5 g per tube. In each tube 4 ml water was added and the pH is adjusted 5.0. Each samples were inoculated with ~1×10$^7$ yeast/g flour. [The yeast (EDT Ferminol Super HA-Distillers Active Dry Yeast) inoculum culture was grown in Yeast starter medium (300 ml containing 50 g M040 maltodextrin, 1.5 g Yeast extract, 0.2 mg $ZnSO_4$, 100 µl AMG300 glucoamylase and ml of tetracycline (10 mg/ml)). The medium was inoculated with 500 mg yeast and incubated at 30° C. for 16 h, with constant shaking.] The inoculation was followed by addition of 0.5 ml of yeast extract (5%), 1.5 ml water, 0.03 ml 0.9 M sulphuric acid and Glucoamyalse (*Aspergillus niger*) Sigma A7095-50 mL. The final fermentation mixture is adjusted to 33% solid. The fermentation tubes were weighed and incubated at 30° C. The tubes were weighed, without mixing, at intervals (at least once/24 h) weigh the tubes. Aliquot of samples were also taken out from the fermentation tubes (after mixing) at regular interval (every 24 hours) for estimation of ethanol production HPLC analysis (described below).

HPLC-analysis of the fermentation products. This method is used to quantify the ethanol and other fermentation products produced during the corn fermentation process. Waters 2695 Alliance HPLC System equipped with binary pump and temperature controlled auto sampler; Waters 2414 Refractive Index Detector and a Column Heater from Eppendorf were used for the analysis.

Chromatography Conditions:

Column Type: Bio-Rad Aminex HPX-87H (300×7.8 mm)

Column Temperature: 50C

Detector Temperature: 35C

Sample Temperature: 6-11C

Mobile Phase: 0.005 M Sulphuric Acid in HPLC grade water

Flow rate: 0.6 mL/min

Isocratic

Run Time: 30 minutes

A 5-point calibration curve is generated and used to quantitate ethanol and other fermentation products. For calibration the various compounds (Maltodextrin M 100 (DP 4+), Maltotriose (DP 3), Maltose, Glucose, Fructose, Lactic Acid, Glycerol, Acetic Acid and Ethanol are weighed or pipetted into a 100 mL volumetric flask and diluted to volume with 0.02% Azide in HPLC grade Water. Standards: A 25 μL of Std-0%; Std-5%; Std-10%; Std-15% and Std-20% are injected to make the 5-point calibration curve. Std-0 is the blank. Sample: A 25 μL sample fermentation mixture (after centrifugation at 14,000 rpm for 5 minutes and filtering through 0.2 micron filter) is injected.

Figure 9A:
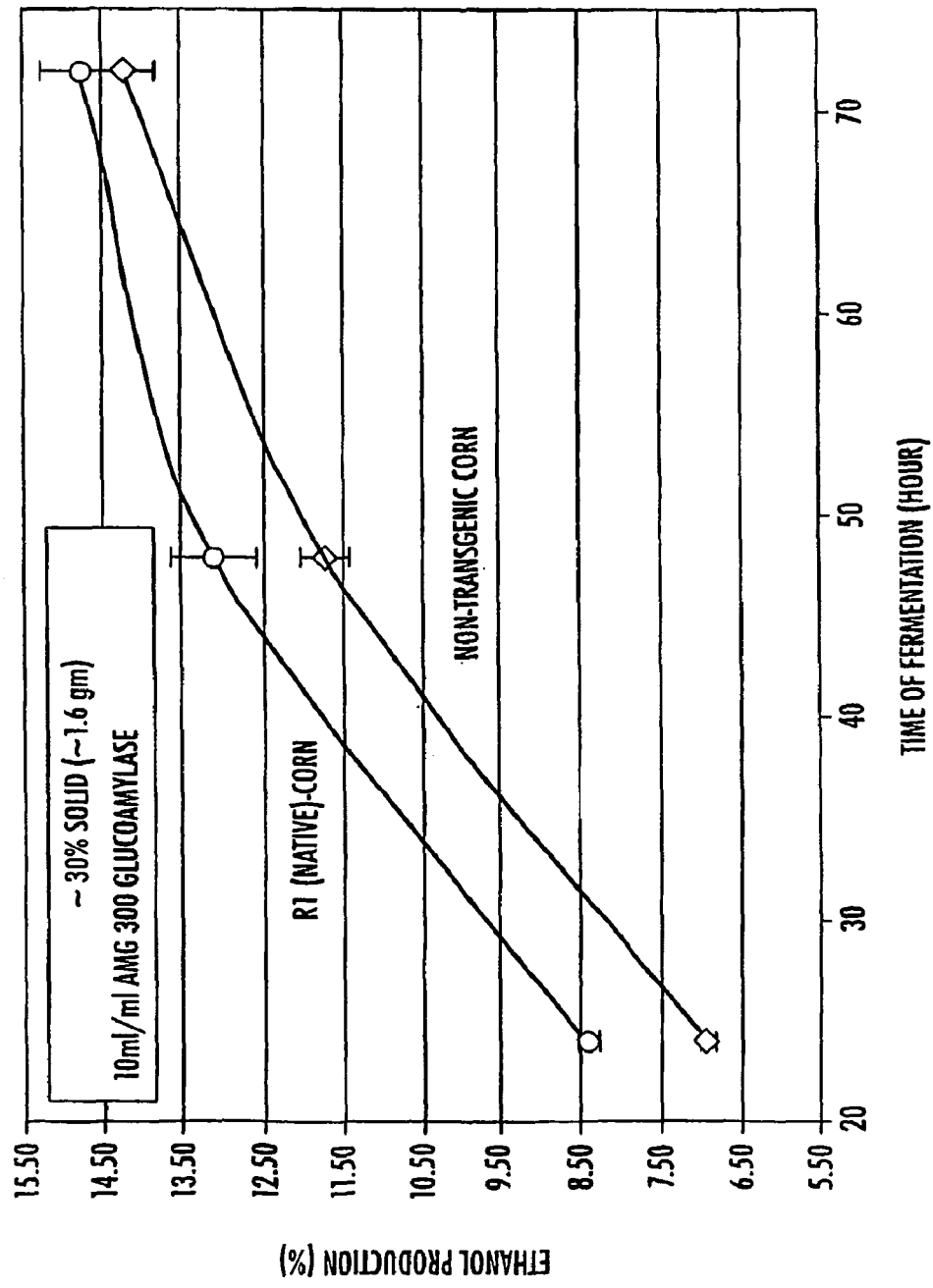
FIG. 9 demonstrates the fermentability of R1 cornstarch.
Figure 9B:
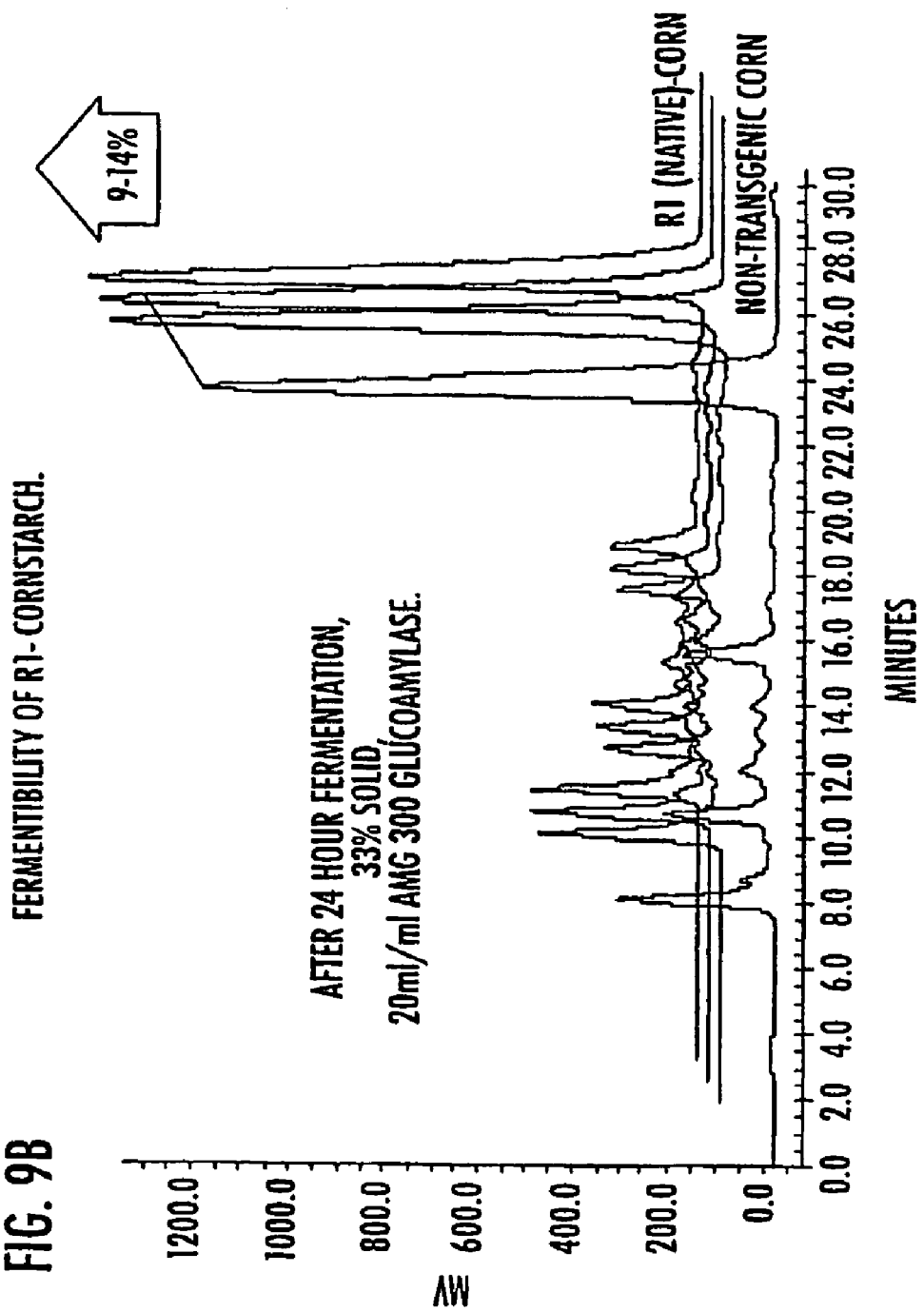

FIGS. 9A & 9B show the results obtained with samples of transgenic corn expressing potato native R1-gene; these results being compared to the non-transgenic control, We found that the transgenic samples performed better (~9-14% at 24 hours) in the fermentation process with regard to the ethanol production; this trend continued for at least 72 hours of fermentation, although the trend appeared to decrease with the progress of the time of incubation. Consistent with this observation we also find that the percent weight change per unit dry weight also higher (1-3%) in case of transgenic R1-corn, compared to the control.

This find is consistent with the our hypothesis that the phosphorylated form of corn starch due to its higher swelling power and solubility in water can easily targeted by hydrolytic enzymes. This will lead to efficient hydrolysis of the phosphorylated starch, at a faster rate and/or using lesser amount of enzyme, compared to normal non-phosphorylated starch. The efficient hydrolysis and efficient release of fermentable sugar enables increase yield in ethanol production, as demonstrated here. This result may be extrapolated for other kinds of fermentation products (lactic acid, glycerol etc.).

Example 6

Phosphorylated Starch from the Transgenic-Corn Expressing Synthetic Version of Maize-Codon Optimized Potato R1-Gene The isolation procedure for starch from corn kernel, mild acid-hydrolysis of the isolated starch samples, glucose and glucose 6-phosphate estimation were carried out as described previously.

FIG. 10A provides an estimation of glucose 6-phosphate after complete hydrolysis of starch. Increased phosphorylation of R1 (synthetic)-cornstarch. Starch samples (~100 mg) isolated from the corn kernels (T1 seeds) of different events (transgenic synthetic R1-corn) were completely hydrolyzed (mild-acid hydrolysis, as described above) to glucose. The glucose and glucose 6-phosphate in the hydrolysates were quantified as described above. FIG. 10A shows the relative level of phosphorylation of the starch in different samples, as measure by the glucose 6-phosphate dehydrogenase assays and normalized with respect to the estimated glucose in the samples.

Screening of different synthetic R1-transgenic corn events using method above described method indicated high level of in planta phosphorylation of starch in corn expressing potato R1 (synthetic)-transgene. The starch sample isolated from non-transgenic corn is not phosphorylated, as it is hardly detectable by this assay. The level of phosphorylation that is observed in case of maize-codon optimized synthetic R1-cornstarch considerably more than the level that is observed in transgenic corn expressing native potato R1 gene. It is to be noted that this assay particular method detects the phosphorylation at the 6-position only, phosphorylation at any 3-position of glucose residue of starch is not detectable by this method.

HPLC assay to quantify and detect Glucose 6-phosphate and Glucose 3-phosphate. In order to detect and quantify Glucose 6-phosphate and glucose 3-phosphate in the hydrolysate of the starch samples HPLC assays was carried out using Dionex DX-500 BioLC system consisting of: GS-50 Gradient Pump with degas option; ED 50 Electrochemical Detector; AS-50 Thermal Compartment; AS-50 Autosampler Chromatography conditions are:

1. Column Type:CarboPac PA 10 Analtyical (4×250 mm)
2. Detector Temperature: Ambient
3. Sample Temperature: Ambient
4. Eluents: A: Water B: 300 mM NaOH C: 1M NaOAC
5. Flow rate: 1.0 mL/min
6. Program:

| Time(min) | A (%) | B (%) | C (%) |
|---|---|---|---|
| 0 | 87.5 | 12.5 | 0.00 |
| 15.0 | 85.50 | 12.50 | 2.00 |
| 15.10 | 85.50 | 12.50 | 2.00 |
| 25 | 0.00 | 60.00 | 40.00 |
| 30.0 | 0.00 | 60.00 | 40.00 |
| 33.5 | 0.00 | 0.00 | 100.00 |
| 36.5 | 87.50 | 12.50 | 0.00 |
| 43.0(End) | 87.50 | 12.50 | 0.00 |

7. Detection (ED40): Pulsed amperometry, gold electrode. Waveform for the ED40:

| Time(s) | Potential(V) | Integration |
|---------|--------------|-------------|
| 0.0     | 0.05         |             |
| 0.20    | 0.05         | Begin       |
| 0.40    | 0.05         | End         |
| 0.41    | 0.75         |             |
| 0.60    | 0.75         |             |
| 0.61    | −0.15        |             |
| 1.00    | −0.15        |             |
| 0.20    |              |             |

D-Glucose-6-phosphate Dipotassium salt and Glucose 1-phosphate (Sigma) was used as the standards. A 5-point calibration curve is generated and used to quantify the level of glucose 6-phosphate.

FIG. 10B shows the elution profiles of some Dionex HPLC analysis of hydrolysates of starch samples from transgenic and non-transgenic corn and from potato. The second peak adjacent to the Glucose 6-phosphate peak is probably due to the presence of glucose 3-phosphate (this chromatography procedure was able to distinctly separate Glucose 6-phosphate and Glucose 1-phosphate) in the hydrolysates. A higher level of starch phosphorylation was observed in transgenic corn (segregating corn kernel from T1 seeds) expressing codon-optimized synthetic R1-gene compared to the starch samples isolated from transgenic corn expressing native potato R1-gene.

Example 7

Identification and Cloning of *Chlamydomonas Renhardtii* Glucan Dikinase

This example describes the methods used to identify and clone the *Chlamydomonas* glucan dikinase using sequence homology to the R1 potato gene. A Contig: 20021010.4244.1 from the *Chlamydomonas* genomic sequence was found to code (794 bp) for a portion of a protein that is homologous to the C-terminal of the R1 gene product. It had Identities=96/180 (53%), Positives=125/180 (69%), and score 178 and E-value of 7e-44. Then a Scaffold of 72677 bp was found in the *Chlamydomonas reinhardtii* genome. From the scaffold, a 4074 bp coding sequence was derived (exons without putative introns). Analysis of the predicted amino acid sequence revealed an N-terminal starch binding domain, the conserved histidine (catalytic site) and C-terminal homology to pyruvate dikinases. The potato R1 gene product (1464 amino acids) compared to the *Chlamydomonas* putative glucan dikinase (1357 amino acids) showed: Identities=467/1387 (33%), Positives=722/1387 (51%), Gaps=150/1387 (10%), Score=699 bits (1803) and Expect=0.0.

The cDNA gene for the putative *Chlamydomonas* glucan dikinase gene was cloned using PCR and using the *Chlamydomonas* cDNA library from Duke University.

081503-1:
(SEQ ID NO: 4)
5'-CATATGGGGATAGACGCTGCCGGGCTGGACACCAACGG 081503-2:
(SEQ ID NO: 5)
5'-GAATTCCTACACCTGCGGGCGCGTCTGCACAACGGTGATGGC 081503-3:
(SEQ ID NO: 6)
5'-GGATCCCCGGCTCCTGCCGCGGCTACCTGGGC 081503-4:
(SEQ ID NO: 7)
5'-GGATCCTGTTGCCGGCGGCGCTGGCGCTGGCGG

Primers 081503-2 and 081503-3 were used to get 3'-end fragment (~2 kb) of the coding region. Amplified from cDNA library using Advantage GC-2 kit PCR mixture (Clonetech). PCR cycle: 94° C. 3 min-[94° C. 30 sec-68° C. 3 min] 35 cycle-68° C. 3 min.

(SEQ ID NO: 8)
082803-1: 5'-GCTGGAGCTGAAGGAGACCAG (SEQ ID NO: 9)
082803-2: 5'-GGTGTTCTGCGAGCTGGTCAAGG (SEQ ID NO: 10)
082803-3: 5'-GATCCGGAGGGCTGCGTGGCCC (SEQ ID NO: 11)
082803-4: 5'-GCCACCAACACCTGGTACG (SEQ ID NO: 12)
082803-5: 5'-GACGAGCTGTGGCGCGTGGCG (SEQ ID NO: 13)
082803-6: 5'-CGCAGGAGTGGGTGCGC (SEQ ID NO: 14)
082803-7: 5'-CTGGCGTGTGCTGTCGGACGCAG

Primers 082803-6 and 081503-2 were used to get 3'-end fragment (~2.5 kb) of the coding region. Amplified by gradient PCR from cDNA library using Advantage GC-2 kit PCR mixture (Clonetech). PCR cycle: 95° C. 3 min-[94° C. 30 sec-50-68° C. 1 min] 40 cycle-68° C. 3 min.

(SEQ ID NO: 15)
091103-1: 5'-CCCGAGGACCTGCTGGGCGTGC (SEQ ID NO: 16)
091103-2: 5'-AGTCATCAACGACCAGCTGGCGG (SEQ ID NO: 17)
091103-3: 5'-CGTACCGCGCCCAACCTGTCTGCCG (SEQ ID NO: 18)
091103-4: 5'-GCTCCCGCGAGTGGGTGATGCCGGACG (SEQ ID NO: 19)
091103-5: 5'-ACCACCACCTGGGTGCGCTGCTG

RT-PCR product using primers 082803-7 & 082803-4 (~1.5 kb). This fragment was cloned and sequenced. Sequence showed that the cloned fragment constitutes part of the Chlamy glucan dikinase coding sequence (predicated from the genomic sequence), but this clone is still missing the small fragment of the 5'-end of the coding sequence.

Primers for 5' RACE using Clonetech SMART RACE kit.

(SEQ ID NO: 20)
100103-1: 5'-TGGGCGTGCCAGCGCGCGAGGCAGC (SEQ ID NO: 21)
100103-2: 5'-TCTTCCGGTAGTCCGAGTACTTCCACTTGCCC

Did not produce positive result.

Primers for Stitch PCR used to join the ~2.5 and ~1.5 kB fragments; to produce ~4 kb fragment encoding almost the full length coding sequence.

```
                                                  (SEQ ID NO: 22)
100203-1: 5'-CCCGACGACGTGCCCATCTGCGAGGCCTACC (SEQ ID NO: 23)
100203-2: 5'-GGTAGGCCTCGCAGATGGGCACGTCGTCGGG
```

Amplified using Advantage GC-2 kit PCR mixture (Clonetech). PCR cycle: 95° C. 3 min-[94° C. 30 sec-62° C. 30 sec-68° C. 1 min] 15 cycle-68° C. 3 min. The ~4 kb fragment cloned into Topo 2.1 and transformed into DH5α cells Primers used for sub-cloning into pET 22b vector at NdeI and EcoR1 sites.

```
                                                  (SEQ ID NO: 24)
121703-1: 5'-CATATG GACGACGCCACCAACACCTGGTACGATGAC (SEQ ID NO: 25)
121703-2: 5'-GAATTCTACACCTGCGGGCGCGTCTGCACAACGG
```

Example 8

Isolation of Glycogen from E. Coli

E. coli 50 gm (15 gm) were suspended in 200 ml (60 ml) of 50 mM glycylglycine buffer, pH 7.0 (7.25) and sonicated for 3.5 min, at 10° C. The sonic extract was centrifuged for 90 min at 104,000× g (Rotor 50.2 30,000 rpm for 90 min). The glycogen particles were suspended in 150 ml (45 ml) of distilled and de-ionized water. The suspension heated in boiling water bath for 5 min and centrifuged at 18,000× g at room temperature (18,000× g in 25.5 rotor for 20 min). The resultant precipitate was washed with 20 ml (10 ml) of water, and the wash and supernatant were pooled. A 0.1 volume of 50% TCA (50 g of TCA in 22.7 ml water=100% TCA) solution was added, and the solution was placed on ice for 10 min. the precipitated by centrifugation at 18,000× g for 10 min and then washed with 20 ml of 5% TCA. The wash was pooled with the supernatant fluid. Then 1.5 volumes of absolute ethanol were added to the combined solution, and after 20 min the glycogen precipitate was isolated by centrifugation (10 min at 18,000× g) and dissolved in water. An equal volume of cold absolute ethanol was added, and the suspension was kept overnight at 4° C. The precipitate was collected by centrifugation, re-dissolved in water, and re-precipitated twice with equal volume of ethanol in the same manner. The final alcohol precipitate was washed with acetone and the dried in vacuo.

Example 9

Determination of Phosphate Esterified at the C-6 Position of the Glucose Residues of Starch or Glycogen for In Vitro Measurement of Glucan Dikinase Activity Nielsen, T. H., Wichmann, B., Enevoldsen, K., and Moller, B. L. Plant Physiol. (1994) 105, 111-117.

Suspend starch or glycogen (100 mg) in 0.5 ml of 0.7 N HCl and kept at 95-100° C. for 2-4 hours for mild acid hydrolysis (do not let caramelization/browning to take place). Mix an aliquot (100 μl) with 400 μl of buffer containing 100 mM MOPS-KOH (pH 7.5), 100 mM $MgCl_2$, 2 mM EDTA in a cuvette and then added (neutralize with) ~80 μl of 0.7 N KOH. Add NAD (final concentration 0.4 mM) and 2 unit of Glucose 6-Phosphate dehydrogenase, in a final assay volume of 0.5 mL. Measure change in absorption at 340 nm for 1-2 minutes. Report the change (linear increase) in absorbance during the first 30 sec as the rate of the reaction, which is proportional to the amount of glucose 6-phosphate or the measure of the starch or glycogen phosphorylation at the 6-position. Standard curve is generated using Glucose 6-phosphate. Total starch or glucose released after complete hydrolysis is estimated as described below. The relative amount of Glucose 6-phosphate in starch is normalized with respect to the estimated glucose.

The second method for estimating the Glucose 6-phosphate is by HPLC (please refer to the "Dionex Operation Procedure").

The results of the in vitro measurements shows that the *Chlamydomonas* gene encodes for a protein having the expected glucan dikinase activity showing phosphorylation of *E. coli* glycogen using Quantitative Glucose-6-P dehydrogenase assay and the HPLC assay.

TABLE 2

Phosphorylation of glycogen quantitation using Glc-6-P Dehydrogenase Assay.

|  | Glycogen bound phosphate (nmol Glc 6-P/mg glycogen) |
|---|---|
| *E. coli* - vector control | 1.0 ± 0.2 |
| *E. coli* - expressing *Chlamydomonas* gene | 6.1 ± 0.6 |

TABLE 3

Phosphorylation of glycogen Quantitation using HPLC assay

|  | Glycogen bound phosphate (nmol. Glc-6-P/mg glycogen) |
|---|---|
| *E coli* - vector control | 1.6 ± 0.8 |
| *E. coli* - expressing *Chlamydomonas* gene | 9.8 ± 0.6 |

Example 10

C. Enzymatic Quantification of Starch or Glycogen

1. *Amer. Assoc. Cereal Chemists, Approved Methods*, 9th edition, Method 76-13 (1995).
2. Karkalas, J., *J. Sci. Food Agric.*, 36, 1019-1027. (1985)
3. Beutler, H. O., *Methods of Enzymatic Analysis*, H. U. Bergmeyer, ed. New York, Academic Press, 3rd edition, volume 6, 2-10 (1984).
4. MacRae, J. C., *J. Sci. Fd. Agric.* 25, 1465-1469 (1974).
5. Thivend, P. Mercier, C. and Guilbot, A., *Methods in Carbohydrate Chemistry*, volume 6, 100-105 (1972).
6. Bergmeyer, H. U. and Bernt, E., *Methods of Enzymatic Analysis*, H. U. Bergmeyer, ed. New York, Academic Press, 3rd edition, pp 1205-1212.
7. *Official Methods of Analysis of the AOAC*, 16th Edition (1965) section 32.2.05. and 44.7.12.
8. Raabo, E. and Terkildsen, T. C., *Scand. J. Clin. and Lab Investigation*, 12, 402-407 (1960).
9. Wasko, M. E. and Rice, E. W., *Clinical Chemistry* 7, 542-545 (1961).

The level of phosphorylation of glycogen/starch was normalized with respect to the total amount of starch or glycogen sample used for analysis—for this we quantify the starch or glycogen in the sample using the assay kit from SIGMA Chemical company (St. Louis, Mo.). Alternatively, other methods cited above could be used.

Assay kit available from SIGMA.

The hydrolysis of starch to glucose is catalyzed by amyloglucosidase. Glucose is oxidized to gluconic acid in the reaction catalyzed by Glucose Oxidase. Hydrogen peroxide released during the reaction changes the colorless o-Dianisidine to brown oxidized o-Dianisidine in presence of Peroxidase. The intensity of the brown color measured at 425-475 nm is proportional to the glucose formed by starch hydrolysis.

STARCH+(n−1)H$_2$O—Amyloglucosidase→n Glucose

Glucose+H$_2$O+O$_2$—Glucose Oxidase→Gluconic Acid+H$_2$O$_2$

H$_2$O$_2$+o-Dianisidine(colorless)—Peroxidase→o-Dianisidine(brown)

Please, refer to the instruction manual of the kit for details of the protocol. Instead of carrying out digestion of starch with amyloglucosidase, complete hydrolysis of starch to glucose can be achieved using 0.7 N HCl (incubation for 4 hours at 95-100° C.). Note that the hydrolysate has to be neutralized with NaOH (0.7 N) before continuing with the enzymatic reactions.

Example 11

Glucan Dikinase Assay for In Vivo Measurement of Glucan Dikinase Activity

Ritte G, Lloyd J R, Eckermann N. Rottmann A, Kossmann J, Steup M. The starch-related R1 protein is an alpha-glucan, water dikinase. Proc Natl Acad Sci USA. 2002 May 14; 99(10):7166-71.

Materials: Amylopectin from potato and corn (Sigma), glycogen from bovine liver (Sigma), and amylose from potato (Sigma), myokinase (EC 2.7.4.3) from rabbit muscle (Sigma), pyruvate kinase (EC 2.7.1.40) from rabbit muscle (Sigma), and phosphorylase a (EC 2.4.1.1) from rabbit muscle (Sigma). [γ-$^{33}$P]ATP were purchased from NEN.

Synthesis of a Glucan Substrate for Glucan dikinase by Chain Elongation of Glycogen ("Elongated Glycogen"): Twenty milligrams of glycogen dissolved in 18 ml of 50 mM Hepes-KOH (pH 7.5), 1 mM EDTA, 40 mM glucose-1-phosphate (G1P), and 10% glycerol were incubated with 22 units of phosphorylase for 20 min at 25° C. Phosphorylase was then inactivated by heating for 10 min at 100° C. The polyglucan was precipitated by adding EtOH to a final concentration of 60%. Following centrifugation, the polyglucan was washed twice by resuspension in 24 ml of water and precipitation as above.

Glucan dikinase Activity Assay.

The activity assays (final volume 0.5 ml) were performed in buffer C [50 mM Hepes-KOH (pH 7.5)/1 mM EDTA/6 mM MgCl$_2$/10% glycerol] that was supplemented with polyglucans. Reactions were started by adding E. coli extract (50-100 μl in buffer B, (50 mM Hepes-KOH (pH 7.5)/1 mM EDTA/1 mM DTE/0.5 mM PMSF/10% glycerol)). In negative control samples enzyme fraction was replaced by an equal volume of buffer B.

Radioactive Assays.

A mixture of [γ-$^{33}$P]ATP and [β-$^{33}$P]ATP is used as the radioactive substrate in the assay. [γ-$^{33}$P]ATP and [β-$^{33}$P]ATP mixture was prepared by mixing 5 μl of [γ-$^{33}$P]ATP with 350 μl of a buffer that contained 50 mM Hepes-KOH (pH 7.5), 1 mM EDTA, 10% glycerol, 5 mM MgCl$_2$, 5 mM KCl, 0.1 mM ATP, and 0.3 mM AMP. The formation of [β-$^{33}$P]ADP was initiated by the addition of 2.4 units of myokinase. Following the incubation for 25 min at 37° C., the reaction was terminated by heating for 10 min at 95° C. and filtration through a 10-kDa filter (Microcon YM-10, Amicon). [β-$^{33}$P]ADP was then converted to [β-$^{33}$P]ATP by adding 0.86 mM PEP and 2 units of pyruvate kinase. After 20 min incubation at 37° C. the reaction was heat terminated. The glucan dikinase reaction mixture was incubated at 25° C. and was then terminated by heating for 10 min at 95° C. The polyglucan was separated from the soluble components (including the labeled ATP) by use of centrifugal filter units (Microcon YM-10; see above). 230 μl of the suspension were mixed with 270 μl of 2 mM cold ATP and passed through the 10-kDa filter by centrifugation (30 min, 14,000× g). The polyglucan that remained on top of the filter was further washed four times by resuspension in 450 μl of cold 2 mM ATP solution and subsequent centrifugation. Finally the filter unit was placed in a scintillation vial, scintillation fluid was added, and the vial was vortexed vigorously for 10 seconds before the incorporated radioactivity was determined in a scintillation counter.

The results of the in vivo glucan dikinase assay are set forth below in Table 4. It shows that the E. coli glycogen was phosphorylated in vivo in the presence of the Chlamydomonas glucan dikinase enzyme expressed in the cell.

TABLE 4

In vivo Glucan Dikinase Assay

| Acceptor Substrate | [γ-$^{32}$P] ATP −CE, cpm | Phosphate [γ-$^{32}$P] ATP +CE, cpm | Donor [β-$^{32}$P]ATP + [γ-$^{32}$P] ATP −CE, cpm | [β-$^{32}$P]ATP + [γ-$^{32}$P] ATP +CE, cpm |
|---|---|---|---|---|
| Amylopectin | 54 | 78 | 76 | 1,456 |
| Elongated glycogen | 68 | 87 | 76 | 14,269 |
| Glycogen + G1P + Pho | 67 | 564 | 77 | 46,805 |

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

```
SEQ ID NO: 26 Chalydomonas DNA sequence.
Transcript(4074 bp)/CDS Sequence(4074 bp)
ATGGGGATAGACGCTGCCGGGCTGGACACCAACGGCCGCGCGCGCGTGGT

GCTTCACTTGGACGGCGAGGAGGCGTCGGACTTCCTGAACTTCGTGCTGA

AGGACGACGCCACCAACACCTGGTACGACAACAACGGCACCAACTTCAAG

GTGGAGCTGCGCGCCGACGCCTCGCCCAGCGCGCCCAAGCTGGACCAGCT

GCCAAAGGACCTGTGCGACAAGTGGGCCTGGGTGCGCTGGGACTTTGTGG

GCCGGCCGCAGCGCTCCGCCGAGACGGCCGCCTCCGAGTACGACCGCGGC

GTCAGCGAGATGAAGGAGCTGCTGGCGCGCGGGCGGGTGCTGGACGAGCT

GTGGCGCGTGGCGGAGGGCAAGTGGAAGTATTCGGACTACCGCAAGAAGG

TGGTGACGCCCACCATTGGCGACGGCACCGCGCCGCTGTCCGCCCAGCCG
```
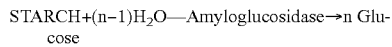
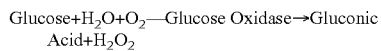
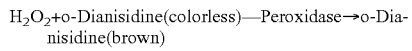

-continued

```
AGCTGGCGGCGGGCTCCAGCCTGGAGGAGGTGGCGGGCCCCCTCAACTAC
ACGCTGAAGCAGCCCACGCCGCCGGCCTCCACGCGCGGCACGCCCGCCGG
CAGCCGCGCCGGCAGCGCCACCTCGTCGCTGGAcggcggcgcggcggcgg
cgcccgcgcggccctcaggcccgccgccgcaggtgggggcgccgcTGGGC
ACGCCCAAGCGCAACCCACTGGACATGATCAAGCGTACCGCGCCCAACCT
GTCTGCCGAGCGCTCGGTGGTGGAGCGGCCGCTGGACTTCCTGGTGCAGC
GCTTTGCGGTGGACCCCGCCACCAAGTGGCGCCGCACATTCCCGCTGGGC
GGCAAGGCGGAGATGCTGGTGGTGGTGCGCCAGGAGGCTGAGAACAAGCC
CATTCGTGTGGACCTGGTGACGGACACGGCCTCGGACGTGGTGCTGCACT
GGGGCGTCAGCCCCATTGGCTCCCGCGAGTGGGTGATGCCGGACGACGGC
GTGCTGCCCGAGGGCAGCATGGTGATGCACAAGGCGGTGGAGACGCCCTT
CCTCAACTGCGACGACGACGAGTGCGACGTGGAGATCAGCGGCGCCAAGG
TGCCGCTGCAGCGCATCACCATCTACCTGCCGGCGGACCACCACCTGGGT
GCGCTGCTGTTCGTGCTGCGCTCCAGCGACAACACCATGTGGTACAAGGA
CGCGGGCGGCAACTTCACGGTGCCGCTGCCCTCCAAGGACAAGCCTGTTG
AGGACACTGCTCCATGGACGTCATCAAGGACGAGCTCAGCCGCACCATC
ATCGAGGCGGAGGTCAACAGCAGCATGTGGACACTCATGCACAGGTTCAA
CAAGGCCGCGGACCTGGTCAGCGAGGTGCTCAACGGCTACTACGACCAGC
TGGACGTGGCCGACGCCATGAGCCGCATCTACGTCTGGCTGCGCTACAGC
GCCACCCGCCACCTCACCTGGCAGCGCAACTACAACACGCAGCCGCGCAT
CCTGTCAGCAGCGCAGGAGCGCCTCACCAACACCATCGCCAACGCGCACG
GCCGCACCACGGGAGAGGCGCAGGAGTGGGTGCGCATGATGCTCACAACG
GTGGGCCGCGGCGGCGACGGCCAGAAGATCCGCGACGAGATCCTGCACAT
CATGCACCGCAACCACATCCCCGAGCGCAAGGGGCTGTGGATGGAGGAGT
GGCACCAGAAGCTGCACAACAACACCACGCCCGACGACGTGCCCATCTGT
GAGGCCTACCTGGCCTTCCTGGAGGGCAACGGCAACATCGGCGCCTACTG
GCGTGTGCTGTCGGACGCAGGCATCACGCGGCAGCGGCTGGAGGGCTTTC
ACCGCGCCATCACGCTGGAGCCCGAGTACTACCCGGAGAAGCGCGACGCG
CTCATCCGCGACTTCCGCAACTACCTGGGCATCCTCAAGGCCGTGCACAG
CGGCGCCGACCTGTCCGCCAGCGCCAGCGCCGCCGGCAACAGGATCCCCG
GCTCCTGCCGCGGCTACCTGGGCTACGTGCTGAGCCACGTGGGCGACAGC
CAGATCCTGCCGCTGCTGGAGGCGTGCGTGGAGGCGCGCACCGAGCTGGC
GCTGAGCGGCACGCTGCCCGGCAGCCGCGAGCTGCTGTACCTGGACCTGG
CGCTGGAGGACCAGGCGCGCCAGGCGGCGGAGCGGGGCGTGGGCGCGGCG
GGCTTCGGCGCCGCCGCCTTCATGCGGCCGCTGCTGCAGAACCTGTGCCT
CAGCCTGGGCAACAACGAGGAGCTGTGCTACTGCCTCAAGGCCTGGAACG
AGCTGCCCCAGTCGGTGCGCACGGCGGGCGGCCCAACAAGGAGGAGGCG
CTGCTGGCCGGTGGCGGTGGTCAACCGCGTGCGGAGAGCGCTCGCGGACAT
CTCTGACCGCACCGTGAACCGCATCGGCGACGTGTCGTCCGCCTACGGCC
GCGCGTTCGGCGTGGAGCACTGGGCCTACGAGCTGTTTGCGGAGGAGGTC
```

-continued

```
ATCCGCGGCGGGCCGGCCTTCGCGGTGTCGCTGGTCATGACCGCCATTGA
GCCCATGCTGCGCAACGCCGCGGCGCTGGGTGCGTGGCAGGTCATCAGCC
CCATTGCGGCCACGGGCGGCGTGGAGGTGGTGGCGGGACTGCACGAGGTG
CAGGACAAGACCTACGACACGCCCACCGTGCTCATCGCGGAGCAGGTGAC
TGGCGAGGAGGAGATCCCGGAGGGCTGCGTGGCCGTCATCACGCCCGACG
CGCCCGACGTGCTGTCGCACGTGTCGGTGCGCGCGCGCAACATGCGTGTG
CTGTTCGCCACCTGCCACGACGACGGGCCGCTCAAGCAGCTGCGCGAGGC
CAAGGGCAAGTGGCTGCACTTCACGCCCTCTGCCAGCGGCGCCGTGTCCT
GGAATGAGACCACTGCGGAGGCGGCGGGCGCAGCGGACGACAGCTCGCAC
TCCACAGTGTCCAAGCCCACGAAGGGCCTGAAGATTGAGGTGCCCAACTG
GTGCGGGCGCTGGGTGGTGGGCATGGAGGAGTACAAGGACGGCGTGGTGG
GCGCCAAGTCCAAGAACCTGGCGGGCCTGCGCGGCCGCCTGCCCGACAAC
ATCAACCTGCCCGCCTCCGTCACGCTGCCCTTCGGCTGCTTCGAGCAGGC
GCTGGAGCTGAAGGAGAACCAGGACATCAAGACCAAGCTGAAGAAGCACG
TGGACGAGGTGCACAAGCACTCCAAGCACCACGCCGACCACACCACCTCC
AACGGGACGGGGCCGTCGCCGGCGGCGCTGCTGGCCGAGTGCCGCAAGCT
GGCCATGCAGGTGGTGTGCCCAAGCAGATCCGCGACGACCTGGCGCAAG
CCATGAAGGGCGCAGGCATCCCGCCGCCCGAGACCGAGGAGCGCTGGGCG
CTGGCGCTGGAGGCCCTGCGCGGCGTGTGGGCGTCCAAGTACAACGACCG
CGCCTACTACTCGCTGCGCAAGGCCGGGCTGGACTTTGACAGCGTGCGCA
TGGCGGTGCTGGTGCAGCGCGTGGTGCCGGCGCAGTACGCGTTCGTGATC
CACACGCGCAACCCCTCCAACAACGACGAGCGCGAGGTGTTCTGCGAGCT
GGTCAAGGGCCTGGGCGAGTCGCTGGTGAGCGGCATGGTGCCCGGCAGCG
CGGTGGCGTTCAAGGCCGCCAAGGACGAGGCGGGGCTGGGGTCGCCCGAG
GTGCTGTGCTACGCCAGCAAGAGCGAGGCCATGTACGTGCGCGACAGCCT
CATCTTCAGGTCCGACTCAAACGGCGAGGACCTGGAGGGATACGCAGGCG
CCGGCCTGTACGAGTCCATCACCATGGACCCCAGCCTGCTCAAGAAGGTG
GACTACATGGAGGACCGGCTGGTGCAGGACCCCGCGTACAGGCGCGACCT
GCTGTCGCGCATCTGCCGCCTGGCGCCTCCATTGAGGGCGCGCTGGGCA
CGGCGCAGGACATTGAGGCCGTGGTGGCGCCCGACGGAGCCATCACCGTT
GTGCAGACGCGCCCGCAGGTGTAG
```

SEQ ID NO: 27
*Chlamydomonas reinhardtii* glucan dikinase
predicted amino acid sequence MGIDAAGLDTNGRARVVLHLDGEEASDFLNFVLKDDATNTWYDNNGTNFK
VELRADASPSAPKLDQLPKDLCDKWAWVRWDFVGRPQRSAEAAASEYDRG
VSEMKELLARGRVLDELWRVAEGKWKYSDYRKKVVTPTIGDGTAPLSAQP
QAQQPAGAPAAAALPAIPEDLLGVQAYILVINDQLAAGSSLEEVAGRLNY
TLKQPTPPASTRGTPAGSRAGSATSSLDGGAAAAPARPSGPPPQVGAPLG
TPKRNPLDMIKRTAPNLSAERSVVERPLDFLVQRFAVDPATKWRRTFPLG
GKAEMLVVVRQEAENKPIRVDLVTDTASDVVLHWGVSPIGSREWVMPDDG
VLPEGSMVMHKAVETPFLNCDDDECDVEISGAKVPLQRITINLPADHHLG

```
ALLFVLRSSDNTMWYKDAGGNFTVPLPSKDKPVEDTRSMDVIKDELSRTI

IEAEVNSSMWTLMHRFNKAADLVSEVLNGYYDQLDVADAMSRIYVWLRYS

ATRHLTWQRNYNTQPRILSAAQERLTNTIANAHGRTTGEAQEWVRMMLTT

VGRGGDGQKIRDEILHIMHRNHIPERKGLWMEEWHQKLHNNTTPDDVPIC

EAYLAFLEGNGNIGAYWRVLSDAGITRQRLEGFDRAITLEPEYYPEKRDA

LIRDFRNYLGILKAVHSGADLSASASAAGNRIPGSCRGYLGYVLSHVGDS

QILPLLEACVEARTELALSGTLPGSRELLYLDLALEDQARQAAERGVGAA

GFGAAAFMRPLLQNLCLSLGNNEELCYCLKAWNELPQSVRTGGRPNKEEA

LLAVAVVNRVRRALADISDRTVNRIGDVSSAYGRAFGVEHWAYELFAEEV

IRGGPAFAVSLVITAIEPMLRNAAALGAWQVISPIAATGRVEVVAGLHEV

QDKTYDTPTVLIAEQVTGEEEIPEGCVAVITPDAPDVLSHVSVRARNMRV

LFATCHDDGPLKQLREAKGKWLHFTPSASGAVSWNETTAEEAAGAADDSSH

STVSKPTKGLKIEVPNWCGRWVVGMDEYKDGVVGAKSKNLAGLRGRLPDN

INLPASVTLPFGCFEQALELKENQDIKTLKKHVDEVHKHSKHHADHTTS

NGTGPSPAALLAECRKLAMQVVVPKQIRDDLAQAMKGAGIPPPETEERWA

LALEALRGVWASKYNDRAYYSLRKAGLDFDSVRMAVLVQRVVPAQYAFVI

HTRNPSNNDEREVFCELVKGLGESLVSGMVPGSAVAFKAAKDEAGLGSPE

VLCYASKSEAMYVRDSLIFRSDSNGEDLEGYAGAGLYESITMDPSLLKKV

DYMEDRLVQDPAYRRDLLSRICRLGASIEGALGTAQDIEGVVAPDGAITV

VQTRPQV*
```

SEQ ID NO: 28 Chlamydomonas reinhardtii - Glucan dikinase sequence - Maize optimized codons:

```
atgggcatcgacgccgccgcctggacaccaacggcagggccagggtggt
gctgcacctggacggcgaggaggccagcgacttcctgaacttcgtgctga
aggacgacgccaccaacacctggtacgacaacaacggcaccaacttcaag
gtggagctgagggccgacgccagcccgagcgccccgaagctggaccagct
gccgaaggacctgtgcgacaagtgggcctgggtgaggtgggacttcgtgg
gcaggccgcagaggagcgccgaggccgccgccagcgagtacgacagggc
gtgagcgagatgaaggagctgctggccaggggcagggtgctggacgagct
gtggaggtggccgagggcaagtggaagtacagcgactacaggaagaagg
tggtgaccccgaccatcggcgacgcaccgccccgctgagcgcccagccg
caggcccagcagccggccggcgcccggccgccgccgccctgccggccat
cccggaggacctgctgggcgtgcaggcctacatcctggtgatcaacgacc
agctggccgccggcagcagcctggaggaggtggccggcaggctgaactac
accctgaagcagccgaccccgccgccagcaccagggcaccccggccgg
cagcagggccgcagcgccaccagcagcctggacggcggcgccgccgccg
ccccggccaggccgagcggcccgccgccgcaggtgggcgcccgctgggc
accccgaagaggaaccccgctggacatgatcaagaggaccgccccgaacct
gagcgccgagaggagcgtggtggagaggccgctggacttcctggtgcaga
ggttcgccgtggacccggccaccaagtggaggaggaccttcccgctgggc
ggcaaggccgagatgctggtggtggtgaggcaggaggccgagaacaagcc
gatcagggtggacctggtgaccgacaccgccagcgacgtggtgctgcact
gggcgtgagcccgatcggcagcagggagtgggtgatgccggacgacggc
gtgctgccggagggcagcatggtgatgcacaaggccgtggagaccccgtt
cctgaactgcgacgacgacgagtgcgacgtggagatcagcggcgccaagg
tgccgctgcagaggatcaccatcaacctgccggccgaccacacctgggc
gccctgctgttcgtgctgaggagcagcgacaacaccatgtggtacaagga
cgccggcggcaacttcaccgtgccgctgccgagcaaggacaagccggtgg
aggacaccaggagcatggacgtgatcaaggacgagctgagcaggaccatc
atcgaggccgaggtgaacagcagcatgtggaccctgatgcacaggttcaa
caaggccgccgacctggtgagcgaggtgctgaacggctactacgaccagc
tggacgtggccgacgccatgagcaggatctacgtgtggctgaggtacagc
gccacccaggcacctgacctggcagaggaactacaacacccagccgaggat
cctgagcgccgcccaggagaggctgaccaacaccatcgccaacgcccacg
gcaggaccaccggcgaggcccaggagtgggtgaggatgatgctgaccacc
gtgggcaggggcggcgacggcagaagatcagggacgagatcctgcacat
catgcacaggaaccacatcccggagaggaagggcctgtggatggaggagt
ggcaccagaagctgcacaacaacaccaccccggacgacgtgccgatctgc
gaggcctacctggccttcctggagggcaacggcaacatcggcgcctactg
gagggtgctgagcgacgccggcatcaccaggcagaggctggagggcttcg
acagggccatcaccctggagccggagtactacccggagaagagggacgcc
ctgatcagggacttcaggaactacctgggcatcctgaaggccgtgcacag
cggcgccgacctgagcgccagcgccagcgccgccggcaacaggatcccgg
gcagctgcaggggctacctgggctacgtgctgagccacgtgggcgacagc
cagatcctgccgctgctggaggcctgcgtggaggccaggaccgagctgc
cctgagcggcaccctgccgggcagcagggagctgctgtacctggacctgg
ccctggaggaccaggccaggcaggccgccgagagggcgtgggcgccgcc
ggcttcggcgccgccgccttcatgaggccgctgctgcagaacctgtgcct
gagcctgggcaacaacgaggagctgtgctactgcctgaaggcctggaacg
agctgccgcagagcgtgaggaccggcggcaggccgaacaaggaggaggcc
ctgctggccgtggccgtggtgaacagggtgaggagggccctggccgacat
cagcgacaggaccgtgaacaggatcggcgacgtgagcagcgcctacggca
gggccttcggcgtggagcactgggcctacgagctgttcgccgaggaggtg
atcagggccggcccggccttcgccgtgagcctggtgatcaccgccatcga
gccgatgctgaggaacgccgccgccctgggcgcctggcaggtgatcagcc
cgatcgccgccaccggcagggtggaggtggtggccggcctgcacgaggtg
caggacaagacctacgacacccccaccgtgctgatcgccgagcaggtgac
cggcgaggaggagatcccggagggctgcgtggccgtgatcacccggacg
ccccggacgtgctgagccacgtgagcgtgagggccaggaacatgagggtg
ctgttcgccacctgccacgacgacggcccgctgaagcagctgagggaggc
caagggcaagtggctgcacttcaccccgagcgccagcggcgccgtgagct
ggaacgagaccaccgccgaggccgccggcgccgccgacgacagcagccac
```

```
agcaccgtgagcaagccgaccaagggcctgaagatcgaggtgccgaactg
gtgcggtaggtgggtggtgggcatggacgagtacaaggacggcgtggtgg
gcgccaagagcaagaacctggccggcctgaggggcaggctgccggacaac
atcaacctgccggccagcgtgaccctgccgttcggctgcttcgagcaggc
cctggagctgaaggagaaccaggacatcaagaccaagctgaagaagcacg
tggacgaggtgcacaagcacagcaagcaccacgccgaccacaccaccagc
aacggcaccggcccgagcccggccgccctgctggccgagtgcaggaagct
ggccatgcaggtggtggtgccgaagcagatcagggacgacctggcccagg
ccatgaagggcgccggcatcccgccgccgagaccgaggagaggtgggcc
ctggccctggaggccctgaggggcgtgtgggccagcaagtacaacgacag
ggcctactacagcctgaggaaggccggcctggacttcgacagcgtgagga
tggccgtgctggtgcagagggtggtgccggcccagtacgccttcgtgatc
cacaccaggaacccgagcaacaacgacgagagggaggtgttctgcgagct
ggtgaagggcctgggcgagagcctggtgagcggcatggtgccgggcagcg
ccgtggccttcaaggccgccaaggacgaggccggcctgggcagcccggag
gtgctgtgctacgccagcaagagcgaggccatgtacgtgagggacagcct
gatcttcaggagcgacagcaacggcgaggacctggagggctacgccggcg
ccggcctgtacgagagcatcaccatggacccgagcctgctgaagaaggtg
gactacatggaggacaggctggtgcaggacccggcctacaggagggacct
gctgagcaggatctgcaggctgggcgccagcatcgagggcgccctgggca
ccgcccaggacatcgagggcgtggtggccccggacggcgccatcaccgtg
gtgcagaccaggccgcaggtgtga
```

SEQ ID NO: 29 Chlamydomonas reinhartii - Glucan dikinase sequence (with few mutation to reduce homology to antigen 80-mer database) - using optimized Maize-codon:

```
atgggcatcgacgccgccggcctggacaccaacggcagggccagggtggt
gctgcacctggacggcgaggaggccagcgacttcctgaacttcgtgctga
aggacgacgccaccaacacctggtacgacaacaacggcaccaacttcaag
gtggagctgagggccgacgccagcccgagcgccccgaagctggaccagct
gccgaaggacctgtgcgacaagtgggcctgggtgaggtgggacttcgtgg
gcaggccgcagaggagcgccgaggccgccgccagcgagtacgacagggg c
gtgagcgagatgaaggagctgctggccaggggcagggtgctggacgagct
gtggagggtggccgagggcaagtggaagtacagcgactacaggaagaagg
tggtgaccccgaccatcggcgacggcaccgccccgctgagcgcccagccg
caggcccagcagccggccggcgcccggccgccgccggcctgccggccat
cccggaggacctgctgggcgtgcaggcctacatcctggtgatcaacgacc
agctggccggcggcagcagcctggaggaggtggccggcaggctgaactac
accctgaagcagccgacccgccggccagcaccaggggcaccccggccgg
cagcagggccggcagcgccaccagcagcctggacggcggcggcgccgcc
ccccgccaggccgagcggcccgccgccgcaggtgggcgccccgctgggc
accccgaagaggaacccgctggacatgatcaaggaggaccgccccgaacct
gagcgccgagaggagcgtggtggagaggccgctggacttcctggtgcaga
ggttcgccgtggacccggccaccaagtggaggaggaccttcccgctgggc
ggcaaggccgagatgctggtggtggtgaggcaggaggccgagaacaagcc
gatcagggtggacctggtgaccgacaccgccagcgacgtggtgctgcact
ggggcgtgagcccgatcggcagcagggagtgggtgatgccgacgacggc
gtgctgccggagggcagcatggtgatgcacaaggccgtggagaccccgtt
cctgaactgcgacgacgacgagtgcgacgtggagatcagcggcgccaagg
tgccgctgcagaggatcaccatcaacctgccggccgaccaccacctgggc
gccctgctgttcgtgctgaggagcagcgacaacaccatgtggtacaagga
cgccggcggcaacttcaccgtgccgctgccgagcaaggacaagccggtgg
aggacaccaggagcatggacgtgatcaaggacgagctgagcaggaccatc
atcgaggccgaggtgaacagcagcatgtggaccctgatgcacaggttcaa
caaggccgccgacctggtgagcgaggtgctgaacggctactacgaccagc
tggacgtggccgacgccatgagcaggatctacgtgtggctgaggtacagc
gccaccaggcacctgacctggcagaggaactacaacacccagccgaggat
cctgagcgccgcccaggagaggctgaccaacaccatcgccaacgcccacg
gcaggaccaccggcgagcccaggagtgggtgaggatgatgctgaccacc
gtgggcaggggcggcgacggccagaagatcagggacgagatcctgcacat
catgcacaggaaccacatcccggagaggaagggcctgtggatggaggagt
ggcaccagaagctgcacaacaacaccaccccggacgacgtgccgatctgc
gaggcctacctggccttcctggagggcaacggcaacatcggcgcctactg
gagggtgctgagcgacgccggcatcaccaggcagaggctggagggcttcg
acagggccatcaccctggagccggagtactacccggagaagagggacgcc
ctgatcagggacttcaggaactacctgggcatcctgaaggccgtgcacag
cggcgccgacctgagcgccagcgccagcgccggcggcaacaggatcccgg
gcagctgcagggctacctgggctacgtgctgagccacgccggcgacgcca
gatcctgccgctgctggaggcctgcgtggaggccaggaccgagctggccc
tgagcggcaccctgccgggcagcagggagctgctgtacctggacctggcc
ctggaggaccaggccaggcaggccgccgagaggggcgtgggcgccgccgg
cttcggcgccgccgccttcatgaggccgctgctgcagaacctgtgcctga
gcctgggcaacaacgaggagctgtgctactgcctgaaggcctggaacgag
ctgccgcagagcgtgaggaccggcggcaggccgaacaaggaggaggccct
gctggccgtggccgtggtgaacagggtgaggagggccctggccgacatca
gcgacaggaccgtgaacaggatcggcgacgtgagcagcgcctacggcagg
gccttcggcgtggagcactgggcctacgagttgttcgccgaggaggtgat
caggggcggccccgccttcgccgtgagcctggtgatcaccgccatcgagc
cgatgctgaggaacgccgccgccctgggcgcctggcaggtgatcagcccg
atcgccgccaccggcagggtggaggtggtggccggcctgcacgaggtgca
ggacaagacctacgacaccccgaccgtgctgatcgccgagcaggtgaccg
gcgaggaggatcccggagggctgcgtggccgtgatcaccccggacgcc
ccggacgtgctgagccacgtgagcgtgagggccaggaacatgagggtgct
```

-continued
```
gttcgccacctgccacgacgacggcccgctgaagcagctgagggaggcca
agggcaagtggctgcacttcaccccgagcgccagcggcgccgtgagctgg
aacgagaccaccgccgaggccgccggcgccgccgacgacagcagccacag
caccgtgagcaagccgaccaagggcctgaagatcgaggtgccgaactggt
gcggcaggtgggtggtgggcatggacgagtacaaggacgycgtggtgggc
gccaagagcaagaacctggccggcctgaggggcaggctgtcggacaacat
caacctgccggccagcgtgaccctgccgttcggctgcttcgagcaggccc
tggagctgaaggagaaccaggacatcaagaccaagctgaagaagcacgtg
gacgaggtgcacaagcacagcaagcaccacgccgaccacaccaccagcaa
cggcaccggcccgagcccggccgccctgctggccgagtgcaggaagctgg
ccatgcaggtggtggtgccgaagcagatcagggacgacctggcccaggcc
atgaagggcgccggcatcccgccgccggagaccgaggagaggtgggccct
ggccctggaggcctgaggggcgtgtgggccagcaagtacaacgacaggg
cctactacagcctgaggaaggccggcctggacttcgacagcgtgaggatg
gccgtgctggtgcagagggtggtgccggcccagtacgccttcgtgatcca
caccaggaacccgagcaacaacgacgagagggaggtgttctgcgagctgg
tgaagggcctgggcgagagcctggtgagcggcatggtgccgggcagcgcc
gtggccttcaaggccgccaaggacgaggccggcctgggcagcccggaggt
gctgtgctacgccagcaagagcgaggccatgtacgtgagggacagcctga
tcttcaggagcgacagcaacggcgaggacctggagggctacgccggcgcc
ggcctgtacgagagcatcaccatggacccgagcctgctgaagaaggtgga
ctacatggaggacaggctggtgcaggacccggcctacaggagggacctgc
tgagcaggatctgcaggctgggcgccagcatcgagggcgccctgggcacc
gcccaggacatcgagggcgtggtggccccggacggcgccatcaccgtggt
gcagaccaggccgcaggtgtga
```

SEQ ID NO: 30
*Chlamydomonas reinhardtii* glucan dikinase
(Some mutations, indicated in red, are introduced
to reduce the homology to allergen database
(80 mer) below 35%)

MGIDAAGLDTNGRARVVLHLDGEEASDFLNFVLKDDATNTWYDNNGTNFK
VELRADASPSAPKLDQLPKDLCDKWAWVRWDFVGRPQRSAEAAASEYDRG
VSEMKELLARGRVLDELWRVAEGKWKYSDYRKKVVTPTIGDGTAPLSAQP
QAQQPAGAPAAAGLPAIPEDLLGVQAYILVINDQLAGGSSLEEVAGRLNY
TLKQPTPPASTRGTPAGSRAGSATSSLDGGGAAAPARPSGPPPQVGAPLG
TPKRNPLDMIKRTAPNLSAERSVVERPLDFLVQRFAVDPATKWRRTFPLG
GKAEMLVVVRQEAENKPIRVDLVTDTASDVVLHWGVSPIGSREWVIPDDG
VLPEGSMVMHDAVETPFLNCDDDECDVEISGAKVPLQRITINLPADHHLG
ALLFVLRSSDNTMWYKADGGNFTVPLPSKDKPVEDTRSMDVIKDELSRTI
IEAEVNSSMWTLMHRFNKAADLVSEVLNGYYDQLDVADAMSRIYVWLRYS
ATRHLTWQRNYNTQPRILSAAQERLTNTIANAHGRTTGEAQEWVRMMLTT
VGRGGDGQKIRDEILHIMHRNHIPERKGLWMEEWHQKLHNNTTPDDVPIC
EAYLAFLEGNGNIGAYWRVLSDAGITRQRLEGFDRAITLEPEYYPEKRDA

-continued

LIRDFRNYLGILKAVHSGADLSASASAGGNRIPGSCRGYLGYVLSHAGDS
QILPLLEACVEARTELALSGTLPGSRELLYLDLALEDQARQAAERGVGAA
GFAAAFMRPLLQNLCLSLGNNEELCYCLKAWNELPQSVRTGGRPNKEEAL
LAVAVVNRVRRALADISDRTVNRIGDVSSAYGRAFGVEHWAYELFAEEVI
RGGPAFAVSLVITAIEPMLRNAAALGAWQVISPIAATGRVEVVAGLEVQD
KTYDTPTVLIAEQVTGEEEIPEGCVAVITPDAPDVLSHVSVRARNMRVLF
ATCHDDGPLKQLREAKGKWLHFTPSASGAVSWNETTAEAAGAADDSSHST
VSKPTKGLKIEVPNWCGRWVVGMDEYKDGVVGAKSKNLAGLRGRLPDNIN
LPASVTLPFGCFEQALELKENQDIKTKLKKHVDEVHKHSKHHADHTTSNG
TGPSAPAALLAECRKLAMQVVVPKQIRDDLAQAMKGAGIPPPETEERWAL
ALEALRGVWASKYNDRAYYSLRKAGLDFDSVRMAVLVQRVVPAQYAFVIH
TRNPSNNDEREVFCELVKGLGESLVSGMVPGSAVAFKAAKDEAGLGSPEV
LCYASKSEAMYVRDSLIFRSDSNGEDLEGYAGAGLYESITMDPSLLKKVD
YMEDRLVQDPAYRRDLLSRICRLGASIEGALGTAQDIEGVVAPDGAITVV
QTRPQV*

Seq. ID. No: 31: Nucleotide sequence for the maize codon-optimized synthetic R1:

GGATCCACCATGGGTAATTCCCTCGGCAACAACCTCCTCTACCAGGGCTT
CCTCACCTCCACCGTGCTCGAGCACAAGTCCCGCATCTCCCCGCCGTGCG
TGGGCGGCAACTCCCTCTTCCAGCAGCAGGTGATCTCCAAGTCCCCGCTC
TCCACCGAGTTCCGCGGCAACCGCCTCAAGGTGCAGAAGAAGAAGATCCC
GATGGAGAAGAAGCGCGCCTTCTCCTCCTCCCCGCACGCCGTGCTCACCA
CCGACACCTCCTCCGAACTCGCCGAGAAGTTCTCCCTCGGCGGCAACATC
GAACTCCAGGTGGACGTGCGCCCGCCGACCTCCGGCGACGTGTCCTTCGT
GGACTTCCAGGTGACCAACGGCTCCGACAAGCTCTTCCTCCACTGGGGCG
CCGTGAAGTTCGGCAAGGAGACCTGGTCCCTCCCGAACGACCGCCCGGAC
GGCACCAAGGTGTACAAGAACAAGGCCCTCCGCACCCCGTTCGTGAAGTC
CGGCTCCAACTCCATCCTCCGCCTCGAGATCCGCGACACCGCCATCGAGG
CCATCGAGTTCCTCATCTACGACGAGGCCCACGACAAGTGGATCAAGAAC
AACGGCGGCAACTTCCGCGTGAAGCTCTCCCGCAAGGAGATCCGCGGCCC
GGACGTGTCCGTGCCGGAGGAACTCGTGCAGATCCAGTCCTACCTCCGCT
GGGAGCGCAAGGGCAAGCAGAACTACCCGCCGGAGAAGGAGAAGGAGGAG
TACGAGGCTGCTCGCACCGTGCTCCAGGAGGAGATCGCTCGCGGTGCCTC
CATCCAGGACATCCGCGCCCGCCTCACCAAGACCAACGACAAGTCCCAGT
CCAAGGAGGAGCCGCTCCACGTGACCAAGTCCGACATCCCGGACGACCTC
GCCCAGGCCCAGGCCTACATCCGCTGGGAGAAGGCCGGCAAGCCGAACTA
CCCGCCGGAGAAGCAGATCGAGGAACTCGAGGAGGCCCGCCGCGAACTCC
AGCTCGAACTCGAGAAGGGCATCACCCTCGACGAACTCCGCAAGACCATC
ACCAAGGGCGAGATCAAGACCAAGGTGGAGAAGCACCTCAAGCGCTCCTC
CTTCGCCGTGGAGCGCATCCAGCGCAAGAAGCGCGACTTCGGCCACCTCA
TCAACAAGTACACCTCCTCCCCTGCCGTGCAGGTGCAGAAGGTGCTCGAG
GAGCCACCAGCCCTCTCCAAGATCAAGCTCTACGCCAAGGAGAAGGAGGA

GCAGATCGACGACCCGATCCTCAACAAGAAGATCTTCAAGGTGGACGACG
GCGAACTCCTCGTGCTCGTGGCCAAGTCCTCCGGCAAGACCAAGGTGCAC
CTCGCCACCGACCTCAACCAGCCGATCACCCTCCACTGGGCCCTCTCCAA
GTCCCCGGGCGAGTGGATGGTGCCGCCGTCCTCCATCCTCCCGCCGGGCT
CCATCATCCTCGACAAGGCCGCCGAGACCCCGTTCTCCGCCTCCTCCTCC
GACGGCCTCACCTCCAAGGTGCAGTCCCTCGACATCGTGATCGAGGACGG
CAACTTCGTGGGCATGCCGTTCGTGCTCCTCTCCGGCGAGAAGTGGATCA
AGAACCAGGGCTCCGACTTCTACGTGGGCTTCTCCGCCGCCTCCAAGCTC
GCCCTCAAGGCTGCTGGCGACGGCTCCGGCACCGCCAAGTCCCTCCTCGA
CAAGATCGCCGACATGGAGTCCGAGGCCCAGAAGTCCTTCATGCACCGCT
TCAACATCGCCGCCGACCTCATCGAGGACGCCACCTCCGCCGGCGAAGTC
GGCTTCGCCGGCATCCTCGTGTGGATGCGCTTCATGGCCACCCGCCAGCT
CATCTGGAACAAGAACTACAACGTGAAGCCGCGCGAGATCTCCAAGGCCC
AGGACCGCCTCACCGACCTCCTCCAGAACGCCTTCACCTCCCACCCGCAG
TACCGCGAGATCCTCCGCATGATCATGTCCACCGTGGGTCGCGGTGGCGA
GGGCGACGTGGGCCAGCGCATCCGCGACGAGATCCTCGTGATCCAGCGCA
ACAACGACTGCAAGGGCGGCATGATGCAGGAGTGGCACCAGAAGCTCCAC
AACAACACCTCCCCGGACGACGTGGTGATCTGCCAGGCCCTCATCGACTA
CATCAAGTCCGACTTCGACCTCGGCGTGTACTGGAAGACCCTCAACGAGA
ACGGCATCACCAAGGAGCGCCTCCTCTCCTACGACCGCGCCATCCACTCC
GAGCCGAACTTCCGCGGCGACCAGAAGGGCGGCCTCCTCCGCGACCTCGG
CCACTACATGCGCACCCTCAAGGCCGTGCACTCCGGCGCCGACCTCGAGT
CCGCCATCGCCAACTGCATGGGCTACAAGACCGAGGGCGAGGGCTTCATG
GTGGGCGTGCAGATCAACCCGGTGTCCGGCCTCCCGTCCGGCTTCCAGGA
CCTCCTCCACTTCGTGCTCGACCACGTGGAGGACAAGAACGTGGAGACCC
TCCTCGAGCGCCTCCTCGAGGCCCGCGAGGAACTCCGCCCGCTCCTCCTC
AAGCCGAACAACCGCCTCAAGGACCTCCTCTTCCTCGACATCGCCCTCGA
CTCCACCGTGCGCACCGCCGTGGAGCGCGGCTACGAGGAACTCAACAACG
CCAACCCGGAGAAGATCATGTACTTCATCTCCCTCGTGCTCGAGAACCTC
GCCCTCTCCGTGGACGACAACGAGGACCTCGTGTACTGCCTCAAGGGCTG
GAACCAGGCCCTCTCCATGTCCAACGGCGGCGACAACCACTGGGCCCTCT
TCGCCAAGGCCGTGCTCGACCGCACCCGCCTCGCCCTCGCCTCCAAGGCC
GAGTGGTATCACCACCTCCTCCAGCCGTCCGCCGAGTACCTCGGCTCCAT
CCTCGGCGTGGACCAGTGGGCCCTCAACATCTTCACCGAGGAGATCATCC
GCGCCGGCTCCGCCGCCTCCCTCTCCTCCTCCTCAACCGCCTCGACCCG
GTGCTCCGCAAGACCGCCAACCTCGGCTCCTGGCAGATCATCTCCCCGGT
GGAGGCCGTGGGCTACGTGGTGGTGGTGGACGAACTCCTCTCCGTGCAGA
ACGAGATCTACGAGAAGCCGACCATCCTCGTGGCCAAGTCCGTGAAGGGC
GAGGAGGAGATCCCGGACGGCGCCGTGGCCCTCATCACCCCGGACATGCC
GGACGTGCTCTCCCACGTGTCCGTGCGCGCCCGCAACGGCAAGGTGTGCT
TCGCCACCTGCTTCGACCCGAACATCCTCGCCGACCTCCAGGCCAAGGAG
GGCCGCATCCTCCTCCTCAAGCCGACCCCGTCCGACATCATCTACTCCGA
GGTGAACGAGATCGAACTCCAGTCCTCCTCCAACCTCGTGGAGGCCGAGA
CCTCCGCCACCCTCCGCCTCGTGAAGAAGCAGTTCGGCGGCTGCTACGCC
ATCTCCGCCGACGAGTTCACCTCCGAGATGGTGGGCGCCAAGTCCCGCAA
CATCGCCTACCTCAAGGGCAAGGTGCGTCCTCCGTGGGCATCCCGACCT
CCGTGGCCCTCCCCGTTCGGCGTGTTCGAGAAGGTGCTCTCCGACGACATC
AACCAGGGCGTGGCCAAGGAACTCCAGATCCTCATGAAGAAGCTCTCCGA
GGGCGACTTCTCCGCCCTCGGCGAGATCCGCACCACCGTGCTCGACCTCT
CCGCCCCGGCCCAGCTCGTGAAGGAACTCAAGGAGAAGATGCAGGGCTCC
GGCATGCCGTGGCCGGGCGACGAGGGCCCGAAGCGCTGGGAGCAGGCCTG
GATGGCCATCAAGAAGGTGTGGGCCTCCAAGTGGAACGAGCGCGCCTACT
TCTCCACCCGCAAGGTGAAGCTCGACCACGACTACCTCTGCATGGCCGTG
CTCGTGCAGGAGATCATCAACGCCGACTACGCCTTCGTGATCCACACCAC
CAACCCGTCCTCCGGCGACGACTCCGAGATCTACGCCGAGGTGGTGCGCG
GCCTCGGCGAGACCCTCGTGGGAGCCTACCCAGGACGCGCACTCTCCTTC
ATCTGCAAGAAGAAGGACCTCAACTCCCCGCAGGTGCTCGGCTACCCGTC
CAAGCCGATCGGCCTCTTCATCAAGCGCTCCATCATCTTCCGCTCCGACT
CCAACGGCGAGGACCTCGAGGGCTACGCCGGCGCCGGCCTCTACGACTCC
GTGCCGATGGACGAGGAGGAGAAGGTGGTGATCGACTACTCCTCCGACCC
GCTCATCACCGACGGCAACTTCGCCAGACCATCCTCTCCAACATCGCCC
GCGCCGGCCACGCCATCGAGGAACTCTACGGCTCCCCGCAGGACATCGAG
GGCGTGGTGCGCGACGGCAAGATCTACGTGGTGCAGACCCGCCCCGCAGAT
GTAGAGCTC

---

We claim:

1. An isolated nucleic acid molecule having 95%, sequence similarity to SEQ ID NO: 26, wherein the nucleic acid encodes a polypeptide having glucan dikinase activity.

2. The isolated nucleic acid molecule of claim 1, wherein the nucleic acid molecule comprises SEQ ID NO: 26.

3. An isolated nucleic acid molecule encoding a polypeptide having 95% sequence similarity to SEQ ID NO: 27, wherein the polypeptide has glucan dikinase activity.

4. The isolated nucleic acid molecule of claim 3, wherein the nucleic acid molecule encodes a polypeptide comprising the amino sequence of SEQ ID NO: 27.

5. An isolated nucleic acid molecule having 95% sequence similarity to SEQ ID NO: 28, wherein the nucleic acid encodes a polypeptide having glucan dikinase activity.

6. The isolated nucleic acid molecule of claim 5, wherein the nucleic acid molecule comprises SEQ ID NO: 28.

7. An isolated nucleic acid molecule encoding a polypeptide having 95% sequence similarity to SEQ ID NO: 30, wherein the polypeptide has glucan dikinase activity.

8. The isolated nucleic acid molecule of claim 7, wherein the nucleic acid molecule encodes a polypeptide comprising the amino sequence of SEQ ID NO: 30.

9. An isolated polypeptide having 95% sequence similarity to SEQ ID NOs: 27 or 30, wherein the polypeptide has glucan dikinase activity.

10. The isolated polypeptide of claim 9, wherein the isolated polypeptide molecule comprises the amino acid sequence of SEQ ID NOs: 27 or 30.

11. A transgenic plant or transgenic plant part comprising the nucleic acid molecule of claim 3.

12. A transgenic plant or transgenic plant part comprising the nucleic acid molecule of claim 7.

13. The plant or plant part of claim 11, wherein the nucleic acid molecule is linked to a regulatory element that ensures transcription in plant cells.

14. The plant or plant part of claim 12, wherein the nucleic acid molecule is linked to an endosperm specific promoter.

15. The plant or plant part of claim 12, wherein the nucleic acid molecule is linked to a leaf specific promoter.

16. The plant or plant part of claim 11, wherein a nucleic acid encodes a polypeptide comprising SEQ ID NO: 27 or 30.

17. Animal feed comprising the plant or plant part of claim 11.

18. A method of increasing the fermentable starch in plant or plant parts comprising:
   a. inserting an expression cassette into a plant cell comprising a nucleic acid encoding an green alga glucan dikinase polypeptide;
   b. regeneration of transgenic plants from the plant cell of a); and
   c. producing said fermentable starch.

19. A method of producing a modified phosphorylated starch in plant comprising:
   a. inserting an expression cassette into a plant cell comprising a nucleic acid encoding an green alga glucan dikinase polypeptide;
   b. regeneration of transgenic plants from the plant cell of a); and
   c. producing said modified starch.

* * * * *